United States Patent
Doyle et al.

(10) Patent No.: US 12,358,980 B2
(45) Date of Patent: Jul. 15, 2025

(54) COMPOSITIONS AND METHODS FOR ANTI-PACAP ANTIBODIES

(71) Applicant: Cephalon, LLC, West Chester, PA (US)

(72) Inventors: Anthony Gerard Doyle, Drummoyne (AU); Adam Clarke, Riverstone (AU); Danyal Butt, St. Leonards (AU); David Laine, Gladesville (AU); Hugh MacRae, Newtown (AU); Jenny Vo, Melrose Park (AU); Julia Rozenfeld, Gordon (AU); Sachin Surade, Waitara (AU)

(73) Assignee: CEPHALON LLC, West Chester, PA (US)

(*) Notice: Subject to any disclaimer, the term of this patent is extended or adjusted under 35 U.S.C. 154(b) by 0 days.

(21) Appl. No.: 17/815,749

(22) Filed: Jul. 28, 2022

(65) Prior Publication Data

US 2023/0212281 A1    Jul. 6, 2023

Related U.S. Application Data

(60) Provisional application No. 63/226,875, filed on Jul. 29, 2021.

(51) Int. Cl.
*C07K 16/26* (2006.01)
*A61K 39/00* (2006.01)

(52) U.S. Cl.
CPC .............. *C07K 16/26* (2013.01); *A61K 39/00* (2013.01); *C07K 2317/24* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| | | |
|---|---|---|
| 2018/0362643 A1 | 12/2018 | Hamburger et al. |
| 2019/0233498 A1 | 8/2019 | Loomis et al. |

FOREIGN PATENT DOCUMENTS

| | | | |
|---|---|---|---|
| WO | WO-91/014786 A1 | 10/1991 | |
| WO | WO-2004/062684 A2 | 7/2004 | |
| WO | WO-2008/018472 A1 | 2/2008 | |
| WO | WO-2010/054007 A1 | 5/2010 | |
| WO | WO-2012/106407 A2 | 8/2012 | |
| WO | WO-2014/130657 A1 | 8/2014 | |
| WO | WO-2014/144632 A2 | 9/2014 | |
| WO | WO-2016/044224 A1 | 3/2016 | |
| WO | WO-2016/168757 A1 | 10/2016 | |
| WO | WO-2016/168760 A1 | 10/2016 | |
| WO | WO-2016/168762 A2 | 10/2016 | |
| WO | WO-2016/168768 A2 | 10/2016 | |
| WO | WO-2017/106578 A1 | 6/2017 | |
| WO | WO-2017/181031 A2 | 10/2017 | |
| WO | WO-2017/181039 A1 | 10/2017 | |
| WO | WO-2018/152687 A1 | 8/2018 | |
| WO | WO-2019/067293 A1 | 4/2019 | |
| WO | WO-2019/140216 A1 | 7/2019 | |
| WO | WO-2020/264384 A1 | 12/2020 | |
| WO | WO-2023/010065 A2 | 2/2023 | |
| WO | WO-2024/171078 A1 | 8/2024 | |
| WO | WO-2024/218541 A1 | 10/2024 | |

OTHER PUBLICATIONS

Gao et al., BMC Biotechnology 2013, 13:55 http://www.biomedcentral.com/1472-6750/13/55 (Year: 2013).*
Ashina et al., Cephalalgia 2021, vol. 41(1) 33-44 (Year: 2021).*
Clancy et al., Neuropsychopharmacology (2023) 48:1245-1254; https://doi.org/10.1038/s41386-023-01593-5 (Year: 2023).*
AHS Consensus Statement (Jan. 2019, e-published Dec. 10, 2018). "The American Headache Society Position Statement on Integrating New Migraine Treatments into Clinical Practice," *Headache* 59(1):1-18.
Aubdool, A.A. et al. (Aug. 2016, e-published Jun. 21, 2016). "TRPA1 activation leads to neurogenic vasodilatation: involvement of reactive oxygen nitrogen species in addition to CGRP and NO," *British Journal of Pharmacology* 173(15):2419-2433.
Bourgault, S. (May 2009). "Molecular and conformational determinants of pituitary adenylate cyclase-activating polypeptide (PACAP) for activation of the PAC1 receptor," *J Med Chem* 52(10):3308-3316.
D'Antona, L. et al. (Aug. 23, 2019). "Identifying and managing refractory migraine: barriers and opportunities?" *J Headache Pain* 20(1):89.
Dyson, M.R. et al. (Jan.-Dec. 2020). "Beyond affinity: selection of antibody variants with optimal biophysical properties and reduced immunogenicity from mammalian display libraries," *mAbs* 12(1):1829335.
Greco, R. et al. (Jul. 13, 2018). "Chronic and intermittent administration of systemic nitroglycerin in the rat induces an increase in the gene expression of CGRP in central areas: potential contribution to pain processing," *J Headache Pain* 19:51.
Hannibal, J. et al. (Jan. 26, 1995). "Gene expression of pituitary adenylate cyclase activating polypeptide (PACAP) in the rat hypothalamus," *Regul Pept* 55(2):133-148.
Hannibal, J. et al. (Apr. 1, 1997) "Pituitary adenylate cyclase-activating peptide (PACAP) in the retinohypothalamic tract: a potential daytime regulator of the biological clock," *The Journal of Neuroscience* 17(7):2637-2644.
Hirabayashi, T. et al. (Apr. 4, 2018). "Discovery of PACAP and its receptors in the brain," *J Headache Pain* 19(1):28.

(Continued)

*Primary Examiner* — Christina M Borgeest
(74) *Attorney, Agent, or Firm* — Mintz, Levin, Cohn, Ferris, Glovsky and Popeo, P.C.

(57) ABSTRACT

The present disclosure generally relates to anti-PACAP antibodies, pharmaceutical compositions comprising such antibodies, and methods of producing and using such antibodies.

20 Claims, 10 Drawing Sheets

Specification includes a Sequence Listing.

(56) References Cited

OTHER PUBLICATIONS

International Search Report mailed on Feb. 1, 2023, for PCT Application No. PCT/US2022/074238, filed Jul. 28, 2022, 5 pages.
Kohli, N. et al. (Feb. 25, 2015). "A novel screening method to assess developability of antibody like molecules," *mAbs* 7(4):752-758.
Kuburas, A. et al. (May 26, 2021, e-published Apr. 12, 2021). "PACAP Induces Light Aversion in Mice by an Inheritable Mechanism Independent of CGRP," *J Neurosci* 41(21):4697-4715.
Loomis, C.M. et al. (Apr. 2019, e-published Jan. 14, 2019). "Pharmacologic Characterization of ALD1910, a Potent Humanized Monoclonal Antibody against the Pituitary Adenylate Cyclase-Activating Peptide," *J Pharmacol Exp Ther* 369(1):26-36.
Loomis, C.M. et al. (2019). IHC-LB-075, In Vivo Antagonistic Activity and Endogenous Target Engagement of an Anit-PACAP Monoclonal Antibody in Cynomolgus Monkeys, p. 407 of IHC 2019 Abstracts.
Lundbeck Investor Presentation Q1 2020, 60 pages.
Lundbeck announces positive phase II Proof of Concept results with Lu AG09222 in migraine prevention, Corporate Release No. 740, Apr. 19, 2023, 3 pages.
Markovics, A. et al. (Jan. 2012, e-published Oct. 18, 2011). "Pituitary adenylate cyclase-activating polypeptide plays a key role in nitroglycerol-induced trigeminovascular activation in mice," *Neurobiology of Disease* 45(1):633-644.
Robberecht et al (Jul. 1, 1992). "Structural requirements for the occupancy of pituitary adenylate-cyclase-activating-peptide (PACAP) receptors and adenylate cyclase activation in human neuroblastoma NB-OK-1 cell membranes. Discovery of PACAP(6-38) as a potent antagonist," *Eur J Biochem* 207(1):239-246.
Sacco, S. et al. (Jun. 16, 2020). "European headache federation consensus on the definition of resistant and refractory migraine: Developed with the endorsement of the European Migraine & Headache Alliance (EMHA)," *J Headache Pain* 21(1):76.
Schwarzhoff, R. et al. (Jan. 5, 1995). "Specific monoclonal antibodies neutralize the action of PACAP 1-27 or PACAP 1-38 on intestinal muscle strips in vitro," *Regul Pept* 55(1):57-66.
Schytz, H.W. et al. (Jan. 2009). "PACAP38 induces migraine-like attacks in patients with migraine without aura," *Brain* 132(1):16-25.
Suzuki, N. et al. (May 1993). "Production of immunoreactive pituitary adenylate cyclase activating polypeptide (PACAP) by human neuroblastoma cells, IMR-32: detection and characterization with monoclonal and polyclonal antibodies against different epitopes of PACAP," *J Biochem* 113(5):549-556.
Wei, M.-X. et al. (Oct. 14, 2010). "Possible key residues that determine left gastric artery blood flow response to PACAP in dogs," *World J Gastroenterol* 16(38):4865-4870.
Written Opinion mailed on Feb. 1, 2023, for PCT Application No. PCT/US2022/074238, filed Jul. 28, 2022, 8 pages.

\* cited by examiner

FIG. 1

| | | |
|---|---|---|
| VIP | HSDAVFTDNYTRLRKQMAVKKYLNSILN--------------- | SEQ ID NO 15 |
| PACAP38 | HSDGIFTDSYSRYRKQMAVKKYLAAVLGKRYKQRVKNK | SEQ ID NO 13 |
| PACAP27 | HSDGIFTDSYSRYRKQMAVKKYLAAVL--------------- | SEQ ID NO 14 |
| | *.:**.:*:.*********   .:.* | |

FIG. 2A  VL alignment

```
                                    CDR-1                              CDR-2
054M  DIVMTQSPDSLAVSLGERATINCKSSQSLLDSDGKTYLNWLQQKPGQSPKRLIYLVSKLDSGVPDRFSG
919A  DIVMTQSPDSLAVSLGERATINCKSSQSLLDSDGKTYLNWLQQKPGQPPKRLIYLVSTRESGVPDRFSG
917B  DIVMTQSPDSLAVSLGERATINCKSSQSLLDSDGKTYLNWLQQKPGQPPKRLIYLVSTRESGVPDRFSG
890C  DIVMTQSPDSLAVSLGERATINCKSSQSLLDADGKTYLNWLQQKPGQPPKRLIYWASTRESGVPDRFSG
604C  DIVMTQSPDSLAVSLGERATINCKSSQSLLDSDGKTYLNWLQQKPGQPPKRLIYWASTRESGVPDRFSG
605C  DIVMTQSPDSLAVSLGERATINCKSSQSLLDADGKTYLNWLQQKPGQPPKRLIYWASTRESGVPDRFSG
608C  DIVMTQSPDSLAVSLGERATINCKSSQSLLDSDGKTYLNWLQQKPGQPPKRLIYWASTRESGVPDRFSG
609C  DIVMTQSPDSLAVSLGERATINCKSSQSLLDADGKTYLNWLQQKPGQPPKRLIYWASTRESGVPDRFSG
627C  DIVMTQSPDSLAVSLGERATINCKSSQSLLDSDGKTYLNWLQQKPGQPPKRLIYWASTRESGVPDRFSG

CDR-3
054M  SGSGTDFTLTISSLQAEDVAVYYCWQGTHFPLTFGGGTKVEIK    SEQ ID NO: 84
919A  SGSGTDFTLTISSLQAEDVAVYYCWQGTHFPLTFGGGTKVEIK    SEQ ID NO: 27
917B  SGSGTDFTLTISSLQAEDVAVYYCWQGTWFDLTFGGGTKVEIK    SEQ ID NO: 22
890C  SGSGTDFTLTISSLQAEDVAVYYCWQGTWFDLTFGGGTKVEIK    SEQ ID NO: 20
604C  SGSGTDFTLTISSLQAEDVAVYYCWQGTWFDLTFGGGTKVEIK    SEQ ID NO: 86
605C  SGSGTDFTLTISSLQAEDVAVYYCWQGTWFDLTFGGGTKVEIK    SEQ ID NO: 88
608C  SGSGTDFTLTISSLQAEDVAVYYCWQGTWFDLTFGGGTKVEIK    SEQ ID NO: 21
609C  SGSGTDFTLTISSLQAEDVAVYYCWQGTWFDLTFGGGTKVEIK    SEQ ID NO: 20
627C  SGSGTDFTLTISSLQAEDVAVYYCWQGTWFDLTFGGGTKVEIK    SEQ ID NO: 21
```

FIG. 2B  VH alignment

```
                             *       CDR-1                              CDR-2
054M  EVQLVQSGAEVKKPGESVKVSCKASGFTFTDSYMHWVRQAPGQGLEWMGLIYPFSADTRYAQKFQGRVT
919A  EVQLVQSGAEVKKPGSSVKVSCKASGGTFSDSYMHWVRQAPGQGLEWMGLIYPIFADTRYAQKFQGRVT
917B  EVQLVQSGAEVKKPGSSVKVSCKASGGTFSDSYMHWVRQAPGQGLEWMGLIYPIFADTRYAQKFQGRVT
890C  EVQLVQSGAEVKKPGSSVKVSCKASGGTFSDVYMHWVRQAPGQGLEWMGLIYPIFADTRYAQKFQGRVT
604C  EVQLVQSGAEVKKPGSSVKVSCKASGGTFSDSYMHWVRQAPGQGLEWMGLIYPIFADTRYAQKFQGRVT
605C  EVQLVQSGAEVKKPGSSVKVSCKASGGTFSDSYMHWVRQAPGQGLEWMGLIYPIFADTRYAQKFQGRVT
608C  EVQLVQSGAEVKKPGSSVKVSCKASGGTFSDLYMHWVRQAPGQGLEWMGLIYPIFADTRYAQKFQGRVT
609C  EVQLVQSGAEVKKPGSSVKVSCKASGGTFSDLYMHWVRQAPGQGLEWMGLIYPIFADTRYAQKFQGRVT
627C  EVQLVQSGAEVKKPGSSVKVSCKASGGTFSDVYMHWVRQAPGQGLEWMGLIYPIFADTRYAQKFQGRVT

CDR-3
054M  ITADESTSTAYMELSSLRSEDTAVYYCAIDYDGSFAYWGQGTLVTVSS    SEQ ID NO: 85
919A  ITADESTSTAYMELSSLRSEDTAVYYCAIDYDGSFAYWGQGTLVTVSS    SEQ ID NO: 18
917B  ITADESTSTAYMELSSLRSEDTAVYYCAIDQDGSFAYWGQGTLVTVSS    SEQ ID NO: 19
890C  ITADESTSTAYMELSSLRSEDTAVYYCAIDQDGSFAYWGQGTLVTVSS    SEQ ID NO: 11
604C  ITADESTSTAYMELSSLRSEDTAVYYCAIDQDGSFAYWGQGTLVTVSS    SEQ ID NO: 87
605C  ITADESTSTAYMELSSLRSEDTAVYYCAIDQDGSFAYWGQGTLVTVSS    SEQ ID NO: 89
608C  ITADESTSTAYMELSSLRSEDTAVYYCAIDQDGSFAYWGQGTLVTVSS    SEQ ID NO: 12
609C  ITADESTSTAYMELSSLRSEDTAVYYCAIDQDGSFAYWGQGTLVTVSS    SEQ ID NO: 12
627C  ITADESTSTAYMELSSLRSEDTAVYYCAIDQDGSFAYWGQGTLVTVSS    SEQ ID NO: 11
```

* All CDRs are defined according to Kabat definition, except heavy chain CDR-1, which is defined by AbM

FIG. 7

Summary of predicted immunogenicity profile of V regions of 608C, 609C, 627C, 890C and other anti-PACAP antibodies Tabulated number of immunogenic epitopes across all tested alleles based on stability index of the MHC class II-peptide complex

| | DRB1*01:01 | DRB1*15:01 | DRB1*03:01 | DRB1*04:01 | DRB1*13:01 | DRB1*11:01 | DRB1*07:01 | DRB1*08:01 | DRB1*04:05 | DRB1*09:01 | DRB1*10:01 | DRB1*11:04 | DRB1*15:02 | DRB1*16:02 | DRB1*16:01 |
|---|---|---|---|---|---|---|---|---|---|---|---|---|---|---|---|
| 608C | 0 | 0 | 0 | 0 | 0 | 0 | 0 | 0 | 0 | 0 | 0 | 0 | 0 | 0 | 0 |
| 609C | 0 | 0 | 0 | 0 | 0 | 0 | 0 | 0 | 0 | 0 | 0 | 0 | 0 | 0 | 0 |
| 627C | 0 | 0 | 0 | 0 | 0 | 0 | 0 | 0 | 0 | 0 | 0 | 0 | 0 | 0 | 0 |
| 890C | 0 | 0 | 0 | 0 | 0 | 0 | 0 | 0 | 0 | 0 | 0 | 0 | 0 | 0 | 0 |
| Ab10.H3 | 4 | 1 | 0 | 2 | 1 | 0 | 3 | 1 | 3 | 2 | 2 | 0 | 1 | 2 | 0 |
| Ab1.H | 1 | 1 | 0 | 2 | 0 | 0 | 3 | 0 | 1 | 4 | 1 | 0 | 0 | 0 | 0 |
| Ab B | 1 | 0 | 0 | 1 | 1 | 0 | 1 | 0 | 0 | 2 | 4 | 0 | 0 | 0 | 0 |
| Ab C | 1 | 0 | 0 | 1 | 1 | 0 | 1 | 0 | 0 | 1 | 3 | 0 | 0 | 0 | 0 |
| Ab D | 1 | 0 | 0 | 1 | 2 | 0 | 1 | 0 | 0 | 1 | 3 | 0 | 0 | 0 | 0 |

FIG. 8

| Heavy Chain (SEQ) | SEQ ID NO: 70 | | | | |
|---|---|---|---|---|---|
| 1 | EVQLVQSGAE | VKKPGSSVKV | SCKASGGTFS | DVYMHWVRQA | PGQGLEWMGL | 50 |
| 51 | IYPIFADTRY | AQKFQGRVTI | TADESTSTAY | MELSSLRSED | TAVYYCAIDQ | 100 |
| 101 | DGSFAYWGQG | TLVTVSSAST | KGPSVFPLAP | CSRSTSESTA | ALGCLVKDYF | 150 |
| 151 | PEPVTVSWNS | GALTSGVHTF | PAVLQSSGLY | SLSSVVTVPS | SNFGTQTYTC | 200 |
| 201 | NVDHKPSNTK | VDKTVERKCC | VECPPCPAPP | VAGPSVFLFP | PKPKDTLMIS | 250 |
| 251 | RTPEVTCVVV | DVSHEDPEVQ | FNWYVDGVEV | HNAKTKPREE | QFNSTFRVVS | 300 |
| 301 | VLTVVHQDWL | NGKEYKCKVS | NKGLPSSIEK | TISKTKGQPR | EPQVYTLPPS | 350 |
| 351 | REEMTKNQVS | LTCLVKGFYP | SDIAVEWESN | GQPENNYKTT | PPMLDSDGSF | 400 |
| 401 | FLYSKLTVDK | SRWQQGNVFS | CSVMHEALHN | HYTQKSLSLS | PG* | 442 |
| Light Chain (SEQ) | SEQ ID NO: 71 | | | | |
| 1 | DIVMTQSPDS | LAVSLGERAT | INCKSSQSLL | DADGKTYLNW | LQQKPGQPPK | 50 |
| 51 | RLIYWASTRE | SGVPDRFSGS | GSGTDFTLTI | SSLQAEDVAV | YYCWQGTWFD | 100 |
| 101 | LTFGGGTKVE | IKRTVAAPSV | FIFPPSDEQL | KSGTASVVCL | LNNFYPREAK | 150 |
| 151 | VQWKVDNALQ | SGNSQESVTE | QDSKDSTYSL | SSTLTLSKAD | YEKHKVYACE | 200 |
| 201 | VTHQGLSSPV | TKSFNRGEC | | | | 219 |

FIG. 9

| Heavy Chain (ggMG) | SEQ ID NO: 72 | | | | |
|---|---|---|---|---|---|
| 1 | EVQLVQSGAE | VKKPGSSVKV | SCKASGGTFS | DLYMHWVRQA | PGQGLEWMGL | 50 |
| 51 | IYPIFADTRY | AQKFQGRVTI | TADESTSTAY | MELSSLRSED | TAVYYCAIDQ | 100 |
| 101 | DGSFAYWGQG | TLVTVSSAST | KGPSVFPLAP | CSRSTSESTA | ALGCLVKDYF | 150 |
| 151 | PEPVTVSWNS | GALTSGVHTF | PAVLQSSGLY | SLSSVVTVPS | SNFGTQTYTC | 200 |
| 201 | NVDHKPSNTK | VDKTVERKCC | VECPPCPAPP | VAGPSVFLFP | PKPKDTLMIS | 250 |
| 251 | RTPEVTCVVV | DVSHEDPEVQ | FNWYVDGVEV | HNAKTKPREE | QFNSTFRVVS | 300 |
| 301 | VLTVVHQDWL | NGKEYKCKVS | NKGLPSSIEK | TISKTKGQPR | EPQVYTLPPS | 350 |
| 351 | REEMTKNQVS | LTCLVKGFYP | SDIAVEWESN | GQPENNYKTT | PPMLDSDGSF | 400 |
| 401 | FLYSKLTVDK | SRWQQGNVFS | CSVMHEALHN | HYTQKSLSLS | PG* | 442 |
| Light Chain (ggMG) | SEQ ID NO: 73 | | | | |
| 1 | DIVMTQSPDS | LAVSLGERAT | INCKSSQSLL | DSDGKTYLNW | LQQKPGQPPK | 50 |
| 51 | RLIYWASTRE | SGVPDRFSGS | GSGTDFTLTI | SSLQAEDVAV | YYCWQGTWFD | 100 |
| 101 | LTFGGGTKVE | IKRTVAAPSV | FIFPPSDEQL | KSGTASVVCL | LNNFYPREAK | 150 |
| 151 | VQWKVDNALQ | SGNSQESVTE | QDSKDSTYSL | SSTLTLSKAD | YEKHKVYACE | 200 |
| 201 | VTHQGLSSPV | TKSFNRGEC | | | | 219 |

FIG. 10

| Heavy Chain (G2C) | SEQ ID NO: 70 | | | | | |
|---|---|---|---|---|---|---|
| 1 | EVQLVQSGAE | VKKPGSSVKV | SCKASGGTFS | DVYMHWVRQA | PGQGLEWMGL | 50 |
| 51 | IYPIFADTRY | AQKFQGRVTI | TADESTSTAY | MELSSLRSED | TAVYYCAIDQ | 100 |
| 101 | DGSFAYWGQG | TLVTVSSAST | KGPSVFPLAP | CSRSTSESTA | ALGCLVKDYF | 150 |
| 151 | PEPVTVSWNS | GALTSGVHTF | PAVLQSSGLY | SLSSVVTVPS | SNFGTQTYTC | 200 |
| 201 | NVDHKPSNTK | VDKTVERKCC | VECPPCPAPP | VAGPSVFLFP | PKPKDTLMIS | 250 |
| 251 | RTPEVTCVVV | DVSHEDPEVQ | FNWYVDGVEV | HNAKTKPREE | QFNSTFRVVS | 300 |
| 301 | VLTVVHQDWL | NGKEYKCKVS | NKGLPSSIEK | TISKTKGQPR | EPQVYTLPPS | 350 |
| 351 | REEMTKNQVS | LTCLVKGFYP | SDIAVEWESN | GQPENNYKTT | PPMLDSDGSF | 400 |
| 401 | FLYSKLTVDK | SRWQQGNVFS | CSVMHEALHN | HYTQKSLSLS | PG* | 442 |
| Light Chain (G2C) | SEQ ID NO: 73 | | | | | |
| 1 | DIVMTQSPDS | LAVSLGERAT | INCKSSQSLL | DSDGKTYLNW | LQQKPGQPPK | 50 |
| 51 | RLIYWASTRE | SGVPDRFSGS | GSGTDFTLTI | SSLQAEDVAV | YYCWQGTWFD | 100 |
| 101 | LTFGGGTKVE | IKRTVAAPSV | FIFPPSDEQL | KSGTASVVCL | LNNFYPREAK | 150 |
| 151 | VQWKVDNALQ | SGNSQESVTE | QDSKDSTYSL | SSTLTLSKAD | YEKHKVYACE | 200 |
| 201 | VTHQGLSSPV | TKSFNRGEC | | | | 219 |

FIG. 11

| Heavy Chain (60Gs) | SEQ ID NO: 72 | | | | | |
|---|---|---|---|---|---|---|
| 1 | EVQLVQSGAE | VKKPGSSVKV | SCKASGGTFS | DLYMHWVRQA | PGQGLEWMGL | 50 |
| 51 | IYPIFADTRY | AQKFQGRVTI | TADESTSTAY | MELSSLRSED | TAVYYCAIDQ | 100 |
| 101 | DGSFAYWGQG | TLVTVSSAST | KGPSVFPLAP | CSRSTSESTA | ALGCLVKDYF | 150 |
| 151 | PEPVTVSWNS | GALTSGVHTF | PAVLQSSGLY | SLSSVVTVPS | SNFGTQTYTC | 200 |
| 201 | NVDHKPSNTK | VDKTVERKCC | VECPPCPAPP | VAGPSVFLFP | PKPKDTLMIS | 250 |
| 251 | RTPEVTCVVV | DVSHEDPEVQ | FNWYVDGVEV | HNAKTKPREE | QFNSTFRVVS | 300 |
| 301 | VLTVVHQDWL | NGKEYKCKVS | NKGLPSSIEK | TISKTKGQPR | EPQVYTLPPS | 350 |
| 351 | REEMTKNQVS | LTCLVKGFYP | SDIAVEWESN | GQPENNYKTT | PPMLDSDGSF | 400 |
| 401 | FLYSKLTVDK | SRWQQGNVFS | CSVMHEALHN | HYTQKSLSLS | PG* | 442 |
| Light Chain (Gs6) | SEQ ID NO: 71 | | | | | |
| 1 | DIVMTQSPDS | LAVSLGERAT | INCKSSQSLL | DADGKTYLNW | LQQKPGQPPK | 50 |
| 51 | RLIYWASTRE | SGVPDRFSGS | GSGTDFTLTI | SSLQAEDVAV | YYCWQGTWFD | 100 |
| 101 | LTFGGGTKVE | IKRTVAAPSV | FIFPPSDEQL | KSGTASVVCL | LNNFYPREAK | 150 |
| 151 | VQWKVDNALQ | SGNSQESVTE | QDSKDSTYSL | SSTLTLSKAD | YEKHKVYACE | 200 |
| 201 | VTHQGLSSPV | TKSFNRGEC | | | | 219 |

COMPOSITIONS AND METHODS FOR ANTI-PACAP ANTIBODIES

CROSS-REFERENCE TO RELATED APPLICATIONS

This application claims priority to U.S. Provisional Patent Application No. 63/226,875, filed Jul. 29, 2021, the disclosure of which is incorporated by reference herein in its entirety, including any drawings.

INCORPORATION OF THE SEQUENCE LISTING

The instant application contains Sequence Listing which has been submitted electronically in xml format and is hereby incorporated by reference in its entirety. Said xml file, created on Sep. 6, 2024, is named 2024 Sep. 6 Revised-_Sequence_Listing_ST26 035680-502001US and is 92,241 bytes in size.

FIELD

The present disclosure generally relates anti-pituitary adenylate-cyclase-activating polypeptide (PACAP) antibodies, pharmaceutical compositions comprising such antibodies, and methods of producing and using such monoclonal antibodies.

BACKGROUND

Pituitary adenylate cyclase-activating peptide (PACAP) is a neuropeptide implicated in a wide range of functions, such as nociception and in primary headaches. PACAP is a member of the secretin/vasoactive intestinal peptide (VIP)/growth hormone-releasing hormone (GHRH) family. The PACAP/VIP receptors, PAC1, VPAC1, and VPAC2, are present in sensory neurons and in vascular smooth muscle related to the trigeminovascular system. PAC1 receptor binds PACAP with high affinity and has a much lower affinity for VIP. VPAC1 and VPAC2 receptors recognize PACAP and VIP equally well.

PACAP is a multifunctional vasodilatory peptide that exists in two α-amidated active forms, one with 38 amino acids and the other with 27 amino. PACAP38 is the more prevalent active form, representing up to 90% of PACAP forms in mammalian tissues.

To our knowledge today, PACAP, but not VIP, is implicated in conditions such as migraine, cluster headache and post-traumatic stress disorder (PTSD). For example, increased plasma levels of PACAP have been documented in acute migraine attacks and in cluster headache, in accordance with findings in experimental models of trigeminal activation. This suggests that the activation of the trigeminal system may result in elevated venous levels of PACAP, a change that can be reduced when headache is treated. Further, PACAP injection induces either migraine or cluster headache in patients who suffer from these conditions. In addition, PACAP serum level is linked to PTSD diagnoses and severity of symptoms in female patients.

Anti-PACAP antibodies may be useful in treating various conditions, such as migraine, cluster headache, anxiety, and PTSD. However, to date, no antibody targeting PACAP has been approved for therapeutic use. Accordingly, there is a need for anti-PACAP antibodies that are suitable for therapeutic use in humans.

The present disclosure provides anti-PACAP antibodies that solve the problems and meet the needs in the field.

SUMMARY

In at least one embodiment, the present dislocsure provides an anti-pituitary adenylate-cyclase-activating polypeptide (PACAP) antibody, wherein the antibody comprises heavy chain variable region (VH)-CDR1, VH-CDR2, and VH-CDR3 sequences set forth in SEQ ID NO: 9, 2, and 3, respectively; and light chain variable region (VL)-CDR1, VL-CDR2, and VL-CDR3 sequence set forth in SEQ ID NO: 10, 5, and 6, respectively.

In at least one embodiment, the present disclosure provides an anti-PACAP antibody, wherein the antibody or antigen-binding fragment thereof comprises VH-CDR1, VH-CDR2, and VH-CDR3 sequences selected from the group consisting of: a) SEQ ID NO: 1, 2, and 3; respectively; b) SEQ ID NO: 7, 2, and 3; respectively; and c) variant of a)-b) comprising 1, 2, or 3 conservative amino acid substitutions; and wherein the antibody or antigen-binding fragment thereof comprises VL-CDR1, VL-CDR2, and VL-CDR3 sequences selected from the group consisting of: a) SEQ ID NO: 4, 5, and 6; respectively; b) SEQ ID NO: 8, 5, and 6; respectively; and c) variant of d)-e) comprising 1, 2, or 3 conservative amino acid substitutions.

In at least one embodiment, the present disclosure provides an anti-PACAP antibody, wherein the antibody comprises a VH sequence derived from SEQ ID NO: 19, wherein the VH sequence comprises a valine (V) or leucine (L) at residue 32 according to Kabat numbering; and wherein the antibody comprises a VL sequence derived from SEQ ID NO: 22, wherein the VL sequence comprises alanine (A) at residue 27E according to Kabat numbering, and a tryptophan (W), and an alanine (A) at residues 50 and 51, respectively, according to Kabat numbering. In at least one embodiment, the antibody further comprises cysteine-alanine-isoleucine (CAI) in the VH at residues 92-94 according to Kabat numbering.

In at least one embodiment, the antibody comprises the heavy chain and light chain framework region (FR) sequences derived from human gene IGHV1-69*01 and IGKV4-1*01, respectively, and functional variants thereof.

In at least one embodiment, the antibody comprises heavy chain framework region (VHFR)-1, VHFR-2, VHFR-3, and VHFR-4 sequences set forth in SEQ ID NOs: 29-32, respectively; and light chain framework region (VLFR)-1, VLFR-2, VLFR-3, and VLFR-4 sequences set forth in SEQ ID NOs: 33-36, respectively.

In at least one embodiment, the antibody comprises a VH sequence that is about 90%, about 95%, or about 99% identical to a sequence selected from SEQ ID NOs: 11 and 12, and a VL sequence that is about 90%, about 95%, or about 99% identical to a sequence selected from SEQ ID NOs: 20 and 21.

In at least one embodiment, the antibody comprises a VH sequence selected from SEQ ID NOs: 11 and 12 and a VL sequence selected from SEQ ID NOs: 20 and 21.

In at least one embodiment, the present disclosure provides an anti-PACAP antibody, wherein the antibody comprises VH-CDR1, VH-CDR2, and VH-CDR3 sequences and VL-CDR1, VL-CDR2, and VL-CDR3 sequences selected from the group consisting of: a) SEQ ID NO: 1, 2, and 3 and SEQ ID NO: 4, 5, and 6, respectively; b) SEQ ID NO: 7, 2, and 3 and SEQ ID NO: 8, 5, and 6, respectively; c) SEQ ID NO: 1, 2, and 3 and SEQ ID NO: 8, 5, and 6, respectively; and d) SEQ ID NO: 7, 2, and 3 and SEQ ID NO: 4, 5, and 6, respectively.

In at least one embodiment, the antibody comprises a VH sequence and a VL sequence that are about 90%, about 95%, or about 99% identical to a sequence selected from the group consisting of: a) SEQ ID NO: 11 and 20, respectively; b) SEQ ID NO: 12 and 21, respectively; c) SEQ ID NO: 11 and 21, respectively; and d) SEQ ID NO: 12 and 20, respectively.

In at least one embodiment, the antibody comprises a VH sequence and a VL sequence selected from the group consisting of: a) SEQ ID NO: 11 and 20, respectively; b) SEQ ID NO: 12 and 21, respectively; c) SEQ ID NO: 11 and 21, respectively; and d) SEQ ID NO: 12 and 20, respectively.

In at least one embodiment, the antibody comprises a VH sequence of SEQ ID NO: 11 or SEQ ID NO: 12, wherein the VH sequence has Glutamine (Q) instead of Glutamic Acid (E) at residue 1 of SEQ ID NO: 11 or 12.

In at least one embodiment, the antibody comprises a heavy chain constant region sequence selected from the group consisting of SEQ ID NOs: 37-51 or SEQ ID NOs: 76 and a light chain constant region sequence selected from SEQ ID NOs: 23 and 24.

In at least one embodiment, the antibody comprises a heavy chain constant region sequence set forth in SEQ ID NO: 43 and a light chain constant region sequence set forth in SEQ ID NO: 23.

In at least one embodiment, the antibody comprises a heavy chain constant region sequence set forth in SEQ ID NO: 43 and a light chain constant region sequence set forth in SEQ ID NO: 23.

In at least one embodiment, the antibody comprises a heavy chain constant region sequence set forth in SEQ ID NO: 42 and a light chain constant region sequence set forth in SEQ ID NO: 23.

In at least one embodiment, the antibody comprises a heavy chain constant region sequence set forth in SEQ ID NO: 76 and a light chain constant region sequence set forth in SEQ ID NO: 23.

In at least one embodiment, the antibody is human, or humanized. In at least one embodiment, the antibody is a humanized antibody.

In at least one embodiment, the antibody has low or no immunogenicity profile.

In at least one embodiment, the antibody has a humanness score greater than or equal to about 89%.

In at least one embodiment, the antibody has a KD lower than or equal to about $5 \times 10^{-11}$ molar (M) as measured by SPR at 37° C.

In at least one embodiment, the antibody has a KD lower than or equal to about $3 \times 10^{-11}$ molar (M) as measured by SPR at 37° C.

In at least one embodiment, the antibody is an antigen-binding fragment.

In at least one embodiment, the antibody comprises a Fab, Fab', F(ab')2, Fd, single chain Fv or scFv, disulfide linked Fv, V-NAR domain, IgNar, intrabody, IgGACH2, minibody, F(ab')$_3$, tetrabody, triabody, diabody, single-domain antibody, DVD-Ig, Fcab, mAb$^2$, (scFv)2, or scFv-Fc.

In at least one embodiment, the antibody is a full length antibody.

In at least one embodiment, the antibody constant region is an IgG constant region.

In at least one embodiment, the constant region is an IgG1 constant region.

In at least one embodiment, the constant region is an IgG4 constant region.

In at least one embodiment, the constant region comprises a sequence selected from the group consisting of the human IgG1 sequence set forth in SEQ ID NO: 37, the human IgG1 FAB TAG sequence set forth in SEQ ID NO: 38, the human IgG1 KiH Hole sequence set forth in SEG ID NO: 39, the human IgG1 KiH Knob sequence set forth in SEQ ID NO: 40, the human IgG1 (L235A,G237A) sequence set forth in SEQ ID NO: 41, the human IgG1 YTE sequence set forth in SEQ ID NO: 42, the humanIgG1 (L235A, G237A, YTE) sequence set for in SEQ ID NO: 76, the human IgG2DASS sequence set forth in SEQ ID NO: 43, the human IgG4 sequence set forth in SEQ ID NO: 44, the human IgG4 KiH Hole sequence set forth in SEQ ID NO: 45, the human IgG4 KiH Knob sequence set forth in SEQ ID NO: 46, the human IgG4 (L235A,G237A) sequence set forth in SEQ ID NO: 47, the human IgG4 (L235E) sequence set forth in SEQ ID NO: 48, the human IgG4 YTE sequence set forth in SEQ ID NO: 49, the human IgG4 YTE KiH Hole sequence set forth in SEQ ID NO: 50, and the human IgG4 YTE KiH Knob sequence set forth in SEQ ID NO: 51.

In at least one embodiment, the antibody heavy chain is an IgG2 heavy chain. In at least one embodiment, the heavy chain comprises the IgG2DASS sequence set forth in SEQ ID NO: 43.

In at least one embodiment, the antibody light chain is a human kappa light chain.

In at least one embodiment, the antibody light chain is a human lambda light chain.

In at least one embodiment, the antibody comprises a full length heavy chain sequence and a full length light chain sequence that is about 90%, about 95%, or about 99% identical to the sequences selected from the group consisting of: a) SEQ ID NOs: 70 and 71, respectively; b) SEQ ID Nos: 74 and 71, respectively; c) SEQ ID Nos: 75 and 71, respectively; d) SEQ ID NOs: 72 and 73, respectively; e) SEQ ID NOs: 70 and 73, respectively; and f) SEQ ID NOs: 72 and 71, respectively.

In at least one embodiment, the antibody comprises a full length heavy chain sequence and a full length light chain sequence selected from the group consisting of: a) SEQ ID NOs: 70 and 71, respectively; b) SEQ ID Nos: 74 and 71, respectively; c) SEQ ID Nos: 75 and 71, respectively; d) SEQ ID NOs: 72 and 73, respectively; e) SEQ ID NOs: 70 and 73, respectively; and f) SEQ ID NOs: 72 and 71, respectively. In at least one embodiment, the heavy chain sequence has Glutamine (Q) instead of Glutamic Acid (E) at residue 1 of SEQ ID NO: 70, 72, 74, and 75.

In at least one embodiment, the antibody is an antagonist of PACAP.

In at least one embodiment, the antibody specifically binds to PACAP.

In at least one embodiment, the present disclosure provides a nucleic acid encoding the antibody described herein.

In at least one embodiment, the present disclosure provides a vector comprising the nucleic acid described herein.

In at least one embodiment, the present disclosure provides an engineered cell comprising the vector described herein.

In at least one embodiment, the present disclosure provides a method of producing an antibody, the method comprising culturing the engineered cell of the present disclosure under conditions sufficient for the cell to produce the antibody.

In at least one embodiment, the present disclosure provides a pharmaceutical composition comprising the antibody described herein and a pharmaceutically acceptable carrier.

In at least one embodiment, the present disclosure provides a method of treating or preventing a condition in an individual, comprising administering to the individual a therapeutically effective amount of the antibody or the pharmaceutical composition of the present disclosure, wherein the condition is selected from the group consisting of: headache (e.g., migraine, cluster headache, refractory migraine), anxiety, depression, PTSD, comorbid conditions (e.g. anxiety/depression/PTSD) with headache (e.g., migraine, cluster headache, refractory migraine), comorbid anxiety disorders with migraine, complex regional pain syndrome, and rosacea. In at least one embodiment, the headache is selected from the group consisting of: migraine with aura, migraine without aura, hemiplegic migraine, cluster headache, migrainous neuralgia, chronic headache, episodic migraine, chronic migraine, medication overuse headache, and tension headache.

In at least one embodiment, the present disclosure provides a method of treating or preventing migraine in an individual, comprising administering to the individual a therapeutically effective amount of the antibody or the pharmaceutical composition of the present disclosure.

In at least one embodiment, the present disclosure provides a method of treating or preventing migraine in an individual, comprising administering to the individual a therapeutically effective amount of the antibody or the pharmaceutical composition of the present disclosure, wherein the individual fails to respond to two to four applicable preventive drugs. In at least one embodiment, the individual fails to respond to two to four applicable preventive drugs selected from the group consisting of: divalproex, sodium valproate, valproate, valproic acid, topiramate, gabapentin, propranolol, timolol, atenolol, metoprolol, nadolol, bisopropol, flunarizine, amitriptyline, nortriptyline, doxepin, fluoxetine and candesartan.

In at least one embodiment, the present disclosure provides a method of treating or preventing migraine in an individual, comprising administering to the individual a therapeutically effective amount of the antibody or the pharmaceutical composition of the present disclosure, wherein the individual fails to respond to two to four applicable classes of preventive drugs. In at least one embodiment, the classes of preventative drugs are selected from the group consisting of: antiepileptics, beta-blockers, tricyclic antidepressants, calcium channel blockers, angiotensin II receptor antagonist, botulinum toxin and CGRP pathway monoclonal antibodies. In at least one embodiment, the classes of preventive drugs are selected from a different cluster, wherein the clusters are defined as follows: Cluster A: antiepileptics; Cluster B: beta-blockers; Cluster C: tricyclic antidepressants; Cluster D: calcium channel blockers; Cluster E: angiotensin II receptor antagonists; Cluster F, botulinum toxin, and Cluster G: calcitonin gene related peptide (CGRP) pathway monoclonal antibodies.

In at least one embodiment, the individual fails to respond to two to three, at least two, at least three, at least four, more than two, or more than three preventive drugs or classes of preventive drugs.

In at least one embodiment, the present disclosure provides a method of treating or preventing migraine in an individual, the method comprising: selecting an individual who fails to respond to two to four applicable preventive drugs or classes of preventive drugs; and administering to the individual a therapeutically effective amount of the antibody or the pharmaceutical composition of the present disclosure.

In at least one embodiment, the present disclosure provides a method of treating or preventing migraine in an individual who fails to respond to CGRP pathway monoclonal antibodies, comprising administering to the individual a therapeutically effective amount of the antibody or the pharmaceutical composition of the present disclosure. In at least one embodiment, the CGRP pathway monoclonal antibodies comprises an anti-CGRP antibody (i.e., an anti-CGRP ligand antibody), an anti-CGRP-R antibody (i.e., an anti-CGRP receptor antibody), or both. In at least one embodiment, the anti-CGRP antibody is selected from fremanezumab, galcanezumab, eptinezumab, or combinations thereof. In at least one embodiment, the anti-CGRP-R antibody is erenumab.

In at least one embodiment, the present disclosure provides a composition for use in accordance with the present disclosure.

Each of the aspects and embodiments described herein are capable of being used together, unless excluded either explicitly or clearly from the context of the embodiment or aspect.

BRIEF DESCRIPTION OF THE DRAWINGS/FIGURES

FIG. 1 shows the alignment of human PACAP38, PACAP27, and VIP polypeptide sequences. '*'-denotes fully conserved residue. '.'-denotes conservation between residues of weakly similar properties, ':'-denotes conservation of residues of strongly similar properties.

FIGS. 2A-2B show the VL (FIG. 2A) and VH (FIG. 2B) sequence alignments of some exemplary antibodies provided herein. CDRs are defined according to Kabat numbering, except heavy chain CDR-1, which is defined by AbM in FIG. 2B.

FIG. 7 shows summary of predicted immunogenicity profile of variable regions of 608C, 609C, 627C, 890C and other anti-PACAP antibodies.

Figure 3A:
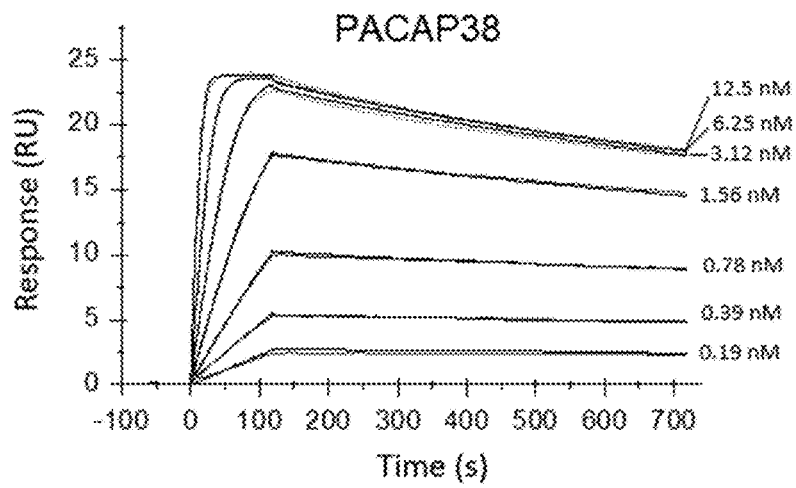
FIGS. 3A-3C show exemplary results of binding affinity of anti-PACAP antibody 605C to PACAP38 and PACAP27 and VIP as measured by SPR at 37° C.

FIG. 8 shows anti-PACAP antibody 890C amino acid sequences. CDRs are underlined (all CDRs defined according to Kabat definition, except heavy chain CDR-1 is defined by AbM). The constant regions are dot-underlined. A330S and P331S substitutions on heavy chain constant region (EU Fc numbering) are double underlined. Deletion of C-terminal Lysine (Δ447K; EU Fc numbering) is marked by an asterisk.

FIG. 9 shows anti-PACAP antibody 608C amino acid sequences. CDRs are underlined (all CDRs defined according to Kabat definition, except heavy chain CDR-1 is defined by AbM). The constant regions are dot-underlined. A330S and P331S substitutions on heavy chain constant region (EU Fc numbering) are double underlined. Deletion of C-terminal Lysine (Δ447K; EU Fc numbering) is marked by an asterisk.

FIG. 10 shows anti-PACAP antibody 627C amino acid sequences. CDRs are underlined (all CDRs defined according to Kabat definition, except heavy chain CDR-1 is defined by AbM). The constant regions are dot-underlined. A330S and P331S substitutions on heavy chain constant region (EU Fc numbering) are double underlined. Deletion of C-terminal Lysine (Δ447K; EU Fc numbering) is marked by an asterisk.

FIG. 11 shows anti-PACAP antibody 609C amino acid sequences. CDRs are underlined (all CDRs defined according to Kabat definition, except heavy chain CDR-1 is defined by AbM). The constant regions are dot-underlined. A330S and P331S substitutions on heavy chain constant region (EU Fc numbering) are double underlined. Deletion of C-terminal Lysine (A447K; EU Fc numbering) is marked by an asterisk.

DETAILED DESCRIPTION

The present disclosure relates to anti-pituitary adenylate-cyclase-activating polypeptide (PACAP) antibodies, in particular, to antibodies having high affinity for PACAP and low immunogenicity when administered to humans. In humans, PACAP is produced from a 176 amino acid precursor protein encoded by the ADCYAP1 gene. There are two naturally-occurring isoforms of PACAP: a 38-amino acid peptide (PACAP38) and a 27-amino acid peptide (PACAP27). PACAP38 corresponds to amino acids 132-169 of the precursor protein and its sequence is HSDGIFTDSYS-RYRKQMAVKKYLAAVLGKRYKQRVKNK (SEQ ID NO: 13). PACAP27 is an amino-terminal fragment of PACAP38 and corresponds to amino acids 132-158 of the precursor protein. The sequence of PACAP27 is HSD-GIFTDSYSRYRKQMAVKKYLAAVL (SEQ ID NO: 14). Both PACAP38 and PACAP27 show high sequence similarity to vasoactive intestinal peptide (VIP), of which the sequence is HSDAVFTDNYTRLRKQMAVKKYLNSILN (SEQ ID NO: 15). See FIG. 1. In some embodiments, the anti-PACAP antibodies provided herein can bind to both PACAP38 and PACAP27 with high affinity. In other embodiments, the antibodies provided herein have low or no binding to VIP.

The disclosure also provides compositions and methods useful for producing such antibodies, nucleic acids encoding same, cells genetically modified with the nucleic acids, as well as methods for the treatment or prevention of various health conditions such as migraine, refractory migraine, etc.

In the following detailed description, reference is made to the accompanying drawings, which form a part hereof. In the drawings, similar symbols generally identify similar components, unless context dictates otherwise. The illustrative alternatives described in the detailed description, drawings, and claims are not meant to be limiting. Other alternatives may be used and other changes may be made without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Definitions

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

"Binding affinity" generally refers to the strength of the sum total of noncovalent interactions between a single binding site of a molecule (e.g., an antibody) and its binding partner (e.g., an antigen/target). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure, an example of which is an affinity ELISA assay. In addition, affinity can be determined by a surface plasmon resonance assay (SPR, e.g., BIAcore®-based assay). Using this methodology, the association rate constant (ka in $M^{-1}s^{-1}$) and the dissociation rate constant (kd in $s^{-1}$) can be measured. The equilibrium dissociation constant (KD in M) can then be calculated from the ratio of the kinetic rate constants (kd/ka). Binding affinity can be also determined by a kinetic method, such as a Kinetic Exclusion Assay (KinExA) as described in Rathanaswami et al. Analytical Biochemistry, Vol. 373:52-60, 2008. Using a KinExA assay, the equilibrium dissociation constant (KD in M) and the association rate constant (ka in $M^{-1}s^{-1}$) 1) can be measured. The dissociation rate constant (kd in $s^{-1}$) can be calculated from these values KD X ka). Binding affinity can be also determined by an equilibrium/solution method By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D." In specific reference to the antibodies described herein, "specifically binds" means that an antibody binds to PACAP27 and/or PACAP38 more readily than it binds to VIP. In one embodiment, the antibody specifically binds to human PACAP. For example: antibody which bind to PACAP27 and PACAP38 more readily than it binds to VIP.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

The term "derived from" as used herein in reference to a protein or polypeptide refers to an origin or source, and may include naturally occurring, recombinant, unpurified or purified polypeptide that is obtained from, is obtained based on a source or original protein or polypeptide. As such, a protein or polypeptide derived from an original protein or polypeptide may include the original protein or polypeptide, in part or in whole, and may be a fragment or variant of the original protein or polypeptide. In some instance, the polypeptide sequence or domain that is derived from a source or origin can be genetically or chemically modified.

The terms "administer", "administration", "administering" and the like, as used herein, refer to the delivery of a composition or formulation or a drug, e.g., an anti-PACAP antibody as disclosed herein by an administration route including, but not limited to, intravenous, intra-arterial, intracranial, intramuscular, intraperitoneal, subcutaneous, intramuscular, or combinations thereof. The term includes, but is not limited to, administration by a medical professional and self-administration.

As used herein, "treatment", "treating," and "to treat" means that at least one or more symptoms improves, even if not at all necessarily do. For example, these terms refer to utilizing an approach for obtaining beneficial or desired clinical results, including but not limited to an approach that achieves such beneficial or desired clinical results, wherein clinical results can include therapeutic measures that improve, cure, slow down, lessen symptoms of, and/or halt progression of a pathologic condition or disorder. Those in need of treatment can include those already diagnosed with or suspected of having the disorder. As used herein, and unless otherwise specified, a "therapeutically effective amount" of an agent or a drug, e.g., an anti-PACAP antibody as disclosed herein in an amount sufficient to provide a therapeutic benefit in the treatment or management of a disease or disorder in a subject, or to delay or minimize one or more symptoms associated with the disease. A therapeutically effective amount of a compound, an agent or a drug means an amount of therapeutic agent, alone or in combination with other therapeutic agents, which provides a therapeutic benefit in the treatment or management of the disease. The term "therapeutically effective amount" can encompass an amount that improves overall therapy of the disease, reduces or avoids symptoms or causes of the disease, or enhances the therapeutic efficacy of another therapeutic agent. An example of an "effective amount" is an amount sufficient to contribute to the treatment, prevention, or reduction of a symptom or symptoms of a disease, which could also be referred to as a "therapeutically effective amount." The exact amount of a composition including a "therapeutically effective amount" will depend on the purpose of the treatment, and will be ascertainable by one skilled in the art using known techniques.

As used herein, a "subject" or an "individual" includes animals, such as human (e.g., human individuals) and non-human animals. In some embodiments, a "subject" or "individual" is a patient under the care of a physician. Thus, the subject can be a human patient who has, is at risk of having, or is suspected of having a disease of interest (e.g., migraine, refractory migraine, etc.) and/or one or more symptoms of the disease. The subject can also be an individual who is diagnosed with a risk of the condition of interest at the time of diagnosis or later. For example, the subject can be further characterized as being at risk of developing a condition described herein, or condition that would benefit from a reduction in PACAP activity.

The terms "cell", "cell culture", "cell line" refer not only to the particular subject cell, cell culture, or cell line but also to the progeny or potential progeny of such a cell, cell culture, or cell line, without regard to the number of transfers or passages in culture. It should be understood that not all progeny are exactly identical to the parental cell. This is because certain modifications may occur in succeeding generations due to either mutation (e.g., deliberate or inadvertent mutations) or environmental influences (e.g., methylation or other epigenetic modifications), such that progeny may not, in fact, be identical to the parent cell, but are still included within the scope of the term as used herein, so long as the progeny retain the same functionality as that of the originally cell, cell culture, or cell line.

The term "operably linked", as used herein, denotes a physical or functional linkage between two or more elements, e.g., polypeptide sequences or polynucleotide sequences, which permits them to operate in their intended fashion. For example, the term "operably linked" when used in context of the orthogonal DNA target sequences described herein or the promoter sequence in a nucleic acid construct, or in an engineered response element means that the orthogonal DNA target sequences and the promoters are in-frame and in proper spatial and distance away from a polynucleotide of interest coding for a protein or an RNA to permit the effects of the respective binding by transcription factors or RNA polymerase on transcription.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B."

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

All ranges disclosed herein also encompass any and all possible sub-ranges and combinations of sub-ranges thereof. Any listed range can be recognized as sufficiently describing and enabling the same range being broken down into at least equal halves, thirds, quarters, fifths, tenths, etc. As a non-limiting example, each range discussed herein can be readily broken down into a lower third, middle third and upper third, and so forth. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Compositions

The present disclosure provides, among others, anti-pituitary adenylate-cyclase-activating polypeptide (PACAP) antibodies. The anti-PACAP antibodies provided herein can block PACAP signalling through PACAP receptors (i.e., PAC1) as well as PACAP signaling through the VIP receptors, VPAC1 and VPAC2. In certain embodiments, the anti-PACAP antibodies provided herein have been engineered to improve the percentage human sequence via humanization. Further, the CDR3 sequences of the anti-PACAP antibodies provided herein are engineered to improve affinity, potency, or both. In some embodiments, the anti-PACAP antibodies were engineered to include heavy chain variable region (VH)-CDR3 that has a Glutamine (Q) at residue 96 of SEQ ID NO: 3, according to Kabat numbering. In some embodiments, the anti-PACAP antibodies include light chain variable region (VL)-CDR3 that has a Tryptophan (W) at residue 93 and an Aspartate (D) at residue 95 of SEQ ID NO: 6, according to Kabat numbering. In other embodiments, the anti-PACAP antibodies provided herein can be engineered to remove immunogenicity and reduce manufacture liabilities. Additionally, the anti-PACAP antibodies provided herein are engineered to achieve potent inhibition of PACAP-38 and/or PACAP-27-induced cyclic adenosine monophosphate (cAMP) production, which is described in Example 5 and as previously described by Wang, Li et al. 2004.

As described in greater detail below, the antibodies provided herein exhibit low or no potential risk for immunogenicity when administered to a subject. As used herein, "low or no potential risk for immunogenicity" refers to the inability of a therapeutic antibody to induce the formation of anti-drug antibodies (ADAs) when administered into a subject in adequate amounts. ADAs are immune system generated antibodies against the therapeutic that can reduce the efficacy of the drug, and more importantly they can also cause adverse effects ranging from a rash at the site of injection to a systemic inflammatory reaction that can be fatal. In certain embodiments, the antibodies provided herein exhibit low or no potential risk for immunogenicity when administered to humans. For administration to humans, the lower or no potential risk for immunogenicity can be provided for example by engineering the antibody to have higher humanness score as well as by removing residues which were found to have with higher potential risk for immunogenicity by predictive in-vitro techniques. As used herein, a "humanness score" refers to the percent sequence identify of the antibody to a human germline.

A person of skill in the art would readily appreciate how to calculate the sequence identity between an antibody and a human germline. For example, the anti-PACAP antibodies have high humanness scores, e.g., greater than or equal to about 89%. In addition, the anti-PACAP antibodies have a strong affinity for PACAP. For instance, some anti-PACAP antibodies provided herein have a KD lower than about $5 \times 10^{-11}$ molar (M) as measured by SPR at 37° C. In some embodiments, the anti-PACAP antibodies provided herein have a KD lower than or equal to about $3 \times 10^{-11}$ molar (M) as measured by SPR at 37° C. In some embodiments, the anti-PACAP antibodies preferentially bind to PACAP, including PACAP-38 and PACAP-27.

Antigen-Binding Molecules

An antibody as used herein has its common meaning in the field, and refers to an immunoglobulin molecule that recognizes and specifically binds to an epitope of a target through at least one antigen binding domain within the variable region of the immunoglobulin molecule. The target can be a peptide, e.g., a PACAP peptide. An antibody of this disclosure encompasses full length antibodies (including full length polyclonal antibodies and full length monoclonal antibodies), antigen-binding fragments (such as Fab, Fab', F(ab')2, and Fv fragments), single chain Fv (scFv) mutants, multispecific antibodies such as bispecific antibodies generated from at least two full length antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. In some embodiments, the antibody of the present disclosure is an IgG antibody. In certain embodiments, the antibody of the present disclosure is an IgG2 antibody. In a more certain embodiment, the antibody of the present disclosure is a modified IgG2 comprising the following mutations: A330P331 to S330S331 (amino acid numbering with reference to the wildtype IgG2 sequence, Eur. J. Immunol. (1999) 29:2613-2624). The different classes of immunoglobulins have different and well known subunit structures and three-dimensional configurations.

The antibody of the present disclosure can include one or more variable regions. A variable region of an antibody refers to the variable region of the antibody light chain (VL) or the variable region of the antibody heavy chain (VH), either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948; Chothia & Lesk, 1987, J. Mol. Biol. 196:901-917; Chothia et al., 1989, Nature 342:878-883; Oxford Molecular's AbM antibody modelling software and North numbering convention (North et al., A New Clustering of Antibody CDR Loop Conformations, Journal of Molecular Biology, 406:228-256 (2011))). In addition, combinations of these two approaches are sometimes used in the art to determine CDRs.

In some embodiments, the anti-PACAP antibodies provided herein are full length antibodies. A full length antibody can include a four polypeptide unit consisting of two identical heavy chains and two identical light chains, as described in greater detail below, held together by disulfide bonds. The light chains are generally shorter, with lower molecular weights than the heavy chains. Each polypeptide chain has a constant region and a variable region. The variable region is specific to each particular antibody. The light chain variable region is referred to as VL and the light chain constant region as CL. Similarly, the heavy chain variable region is referred to as VH and the heavy chain constant regions as CH, with CH1, CH2, and CH3 each denoting a different portion of the constant region of the heavy chain. In some embodiments, carbohydrates can be normally attached to the CH2 domains of the heavy chains. Further, a full length antibody can also contain a fragment crystallizable (Fc) region. The Fc region contains only constant regions from the heavy chains (CH2 and CH3). In contrast, the fragment antigen-binding region (Fab) can include both a constant domain and the variable domains of both the heavy and light chains (VH, VL, CH1 and CL). A fragment variable region (Fv) contains only the two variable domains.

As described above, the antibody of the present disclosure can include one or more constant regions. A "constant region" of an antibody is a well-known term in the art and refers to the part of the antibody that is relatively constant in amino acid sequence between different molecules. Typically, the heavy chain constant region is composed of three distinct regions, termed CH1, CH2, and CH3, numbered in the direction from the amino terminal (N-terminal) end to the carboxy terminal (C-terminal) end. A typical light chain only has one constant region, termed CL. The constant region of an antibody determines its particular effector function. One of skill in the art will readily understand the terminology and structural features of constant regions of antibodies.

Further, anti-PACAP antibodies of the present disclosure also include antigen-binding fragments that specifically bind PACAP. An antigen-binding fragment as used herein refers to a portion of a full length antibody. For instance, in some embodiments, an antigen-binding fragment of an antibody as used herein refers to the antigenic determining variable regions of a full length antibody. Examples of antigen-binding fragments include, but are not limited to a Fab, Fab', F(ab')2, Fd, single chain Fv or scFv, disulfide linked Fv, V-NAR domain, IgNar, intrabody, IgGΔCH2, minibody, F(ab')₃, tetrabody, triabody, diabody, single-domain antibody, DVD-Ig, Fcab, mAb², (scFv)2, or scFv-Fc.

In an embodiment, the anti-PACAP antibodies of the present disclosure are blocking antagonist antibodies, which inhibits or reduces biological activity of PACAP. In some embodiments, blocking antibodies or antagonist antibodies substantially or completely inhibit the biological activity of PACAP. The biological activity of PACAP, can be reduced by 10%, 20%, 30%, 50%, 70%, 80%, 90%, 95%, or even 100% comparing to its natural biological activity. The ability of the anti-PACAP antibodies of the present disclosure to antagonize PACAP can be measured, for example, in a cell-based assay which monitors ligand-induced cyclic adenosine monophosphate (cAMP) production. In some embodiments, the anti-PACAP antibodies of the invention antagonise PACAP-induced activation of the human PAC1, VPAC1, and/or VPAC2 receptors. Various assays for assessing activation of PAC1, VPAC1, and/or VPAC2 receptors are known in the art and include cell-based assays measuring ligand-induced calcium mobilization and cAMP production.

An exemplary cell-based cAMP assay is described in Example 5 and as previously described by Wang, Li et al. 2004.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing.

An antibody provided herein can be a monoclonal antibody. A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both full length and full-length monoclonal antibodies as well as antigen-binding fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The antibodies encompassed by the present disclosure can be human, non-human, humanized, murine, chimeric, or resurfaced. In some embodiments, the antibody of the present disclosure can be a humanized antibody. As used herein, a humanized antibody refers to an antibody derived from a monoclonal antibody raised initially in a non-human animal, such as a rodent or rabbit. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent or rabbit variable region for the corresponding regions of a human antibody (see, e.g., U.S. Pat. Nos. 5,585,089, and 5,693,762; Jones et al, 1986, Nature 321:522-525; Riechmann et al, 1988, Nature 332:323-27; and Verhoeyen et al, 1988, Science 239:1534-1536).

In an embodiment, the antibodies of the present disclosure are engineered to contain a heavy/light chain variable framework region that is the product of or derived from the human gene VH: IGHV1-69*01/VK: IGKV4-1*01, respectively, as shown below.

TABLE 1

| | SEQ ID NO. | Sequence |
|---|---|---|
| IGHV1-69*01 | 17 | QVQLVQSGAEVKKPGSSVKVSCKASGGTESSYAISWV RQAPGQGLEWMGGIIPIFGTANYAQKFQGRVTITADE STSTAYMELSSLRSEDTAVYYCAR |
| IGKV4-1*01 | 26 | DIVMTQSPDSLAVSLGERATINCKSSQSVLYSSNNKN YLAWYQQKPGQPPKLLIYWASTRESGVPDRESGSGSG TDFTLTISSLQAEDVAVYYCQQYYSTP |

Examples of variants that are derived from the above human germline can have a heavy chain and/or a light chain variable framework region that comprises at least one amino acid modification from the corresponding heavy chain and/or light chain variable framework region of a corresponding non-human antibody (e.g., a heavy chain variant with the 'CAI' motif at residues 92-94 according to Kabat numbering).

By way of example, sequences of the anti-PACAP antibodies are provided in the Tables below. In some embodiments, the anti-PACAP antibody of the present disclosure comprises combinations of VH and VL CDR sequences provided in Table 2. In some embodiments, all CDRs defined according to Kabat numbering, except VH-CDR1, which is defined by AbM.

TABLE 2

CDR SEQUENCES

| Ab ID | 890C | 608C | 627C | 609C | Consensus |
|---|---|---|---|---|---|
| VH-CDR1 (SEQ ID NO) | GGTFSDVYMH (SEQ ID NO: 1) | GGTFSDLYMH (SEQ ID NO: 7) | GGTFSDVYMH (SEQ ID NO: 1) | GGTFSDLYMH (SEQ ID NO: 7) | GGTFSD*Xa*YMH (SEQ ID NO: 9) |
| VH-CDR2 (SEQ ID NO) | YPIFAD (SEQ ID NO: 2) | YPIFAD (SEQ ID NO: 2) | YPIFAD (SEQ ID NO: 2) | YPIFAD (SEQ ID NO: 2) | YPIFAD (SEQ ID NO: 2) |
| VH-CDR3 (SEQ ID NO) | DQDGSFAY (SEQ ID NO: 3) | DQDGSFAY (SEQ ID NO: 3) | DQDGSFAY (SEQ ID NO: 3) | DQDGSFAY (SEQ ID NO: 3) | DQDGSFAY (SEQ ID NO: 3) |
| VL-CDR1 (SEQ ID NO) | DADGK (SEQ ID NO: 4) | DSDGK (SEQ ID NO: 8) | DSDGK (SEQ ID NO: 8) | DADGK (SEQ ID NO: 4) | D*Xb*DGK (SEQ ID NO: 10) |
| VL-CDR2 (SEQ ID NO) | WASTRES (SEQ ID NO: 5) | WASTRES (SEQ ID NO: 5) | WASTRES (SEQ ID NO: 5) | WASTRES (SEQ ID NO: 5) | WASTRES (SEQ ID NO: 5) |
| VL-CDR3 (SEQ ID NO) | WQGTWEDLT (SEQ ID NO: 6) | WQGTWEDLT (SEQ ID NO: 6) | WQGTWEDLT (SEQ ID NO: 6) | WQGTWEDLT (SEQ ID NO: 6) | WQGTWEDLT (SEQ ID NO: 6) |

In some embodiments, Xa includes V or L; and Xb includes A or S.

In some embodiments, the anti-PACAP antibody of the present disclosure comprises heavy chain variable region (VH)-CDR1, VH-CDR2, and VH-CDR3 sequences set forth in SEQ ID NO: 9, 2, and 3, respectively; and light chain variable region (VL)-CDR1, VL-CDR2, and VL-CDR3 sequence set forth in SEQ ID NO: 10, 5, and 6, respectively.

In some embodiments, the present disclosure provides an anti-PACAP antibody that have the VH-CDR1, VH-CDR2, and VH-CDR3 sequences set forth in SEQ ID NO: 1, 2, and 3; respectively; and variants comprising 1, 2, or 3 conservative amino acid substitutions. In other embodiments, the present disclosure provides an anti-PACAP antibody thereof that have the VH-CDR1, VH-CDR2, and VH-CDR3 sequences set forth in SEQ ID NO: 7, 2, and 3; respectively; and variants comprising 7, 2, or 3 conservative amino acid substitutions.

In some embodiments, the present disclosure provides an anti-PACAP antibody or antigen-binding fragment thereof that have the VL-CDR1, VL-CDR2, and VL-CDR3 sequences set forth in SEQ ID NO: 4, 5, and 6; respectively; and variants comprising 4, 5, or 6 conservative amino acid substitutions. In other embodiments, the present disclosure provides an anti-PACAP antibody that have the VL-CDR1, VL-CDR2, and VL-CDR3 sequences set forth in SEQ ID NO: 8, 5, and 6; respectively; and variants comprising 8, 5, or 6 conservative amino acid substitutions.

In some exemplary embodiments, the present disclosure provides an anti-PACAP antibody that have the VH-CDR1, VH-CDR2, and VH-CDR3 sequences and VL-CDR1, VL-CDR2, and VL-CDR3 sequences set forth in SEQ ID NO: 1, 2, and 3 and SEQ ID NO: 4, 5, and 6, respectively.

In some embodiments, the anti-PACAP antibody of the present disclosure comprises the VH-CDR1, VH-CDR2, and VH-CDR3 sequences and the VL-CDR1, VL-CDR2, and VL-CDR3 sequences set forth in FIG. 8, SEQ ID NO: 1, 2, 3 and SEQ ID NO: 4, 5, 6, respectively. For example, the said CDRs are underlined in FIG. 8 (all CDRs defined according to Kabat definition, except heavy chain CDR-1 is defined by AbM).

In other exemplary embodiments, the present disclosure provides an anti-PACAP antibody that have the VH-CDR1, VH-CDR2, and VH-CDR3 sequences and VL-CDR1, VL-CDR2, and VL-CDR3 sequences set forth in SEQ ID NO: 7, 2, and 3 and SEQ ID NO: 8, 5, and 6, respectively.

In some embodiments, the anti-PACAP antibody of the present disclosure comprises the (VH)-CDR1, VH-CDR2, and VH-CDR3 sequences and the (VL)-CDR1, VL-CDR2, and VL-CDR3 sequences set forth in FIG. 9, SEQ ID NO: 7, 2, 3 and SEQ ID NO: 8, 5, 6, respectively. For example, the said CDRs are underlined in FIG. 9 (all CDRs defined according to Kabat definition, except heavy chain CDR-1 is defined by AbM).

In some exemplary embodiments, the present disclosure provides an anti-PACAP antibody that have the VH-CDR1, VH-CDR2, and VH-CDR3 sequences and VL-CDR1, VL-CDR2, and VL-CDR3 sequences set forth in SEQ ID NO: 1, 2, and 3 and SEQ ID NO: 8, 5, and 6, respectively.

In some embodiments, the anti-PACAP antibody of the present disclosure comprises the (VH)-CDR1, VH-CDR2, and VH-CDR3 sequences and the (VL)-CDR1, VL-CDR2, and VL-CDR3 sequences set forth in FIG. 10, SEQ ID NO: 1, 2, 3 and SEQ ID NO: 8, 5, 6, respectively. For example, the said CDRs are underlined in FIG. 10 (all CDRs defined according to Kabat definition, except heavy chain CDR-1 is defined by AbM).

In yet other exemplary embodiments, the present disclosure provides an anti-PACAP antibody that have the VH-CDR1, VH-CDR2, and VH-CDR3 sequences and VL-CDR1, VL-CDR2, and VL-CDR3 sequences set forth in SEQ ID NO: 7, 2, and 3 and SEQ ID NO: 4, 5, and 6, respectively.

In some embodiments, the anti-PACAP antibody of the present disclosure comprises the (VH)-CDR1, VH-CDR2, and VH-CDR3 sequences and the (VL)-CDR1, VL-CDR2, and VL-CDR3 sequences set forth in FIG. 11, SEQ ID NO: 7, 2, 3 and SEQ ID NO: 4, 5, 6, respectively. For example, the said CDRs are underlined in FIG. 11 (all CDRs defined according to Kabat definition, except heavy chain CDR-1 is defined by AbM).

In some embodiments, the anti-PACAP antibody of the present disclosure comprises combinations of the VH, VL and FR sequences provided in Tables 3-5 below. In some embodiments, the anti-PACAP antibody of the present disclosure comprises the VH sequences that are provided in table 3, wherein the VH sequence has Glutamine (Q) instead of Glutamic Acid (E) at residue 1 of SEQ ID NO: 11, 12, 18 and 19.

TABLE 3

VARIABLE REGION HEAVY CHAIN (VH) SEQUENCES

| Ab ID | SEQ ID NO | VH seq. |
|---|---|---|
| 890C | 11 | EVQLVQSGAEVKKPGSSVKVSCKASGGTFSDVYMHWVRQA PGQGLEWMGLIYPIFADTRYAQKFQGRVTITADESTSTAY MELSSLRSEDTAVYYCAIDQDGSFAYWGQGTLVTVSS |
| 608C | 12 | EVQLVQSGAEVKKPGSSVKVSCKASGGTFSDLYMHWVRQA PGQGLEWMGLIYPIFADTRYAQKFQGRVTITADESTSTAY MELSSLRSEDTAVYYCAIDQDGSFAYWGQGTLVTVSS |
| 627C | 11 | EVQLVQSGAEVKKPGSSVKVSCKASGGTFSDVYMHWVRQA PGQGLEWMGLIYPIFADTRYAQKFQGRVTITADESTSTAY MELSSLRSEDTAVYYCAIDQDGSFAYWGQGTLVTVSS |
| 609C | 12 | EVQLVQSGAEVKKPGSSVKVSCKASGGTFSDLYMHWVRQA PGQGLEWMGLIYPIFADTRYAQKFQGRVTITADESTSTAY MELSSLRSEDTAVYYCAIDQDGSFAYWGQGTLVTVSS |
| 919A | 18 | EVQLVQSGAEVKKPGSSVKVSCKASGGTFSDSYMHWVRQA PGQGLEWMGLIYPIFADTRYAQKFQGRVTITADESTSTAY MELSSLRSEDTAVYYCAIDYDGSFAYWGQGTLVTVSS |
| 917B | 19 | EVQLVQSGAEVKKPGSSVKVSCKASGGTFSDSYMHWVRQA PGQGLEWMGLIYPIFADTRYAQKFQGRVTITADESTSTAY MELSSLRSEDTAVYYCAIDQDGSFAYWGQGTLVTVSS |

TABLE 4

VARIABLE REGION LIGHT CHAIN (VL) SEQUENCES

| Ab ID | SEQ ID NO | VK seq. |
|---|---|---|
| 890C | 20 | DIVMTQSPDSLAVSLGERATINCKSSQSLLDADGKTYLNW LQQKPGQPPKRLIYWASTRESGVPDRESGSGSGTDFTLTI SSLQAEDVAVYYCWQGTWFDLTFGGGTKVEIK |
| 608C | 21 | DIVMTQSPDSLAVSLGERATINCKSSQSLLDSDGKTYLNW LQQKPGQPPKRLIYWASTRESGVPDRESGSGSGTDFTLTI SSLQAEDVAVYYCWQGTWFDLTFGGGTKVEIK |
| 627C | 21 | DIVMTQSPDSLAVSLGERATINCKSSQSLLDSDGKTYLNW LQQKPGQPPKRLIYWASTRESGVPDRESGSGSGTDETLTI SSLQAEDVAVYYCWQGTWEDLTFGGGTKVEIK |
| 609C | 20 | DIVMTQSPDSLAVSLGERATINCKSSQSLLDADGKTYLNW LQQKPGQPPKRLIYWASTRESGVPDRESGSGSGTDFTLTI SSLQAEDVAVYYCWQGTWFDLTFGGGTKVEIK |
| 919A | 27 | DIVMTQSPDSLAVSLGERATINCKSSQSLLDSDGKTYLNW LQQKPGQPPKRLIYLVSTRESGVPDRFSGSGSGTDFTLTI SSLQAEDVAVYYCWQGTHEPLTFGGGTKVEIK |

TABLE 4-continued

VARIABLE REGION LIGHT CHAIN (VL) SEQUENCES

| Ab ID | SEQ ID NO | VK seq. |
|---|---|---|
| 917B | 22 | DIVMTQSPDSLAVSLGERATINCKSSQSLLDSDGKTYLNW LQQKPGQPPKRLIYLVSTRESGVPDRESGSGSGTDETLTI SSLQAEDVAVYYCWQGTWFDLTFGGGTKVEIK |

TABLE 5

FRAMEWORK REGION (FR) SEQUENCES

| FR ID | SEQUENCE | SEQ ID NO |
|---|---|---|
| VRFR-1 | EVQLVQSGAEVKKPGSSVKVSCKAS | 29 |
| VRFR-2 | WVRQAPGQGLEWMGLI | 30 |
| VRER-3 | TRYAQKFQGRVTITADESTSTAYME LSSLRSEDTAVYYCAI | 31 |
| VRER-4 | WGQGTLVTVSS | 32 |
| VLFR-1 | DIVMTQSPDSLAVSLGERATINCKS SQSLL | 33 |
| VLER-2 | TYLNWLQQKPGQPPKRLIY | 34 |
| VLFR-3 | GVPDRFSGSGSGTDFTLTISSLQAE DVAVYYC | 35 |
| VLFR-4 | FGGGTKVEIK | 36 |

Further, the heavy chain and light chain constant region sequences of some exemplary anti-PACAP antibodies provided below in Tables 6-7. The heavy chain of the anti-PACAP antibodies of the present disclosure may comprise a constant region, such as a constant region that is described in Table 6. In some embodiments, the constant region is modified that is immunologically inert, for example several modified constant region are described in Table 6. For example, the modified constant region can be in residues that are listed herein in Table 6, using the EU numbering base on IgG1 sequence (i.e., SEQ ID NO: 37). In some embodiments, the heavy chain constant region of the anti-PACAP antibodies of the present disclosure can be a human heavy chain having a modified constant region of IgG1 as described in Table 6. For example, modified constant region of IgG1 can be any of the following: human IgG1 FAB TAG, human IgG1 KiH Hole, human IgG1 KiH Knob, human IgG1 (L235A, G237A), human IgG1 YTE, human IgG1 (L235A, G237A, YTE) and variants thereof. In some embodiments, the heavy chain constant region of the anti-PACAP antibodies of the present disclosure can be a human heavy chain having a modified constant region of IgG2 as described in Table 6. For example, the modified constant region heavy chain can be a human heavy chain IgG2 constant region comprising the following mutations: A330P331 to S330S331 (amino acid numbering with reference to the wildtype IgG2 sequence, Eur. J. Immunol. (1999) 29:2613-2624), as described in Table 6, SEQ ID: Human IgG2DASS; SEQ ID NO: 43. In some embodiments, the heavy chain constant region of the anti-PACAP antibodies of the present invention can be a human heavy chain having a modified constant region of IgG4 as described in Table 6. For example, modified constant region of IgG4 can be any of the following: human IgG4 KiH Hole, human IgG4 KiH Knob, human IgG4 (L235A, G237A), human IgG4 (L235E), human IgG4 YTE, human IgG4 YTE KiH Hole, human IgG4 YTE KiH Knob, and variant thereof.

In still other embodiments, the constant region can be aglycosylated for N-linked glycosylation. In some embodiments, the constant region can be aglycosylated for N-linked glycosylation by mutating the oligosaccharide attachment residue (such as Asn297) and/or flanking residues that are part of the N-glycosylation recognition sequence in the constant region. In some embodiments, the constant region can be aglycosylated for N-linked glycosylation. The constant region can be aglycosylated for N-linked glycosylation enzymatically or by expression in a glycosylation deficient host cell.

In still other embodiments, the antibody of the present disclosure comprises any of the above constant region, such as a constant region that is described in Table 6, wherein the constant region sequence may further comprise a C-terminal Lysine (K) at position 447 according to EU Fc numbering.

TABLE 6

HEAVY CHAIN CONSTANT REGION SEQUENCES

| Sequence ID | CH Sequence | SEQ ID NO |
|---|---|---|
| Human IgG1 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLSPG | 37 |
| Human IgG1 FAB TAG | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSC | 38 |
| Human IgG1 KiH Hole | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTIS KAKGQPREPQVYTLPPSRDELTKNQVSLSCAVKGFYPSDIAVEWESNGQPENNYK TTPPVLDSDGSFFLVSKLTVDKSRWQQGNVFSCSVMHEALHNHYTQKSLSLSPG | 39 |
| Human IgG1 KiH Knob | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELLGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTIS KAKGQPREPQVYTLPPSRDELTKNQVSLWCLVKGFYPSDIAVEWESNGQPENNYK TTPPVLDSDGSFFLYSKLTVDKSRWQQGNVFSCSVMHEALHNHYTQKSLSLSPG | 40 |
| Human IgG1 (L235A, G237A) | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELAGAPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLSPG | 41 |
| Human IgG1 YTE | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELLGGPSVFLFPPKPKDTLYITREPEVTCVVVDVSHEDPEVKFNWYVDGV EVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLSPG | 42 |
| Human IgG2DASS | ASTKGPSVFPLAPCSRSTSESTAALGCLVKDYFPEPVTVSWNSGALTSGVHTFPA VLQSSGLYSLSSVVTVPSSNFGTQTYTCNVDHKPSNTKVDKTVERKCCVECPPCP APPVAGPSVFLFPPKPKDTLMISRTPEVTCVVVDVSHEDPEVQFNWYVDGVEVHN AKTKPREEQFNSTFRVVSVLTVVHQDWLNGKEYKCKVSNKGLPSSIEKTISKTKG QPREPQVYTLPPSREEMTKNQVSLTCLVKGFYPSDIAVEWESNGQPENNYKTTPP MLDSDGSFFLYSKLTVDKSRWQQGNVFSCSVMHEALHNHYTQKSLSLSPG | 43 |
| Human IgG4 | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFLGGPSVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSIEKTISKAK GQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLG | 44 |
| Human IgG4 KiH Hole | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFLGGPSVFLFPPKPKDTLMISRTPEVTCVVVDVSQEDPEVQENWYVDGVEVH NAKTKPREEQFNSTYRVVSVLTVLHQDWLNGKEYKCKVSNKGLPSSIEKTISKAK GQPREPQVYTLPPSQEEMTKNQVSLSCAVKGFYPSDIAVEWESNGQPENNYKTTP PVLDSDGSFFLVSRLTVDKSRWQEGNVFSCSVMHEALHNHYTQKSLSLSLG | 45 |

TABLE 6-continued

HEAVY CHAIN CONSTANT REGION SEQUENCES

| Sequence ID | CH Sequence | SEQ ID NO |
|---|---|---|
| Human IgG4 KiH Knob | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFLGGPSVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSIEKTISKAK GQPREPQVYTLPPSQEEMTKNQVSLWCLVKGFYPSDIAVEWESNGQPENNYKTTP PVLDSDGSFFLYSRLTVDKSRWQEGNVFSCSVMHEALHNHYTQKSLSLSLG | 46 |
| Human IgG4, (L235A G237A) | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFAGAPSVELFPPKPKDTLMISRTPEVTCVVVDVSQEDPEVQFNWYVDGVEVH NAKTKPREEQFNSTYRVVSVLTVLHQDWLNGKEYKCKVSNKGLPSSIEKTISKAK GQPREPQVYTLPPSQEEMTKNQVSLTCLVKGFYPSDIAVEWESNGQPENNYKTTP PVLDSDGSFFLYSRLTVDKSRWQEGNVESCSVMHEALHNHYTQKSLSLSLG | 47 |
| Human IgG4 (L235E) | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFEGGPSVFLFPPKPKDTLMISRTPEVTCVVVDVSQEDPEVQFNWYVDGVEVH NAKTKPREEQFNSTYRVVSVLTVLHQDWLNGKEYKCKVSNKGLPSSIEKTISKAK GQPREPQVYTLPPSQEEMTKNQVSLTCLVKGFYPSDIAVEWESNGQPENNYKTTP PVLDSDGSFFLYSRLTVDKSRWQEGNVESCSVMHEALHNHYTQKSLSLSLG | 48 |
| Human IgG4 YTE | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFLGGPSVFLFPPKPKDTLYITREPEVTCVVVDVSQEDPEVQENWYVDGVEVH NAKTKPREEQFNSTYRVVSVLTVLHQDWLNGKEYKCKVSNKGLPSSIEKTISKAK GQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLG | 49 |
| Human IgG4 YTE KiH Hole | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFLGGPSVFLFPPKPKDTLYITREPEVTCVVVDVSQEDPEVQFNWYVDGVEVH NAKTKPREEQFNSTYRVVSVLTVLHQDWLNGKEYKCKVSNKGLPSSIEKTISKAK GQPREPQVYTLPPSQEEMTKNQVSLSCAVKGFYPSDIAVEWESNGQPENNYKTTP PVLDSDGSFFLVSRLTVDKSRWQEGNVESCSVMHEALHNHYTQKSLSLSLG | 50 |
| Human IgG4 YTE KiH Knob | ASTKGPSVFPLAPCSRSTSESTAALGCLVKDYFPEPVTVSWNSGALTSGVHTFPA VLQSSGLYSLSSVVTVPSSSLGTKTYTCNVDHKPSNTKVDKRVESKYGPPCPPCP APEFLGGPSVELFPPKPKDTLYITREPEVTCVVVDVSQEDPEVQFNWYVDGVEVH NAKTKPREEQFNSTYRVVSVLTVLHQDWLNGKEYKCKVSNKGLPSSIEKTISKAK GQPREPQVYTLPPSQEEMTKNQVSLWCLVKGFYPSDIAVEWESNGQPENNYKTTP PVLDSDGSFFLYSRLTVDKSRWQEGNVFSCSVMHEALHNHYTQKSLSLSLG | 51 |
| Human IgG1 (L235A, G237A), YTE | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCDKTHTCP PCPAPELAGAPSVELFPPKPKDTLYITREPEVTCVVVDVSHEDPEVKFNWYVDGV EVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYK TTPPVLDSDGSFFLYSKLTVDKSRWQQGNVFSCSVMHEALHNHYTQKSLSLSPG | 76 |

TABLE 7

LIGHT CHAIN CONSTANT REGION SEQUENCES

| Sequence ID | CH Sequence | SEQ ID NO |
|---|---|---|
| Human kappa | RTVAAPSVFIFPPSDEQLKSGTASVVCLLNNFY PREAKVQWKVDNALQSGNSQESVTEQDSKDSTY SLSSTLTLSKADYEKHKVYACEVTHQGLSSPVT KSENRGEC | 23 |
| Human lambda | GQPKAAPSVTLFPPSSEELQANKATLVCLISDF YPGAVTVAWKADSSPVKAGVETTTPSKQSNNKY AASSYLSLTPEQWKSHRSYSCQVTHEGSTVEKT VAPTECS | 24 |

In some embodiments, the anti-PACAP antibody of the present disclosure comprises heavy chain framework region (VHFR)-1, VHFR-2, VHFR-3, and VHFR-4 sequences set forth in SEQ ID NOs: 29-32, respectively; and light chain framework region (VLFR)-1, VLFR-2, VLFR-3, and VLFR-4 sequences set forth in SEQ ID NOs: 33-36, respectively.

In some embodiments, the anti-PACAP antibody of the present disclosure comprises a VH sequence that is about 80%, about 85%, about 90%, about 95%, or about 99% identical to a sequence selected from SEQ ID NOs: 11 and 12, and a VL sequence that is about 80%, about 85%, about 90%, about 95%, or about 99% identical to a sequence selected from SEQ ID NOs: 20 and 21. In some embodiments, the anti-PACAP antibody of the present disclosure comprise a VH sequence selected from SEQ ID NOs: 11 and 12 and a VL sequence selected from SEQ ID NOs: 20 and 21.

In some embodiments, the anti-PACAP antibody of the present disclosure comprises a VH sequence and a VL sequence that are about 80%, about 85%, about 90%, about 95%, or about 99% identical to a sequence set forth in SEQ ID NO: 11 and 20, respectively. In other embodiments, the anti-PACAP antibody of the present disclosure comprises a VH sequence and a VL sequence that are about 80%, about 85%, about 90%, about 95%, or about 99% identical to a sequence set forth in SEQ ID NO: 12 and 21, respectively. In some embodiments, the anti-PACAP antibody of the present disclosure comprises a VH sequence and a VL sequence that are about 80%, about 85%, about 90%, about 95%, or about 99% identical to a sequence set forth in SEQ ID NO: 11 and 21, respectively. In other embodiments, the anti-PACAP antibody of the present disclosure comprises a VH sequence and a VL sequence that are about 80%, about 85%, about 90%, about 95%, or about 99% identical to a sequence set forth in SEQ ID NO: 12 and 20, respectively.

In some exemplary embodiments, the anti-PACAP antibody of the present disclosure comprises a VH sequence and a VL sequence set forth in SEQ ID NO: 11 and 20, respectively. In some exemplary embodiments, the anti-PACAP antibody of the present disclosure comprises a VH sequence and a VL sequence set forth in SEQ ID NO: 11 and 20, respectively, wherein the VH sequence has Glutamine (Q) instead of Glutamic Acid (E) at residue 1 of SEQ ID NO: 11.

In some embodiments, the anti-PACAP antibody of the present disclosure comprises the VH and VL amino acid sequences provided in FIG. 8, SEQ ID NO: 11 and SEQ ID NO: 20, respectively. For example, the said VH and VL are bold in FIG. 8.

In other exemplary embodiments, the anti-PACAP antibody of the present disclosure comprises a VH sequence and a VL sequence set forth in SEQ ID NO: 12 and 21, respectively. In other exemplary embodiments, the anti-PACAP antibody of the present disclosure comprises a VH sequence and a VL sequence set forth in SEQ ID NO: 12 and 21, respectively, wherein the VH sequence has Glutamine (Q) instead of Glutamic Acid (E) at residue 1 of SEQ ID NO: 12.

In some embodiments, the anti-PACAP antibody of the present disclosure comprises the VH and VL amino acid sequences provided in FIG. 9, SEQ ID NO: 12 and SEQ ID NO: 21, respectively. For example, the said VH and VL are bold in FIG. 9.

In some exemplary embodiments, the anti-PACAP antibody of the present disclosure comprises a VH sequence and a VL sequence set forth in SEQ ID NO: 11 and 21, respectively. In some exemplary embodiments, the anti-PACAP antibody of the present disclosure comprises a VH sequence and a VL sequence set forth in SEQ ID NO: 11 and 21, respectively, wherein the VH sequence has Glutamine (Q) instead of Glutamic Acid (E) at residue 1 of SEQ ID NO: 11.

In some embodiments, the anti-PACAP antibody of the present disclosure comprises the VH and VL amino acid sequences provided in FIG. 10, SEQ ID NO: 11 and SEQ ID NO: 21, respectively. For example, the said VH and VL are bold in FIG. 10.

In other exemplary embodiments, the anti-PACAP antibody of the present disclosure comprises a VH sequence and a VL sequence set forth in SEQ ID NO: 12 and 20, respectively. In other exemplary embodiments, the anti-PACAP antibody of the present disclosure comprises a VH sequence and a VL sequence set forth in SEQ ID NO: 12 and 20, respectively, wherein the VH sequence has Glutamine (Q) instead of Glutamic Acid (E) at residue 1 of SEQ ID NO: 12.

In some embodiments, the anti-PACAP antibody of the present disclosure comprises the VH and VL amino acid sequences provided in FIG. 11, SEQ ID NO: 12 and SEQ ID NO: 20, respectively. For example, the said VH and VL are bold in FIG. 11.

In some embodiments, the anti-PACAP antibody of the present disclosure comprises a heavy chain constant region sequence selected from the group consisting of SEQ ID NOS: 37-51 and a light chain constant region sequence selected from SEQ ID NOs: 23 and 24. In certain exemplary embodiments, the anti-PACAP antibody of the present disclosure comprises a heavy chain constant region sequence set forth in SEQ ID NO: 43 and a light chain constant region sequence set forth in SEQ ID NO: 23.

The Kabat numbering system is generally used when referring to a residue in the variable region (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The amino acid position numbering as in Kabat, refers to the numbering system used for heavy chain variable regions or light chain variable regions of the compilation of antibodies in Kabat et al., Sequences of Proteins of Immunological Interest, 5th Ed. Public Health Service, National Institutes of Health, Bethesda, Md. (1991According to this system, a heavy chain variable region can include a single amino acid insert (e.g., residue 52a according to Kabat) after residue 52 of H2 and inserted residues (e.g., residues 82a, 82b, and 82c, etc) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia VH-CDR1 loop when numbered using the Kabat numbering convention varies at the VH between positions 32 and 34 depending on the length of the loop (this is because the Kabat numbering scheme places the insertions at VH in position 35A and 35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modelling software.

The residue in VH CDR1 at position 32 (Kabat numbering) is critical for having a low predicted immunogenicity profile. Thus, in some embodiments, the antibodies provided herein include a valine (V) or leucine (L) in VH CDR1 at position 32 (Kabat numbering). In some embodiments, the antibodies provided herein do not have a serine(S) in VH CDR1 at position 32 (Kabat numbering).

Further, in some embodiments, the antibodies provided herein have alanine-isoleucine (AI) in VHFR-3 at positions 93 and 94, respectively (Kabat numbering). In some embodiments, the antibodies provided herein do not have alanine-arginine (AR) in VHFR-3 at positions 93 and 94, respectively (Kabat numbering).

In addition, the VL CDR2 positions 50 and 51 (Kabat numbering) are also critical for low immunogenicity profile of the antibodies provided herein. Thus, in some embodiments, the antibodies provided herein include tryptophan-alanine (WA) at VL CDR2 positions 50 and 51, respectively (Kabat numbering).

In some embodiments, the present disclosure also encompasses anti-PACAP antibodies that contain a VH sequence derived from SEQ ID NO: 19 and a VL sequence derived from SEQ ID NO: 22. In some embodiments, the anti- PACAP antibodies include a VH sequence that has a valine (V) or leucine (L) at residue 32 of SEQ ID NO: 19 according to Kabat numbering; and a VL sequence that has alanine (A) at residue 27E of SEQ ID NO: 22 according to Kabat numbering, and a tryptophan (W), and an alanine (A), at residues 50 and 51 of SEQ ID NO: 22, receptively, according to Kabat numbering. In certain embodiments, the anti-PACAP antibodies provided herein further include a cysteine-alanine-isoleucine (CAI) motif in the VH at residues 92-94 according to Kabat numbering. See FIGS. 2A-2B.

For all antibodies provided herein, the constant and/or variable region numbering can be according to the IMGT® (IMGT®, the international ImMunoGeneTics information System®; Lefranc M P et al., *Nucleic Acids* Res, 27 (1): 209-12 (1999); Ruiz M et al., *Nucleic Acids Res,* 28 (1): 219-21 (2000); Lefranc M P, *Nucleic Acids Res,* 29 (1): 207-9 (2001); Lefranc M P, *Nucleic Acids Res,* 31 (1): 307-10 (2003); Lefranc M P et al., *Dev Comp Immunol,* 29 (3): 185-203 (2005); Kaas Q et al., *Briefings in Functional Genomics & Proteomics,* 6 (4): 253-64 (2007)).

For instance, in some embodiments, the present disclosure further includes anti-PACAP antibodies that include combinations of the VH and VL CDR sequences provided in Table 8 below. In some embodiments, the CDR sequences are based on IMGT numbering.

TABLE 8

| \multicolumn{4}{c}{CDR SEQUENCES BASED ON IMGT DEFINITION} | | | |
|---|---|---|---|
| Ab clone | CDR1 | CDR2 | CDR3 |
| 605C-VH | GGTFSDSY (SEQ ID NO: 61) | IYPIFADT (SEQ ID NO: 52) | AIDQDGSFAY (SEQ ID NO: 55) |
| 890C-VH | GGTFSDVY (SEQ ID NO: 28) | IYPIFADT (SEQ ID NO: 52) | AIDQDGSFAY (SEQ ID NO: 55) |
| 919A-VH | GGTFSDSY (SEQ ID NO: 61) | IYPIFADT (SEQ ID NO: 52) | AIDYDGSFAY (SEQ ID NO: 56) |
| 605/890-VL | QSLLDADGKTY (SEQ ID NO: 62) | WAS (SEQ ID NO: 53) | WQGTWEDLT (SEQ ID NO: 57) |
| 919A-VL | QSLLDSDGKTY (SEQ ID NO: 63) | LVS (SEQ ID NO: 54) | WQGTHEPLT (SEQ ID NO: 58) |

In some embodiments, the anti-PACAP antibodies provided herein include combinations of the VH and VL CDR sequences provided in Table 8, wherein each of the CDR sequences can include 1, 2, or 3 conservative amino acid substitutions.

In some embodiments, the anti-PACAP antibody of the present disclosure comprises heavy chain variable region (VH)-CDR1, VH-CDR2, and VH-CDR3 sequences set forth in SEQ ID NO: 61, 52, and 55, respectively; and light chain variable region (VL)-CDR1, VL-CDR2, and VL-CDR3 sequences set forth in SEQ ID NO: 62, 53, and 57, respectively; and variants comprising 1, 2, or 3 conservative amino acid substitutions.

In some embodiments, the anti-PACAP antibody of the present disclosure comprises heavy chain variable region (VH)-CDR1, VH-CDR2, and VH-CDR3 sequences set forth in SEQ ID NO: 28, 52, and 55, respectively; and light chain variable region (VL)-CDR1, VL-CDR2, and VL-CDR3 sequences set forth in SEQ ID NO: 62, 53, and 57, respectively; and variants comprising 1, 2, or 3 conservative amino acid substitutions.

Further, the anti-PACAP antibody of the present disclosure can also include the FR sequences provided in Table 9 herein and variants as described in greater detail below.

TABLE 9

| \multicolumn{5}{c}{FRAMEWORK REGION SEQUENCES BASED ON IMGT NUMBERING} | | | | |
|---|---|---|---|---|
| Ab clone | FW1 | FW2 | FW3 | FW4 |
| 605C-VH | EVQLVQSGAEVKKP GSSVKVSCKAS (SEQ ID NO: 59) | MHWVRQAPGQGL EWMGL (SEQ ID NO: 64) | RYAQKFQGRVTITADES TSTAYMELSSLRSEDTA VYYC (SEQ ID NO: 68) | WGQGTLVTV SS (SEQ ID NO: 66) |

TABLE 9-continued

FRAMEWORK REGION SEQUENCES BASED ON IMGT NUMBERING

| Ab clone | FW1 | FW2 | FW3 | FW4 |
|---|---|---|---|---|
| 890C-VH | EVQLVQSGAEVKKPGSSVKVSCKAS (SEQ ID NO: 59) | MHWVRQAPGQGLEWMGL (SEQ ID NO: 64) | RYAQKFQGRVTITADESTSTAYMELSSLRSEDTAVYYC (SEQ ID NO: 68) | WGQGTLVTVSS (SEQ ID NO: 66) |
| 919A-VH | EVQLVQSGAEVKKPGSSVKVSCKAS (SEQ ID NO: 59) | MHWVRQAPGQGLEWMGL (SEQ ID NO: 64) | RYAQKFQGRVTITADESTSTAYMELSSLRSEDTAVYYC (SEQ ID NO: 68) | WGQGTLVTVSS (SEQ ID NO: 66) |
| 605/890-VK | DIVMTQSPDSLAVSLGERATINCKSS (SEQ ID NO: 60) | LNWLQQKPGQPPKRLIY (SEQ ID NO: 65) | TRESGVPDRESGSGSGTDFTLTISSLQAEDVAVYYC (SEQ ID NO: 69) | FGGGTKVEIK (SEQ ID NO: 67) |
| 919A-VK | DIVMTQSPDSLAVSLGERATINCKSS (SEQ ID NO: 60) | LNWLQQKPGQPPKRLIY (SEQ ID NO: 65) | TRESGVPDRESGSGSGTDFTLTISSLQAEDVAVYYC (SEQ ID NO: 69) | FGGGTKVEIK (SEQ ID NO: 67) |

For all antibodies provided herein, the constant and/or variable domain numbering can also be according to the "EU numbering system" (Edelman G M et al., Proc Natl Acad Sci USA, 63 (1): 78-85 (1969)). A complete correspondence for the human CH1, hinge, CH2, and CH3 constant regions of IGHG1 can be found at the IMGT® database (IMGT®, the international ImMunoGeneTics information System®; Lefranc M P et al., Nucleic Acids Rev, 27 (1): 209-12 (1999); Ruiz M et al., Nucleic Acids Res, 28 (1): 219-21 (2000); Lefranc M P, Nucleic Acids Res, 29 (1): 207-9 (2001); Lefranc M P, Nucleic Acids Res, 31 (1): 307-10 (2003); Lefranc M P et al., Dev Comp Immunol, 29 (3): 185-203 (2005)); Kaas Q et al., Briefings in Functional Genomics & Proteomics, 6 (4): 253-64 (2007)).

For instance, the human kappa immunoglobulin light chain constant domain (IGKC), numbering can be according to the "EU numbering system" (Edelman G M et al., Proc Natl Acad Sci USA, 63 (1): 78-85 (1969)). A complete correspondence for the human CK domain can be found at IMGT database (IMGT®, the international ImMunoGeneTics information System®; Lefranc M P et al, Nucleic Acids Rev, 27 (1): 209-12 (1999); Ruiz M et al., Nucleic Acids Res, 28 (1); 219-21 (2000); Lefranc M P, Nucleic Acids Res, 29 (1): 207-9 (2001); Lefranc M P, Nucleic Acids Res, 31 (1): 307-10 (2003); Lefranc M P et al., Dev Comp Immunol, 29 (3): 185-203 (2005)); Kaas Q et al., Briefings in Functional Genomics & Proteomics, 6 (4): 253-64 (2007)).

In some embodiments, the anti-PACAP antibody of the present disclosure comprises combinations of the heavy chain and light chain full length sequences provided in Table 10 below. In some embodiments, the anti-PACAP antibody of the present disclosure comprises the heavy chain full length sequences that are provided in table 10, wherein the heavy chain sequence has Glutamine (Q) instead of Glutamic Acid (E) at residue 1 of SEQ ID NO: 70, 72, 74 and 75. In still other embodiments, the antibody of the present disclosure comprises the heavy chain full length sequences that are provided in table 10, wherein the constant region sequence may further comprise a C-terminal Lysine (K) at position 447 according to EU Fc numbering.

TABLE 10

FULL LENGTH SEQUENCES FOR ADDITIONAL ANTIBODIES

| Seq. ID | Sequence | SEQ ID NO |
|---|---|---|
| 890C heavy chain | EVQLVQSGAEVKKPGSSVKVSCKASGGTFSDVYMHWVRQAPGQGL EWMGLIYPIFADTRYAQKFQGRVTITADESTSTAYMELSSLRSED TAVYYCAIDQDGSFAYWGQGTLVTVSSASTKGPSVFPLAPCSRST SESTAALGCLVKDYFPEPVTVSWNSGALTSGVHTFPAVLQSSGLY SLSSVVTVPSSNFGTQTYTCNVDHKPSNTKVDKTVERKCCVECPP CPAPPVAGPSVFLFPPKPKDTLMISRTPEVTCVVVDVSHEDPEVQ FNWYVDGVEVHNAKTKPREEQFNSTFRVVSVLTVVHQDWLNGKEY KCKVSNKGLPSSIEKTISKTKGQPREPQVYTLPPSREEMTKNQVS LTCLVKGFYPSDIAVEWESNGQPENNYKTTPPMLDSDGSFFLYSK LTVDKSRWQQGNVFSCSVMHEALHNHYTQKSLSLSPG | 70 |
| 890C heavy chain with IgG1 (L235A, G237A) and YTE | EVQLVQSGAEVKKPGSSVKVSCKASGGTFSDVYMHWVRQAPGQGL EWMGLIYPIFADTRYAQKFQGRVTITADESTSTAYMELSSLRSED TAVYYCAIDQDGSFAYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKKVEPKSCDKTHT CPPCPAPELAGAPSVELFPPKPKDTLYITREPEVTCVVVDVSHED PEVKENWYVDGVEVHNAKTKPREEQYNSTYRVVSVLTVLHQDWLN | 74 |

TABLE 10-continued

FULL LENGTH SEQUENCES FOR ADDITIONAL ANTIBODIES

| Seq. ID | Sequence | SEQ ID NO |
|---|---|---|
| | GKEYKCKVSNKALPAPIEKTISKAKGQPREPQVYTLPPSRDELTK NQVSLTCLVKGFYPSDIAVEWESNGQPENNYKTTPPVLDSDGSFF LYSKLTVDKSRWQQGNVFSCSVMHEALHNHYTQKSLSLSPG | |
| 890C heavy chain with IgG1 (L235A, G237A) | EVQLVQSGAEVKKPGSSVKVSCKASGGTFSDVYMHWVRQAPGQGL EWMGLIYPIFADTRYAQKFQGRVTITADESTSTAYMELSSLRSED TAVYYCAIDQDGSFAYWGQGTLVTVSSASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKKVEPKSCDKTHT CPPCPAPELAGAPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSRDELTK NQVSLTCLVKGFYPSDIAVEWESNGQPENNYKTTPPVLDSDGSFF LYSKLTVDKSRWQQGNVESCSVMHEALHNHYTQKSLSLSPG | 75 |
| 890C light chain | DIVMTQSPDSLAVSLGERATINCKSSQSLLDADGKTYLNWLQQKP GQPPKRLIYWASTRESGVPDRESGSGSGTDFTLTISSLQAEDVAV YYCWQGTWFDLTFGGGTKVEIKRTVAAPSVFIFPPSDEQLKSGTA SVVCLLNNFYPREAKVQWKVDNALQSGNSQESVTEQDSKDSTYSL SSTLTLSKADYEKHKVYACEVTHQGLSSPVTKSFNRGEC | 71 |
| 608C heavy chain | EVQLVQSGAEVKKPGSSVKVSCKASGGTFSDLYMHWVRQAPGQGL EWMGLIYPIFADTRYAQKFQGRVTITADESTSTAYMELSSLRSED TAVYYCAIDQDGSFAYWGQGTLVTVSSASTKGPSVFPLAPCSRST SESTAALGCLVKDYFPEPVTVSWNSGALTSGVHTFPAVLQSSGLY SLSSVVTVPSSNFGTQTYTCNVDHKPSNTKVDKTVERKCCVECPP CPAPPVAGPSVFLFPPKPKDTLMISRTPEVTCVVVDVSHEDPEVQ FNWYVDGVEVHNAKTKPREEQFNSTFRVVSVLTVVHQDWLNGKEY KCKVSNKGLPSSIEKTISKTKGQPREPQVYTLPPSREEMTKNQVS LTCLVKGFYPSDIAVEWESNGQPENNYKTTPPMLDSDGSFFLYSK LTVDKSRWQQGNVFSCSVMHEALHNHYTQKSLSLSPG | 72 |
| 608C light chain | DIVMTQSPDSLAVSLGERATINCKSSQSLLDSDGKTYLNWLQQKP GQPPKRLIYWASTRESGVPDRFSGSGSGTDFTLTISSLQAEDVAV YYCWQGTWFDLTFGGGTKVEIKRTVAAPSVFIFPPSDEQLKSGTA SVVCLLNNFYPREAKVQWKVDNALQSGNSQESVTEQDSKDSTYSL SSTLTLSKADYEKHKVYACEVTHQGLSSPVTKSFNRGEC | 73 |
| 627C heavy chain | EVQLVQSGAEVKKPGSSVKVSCKASGGTFSDVYMHWVRQAPGQGL EWMGLIYPIFADTRYAQKFQGRVTITADESTSTAYMELSSLRSED TAVYYCAIDQDGSFAYWGQGTLVTVSSASTKGPSVFPLAPCSRST SESTAALGCLVKDYFPEPVTVSWNSGALTSGVHTFPAVLQSSGLY SLSSVVTVPSSNFGTQTYTCNVDHKPSNTKVDKTVERKCCVECPP CPAPPVAGPSVFLFPPKPKDTLMISRTPEVTCVVVDVSHEDPEVQ FNWYVDGVEVHNAKTKPREEQFNSTFRVVSVLTVVHQDWLNGKEY KCKVSNKGLPSSIEKTISKTKGQPREPQVYTLPPSREEMTKNQVS LTCLVKGFYPSDIAVEWESNGQPENNYKTTPPMLDSDGSFFLYSK LTVDKSRWQQGNVFSCSVMHEALHNHYTQKSLSLSPG | 70 |
| 627C light chain | DIVMTQSPDSLAVSLGERATINCKSSQSLLDSDGKTYLNWLQQKP GQPPKRLIYWASTRESGVPDRESGSGSGTDETLTISSLQAEDVAV YYCWQGTWFDLTFGGGTKVEIKRTVAAPSVFIFPPSDEQLKSGTA SVVCLLNNFYPREAKVQWKVDNALQSGNSQESVTEQDSKDSTYSL SSTLTLSKADYEKHKVYACEVTHQGLSSPVTKSFNRGEC | 73 |
| 609C heavy chain | EVQLVQSGAEVKKPGSSVKVSCKASGGTFSDLYMHWVRQAPGQGL EWMGLIYPIFADTRYAQKFQGRVTITADESTSTAYMELSSLRSED TAVYYCAIDQDGSFAYWGQGTLVTVSSASTKGPSVFPLAPCSRST SESTAALGCLVKDYFPEPVTVSWNSGALTSGVHTFPAVLQSSGLY SLSSVVTVPSSNFGTQTYTCNVDHKPSNTKVDKTVERKCCVECPP CPAPPVAGPSVFLFPPKPKDTLMISRTPEVTCVVVDVSHEDPEVQ FNWYVDGVEVHNAKTKPREEQFNSTFRVVSVLTVVHQDWLNGKEY KCKVSNKGLPSSIEKTISKTKGQPREPQVYTLPPSREEMTKNQVS LTCLVKGFYPSDIAVEWESNGQPENNYKTTPPMLDSDGSFFLYSK LTVDKSRWQQGNVFSCSVMHEALHNHYTQKSLSLSPG | 72 |
| 609C light chain | DIVMTQSPDSLAVSLGERATINCKSSQSLLDADGKTYLNWLQQKP GQPPKRLIYWASTRESGVPDRESGSGSGTDETLTISSLQAEDVAV YYCWQGTWFDLTFGGGTKVEIKRTVAAPSVFIFPPSDEQLKSGTA SVVCLLNNFYPREAKVQWKVDNALQSGNSQESVTEQDSKDSTYSL SSTLTLSKADYEKHKVYACEVTHQGLSSPVTKSFNRGEC | 71 |

In some embodiments, the anti-PACAP antibody of the present disclosure comprises a full length heavy chain sequence at least about 80%, about 85%, about 90%, about 95%, about 99% identical to a sequence set forth in SEQ ID NOs: 70, and 72, 74, and 75. In some embodiments, the anti-PACAP antibody of the present disclosure comprises a full length light chain sequence at least about 80%, about 85%, about 90%, about 95%, about 99% identical to a sequence set forth in SEQ ID NOs: 71 and 73.

In some embodiments, the anti-PACAP antibody of the present disclosure comprises a full length heavy chain sequence and a full length light chain sequence that is at least about 80%, about 85%, about 90%, about 95%, about 99% identical to SEQ ID NOs: 70 and 71, respectively.

In some embodiments, the anti-PACAP antibody of the present disclosure comprises a full length heavy chain sequence and a full length light chain sequence that is at least about 80%, about 85%, about 90%, about 95%, about 99% identical to SEQ ID NOs: 74 and 71, respectively.

In some embodiments, the anti-PACAP antibody of the present disclosure comprises a full length heavy chain sequence and a full length light chain sequence that is at least about 80%, about 85%, about 90%, about 95%, about 99% identical to SEQ ID NOs: 75 and 71, respectively.

In some embodiments, the anti-PACAP antibody of the present disclosure comprises a full length heavy chain sequence and a full length light chain sequence that is at least about 80%, about 85%, about 90%, about 95%, about 99% identical to SEQ ID NOs: 72 and 73, respectively.

In some embodiments, the anti-PACAP antibody of the present disclosure comprises a full length heavy chain sequence and a full length light chain sequence that is at least about 80%, about 85%, about 90%, about 95%, about 99% identical to SEQ ID NOs: 70 and 73, respectively.

In some embodiments, the anti-PACAP antibody of the present disclosure comprises a full length heavy chain sequence and a full length light chain sequence that is at least about 80%, about 85%, about 90%, about 95%, about 99% identical to SEQ ID NOs: 72 and 71, respectively.

In some exemplary embodiments, the anti-PACAP antibody of the present disclosure comprises a full length heavy chain sequence and a full length light chain sequence set forth in SEQ ID NOs: 70 and 71, respectively. In some embodiments, the anti-PACAP antibody of the present disclosure comprises the heavy chain and light chain full length amino acid sequences provided in FIG. 8, SEQ ID NO: 70 and SEQ ID NO: 71, respectively. For example, the constant regions are dot-underlined in FIG. 8.

In other exemplary embodiments, the anti-PACAP of the present disclosure comprises a full length heavy chain sequence and a full length light chain sequence set forth in SEQ ID NOs: 72 and 73, respectively. In some embodiments, the anti-PACAP antibody of the present disclosure comprises the heavy chain and light chain full length amino acid sequences provided in FIG. 9, SEQ ID NO: 72 and SEQ ID NO: 73, respectively. For example, the constant regions are dot-underlined in FIG. 9.

In some exemplary embodiments, the anti-PACAP antibody of the present disclosure comprises a full length heavy chain sequence and a full length light chain sequence set forth in SEQ ID NOs: 70 and 73, respectively. In some embodiments, the anti-PACAP antibody of the present disclosure comprises the heavy chain and light chain full length amino acid sequences provided in FIG. 10, SEQ ID NO: 70 and SEQ ID NO: 73, respectively. For example, the constant regions are dot-underlined in FIG. 10.

In yet other exemplary embodiments, the anti-PACAP antibody of the present disclosure comprises a full length heavy chain sequence and a full length light chain sequence set forth in SEQ ID NOs: 72 and 71, respectively. In some embodiments, the anti-PACAP antibody of the present disclosure comprises the heavy chain and light chain full length amino acid sequences provided in FIG. 11, SEQ ID NO: 71 and SEQ ID NO: 72, respectively. For example, the constant regions are dot-underlined in FIG. 11

In some embodiments, the anti-PACAP antibody of the present disclosure comprises the heavy chain full length sequences that are provided herein above, wherein the heavy chain sequence has Glutamine (Q) instead of Glutamic Acid (E) at residue 1 of SEQ ID NO: 70, 72, 74, and 75.

As discussed above, the present disclosure encompasses variants of any of the antibodies or antigen-binding fragments disclosed herein. A "variant" of a polypeptide, such as an immunoglobulin chain (e.g., VH, VL, HC, or LC), refers to a polypeptide comprising an amino acid sequence that is at least about 80-99.9% (e.g., 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein; when the comparison is performed by a BLAST algorithm wherein the parameters of the algorithm are selected to give the largest match between the respective sequences over the entire length of the respective reference sequences.

The term "percent identity" as used herein in the context of two or more nucleic acids or proteins, refers to two or more sequences or subsequences that are the same or have a specified percentage of nucleotides or amino acids that are the same (e.g., 80, 81, 82, 83, 84, 85, 86, 87, 88, 89, 90, 91, 92, 93, 94, 95, 96, 97, 98, 99, 99.5, 99.9%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the complement of a sequence. This definition also includes sequences that have deletions and/or additions, as well as those that have substitutions. Sequence identity can be calculated over a range of amino acids. For example, sequence identity can be calculated over a region that is at least about 20 amino acids or nucleotides in length, or over a region that is $10^{-100}$ amino acids or nucleotides in length, or over the entire length of a given sequence. Sequence identity can be calculated using published techniques and widely available computer programs, such as the GCS program package (Devereux et al, *Nucleic Acids* Res. 12:387, 1984), BLASTP, BLASTN, FASTA (Atschul et al., J Mol Biol 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

"Identity" per se has an art-recognized meaning and can be calculated using published techniques. See, e.g., COMPUTATIONAL MOLECULAR BIOLOGY, Lesk, A.

M., ed., Oxford University Press, New York, (1988); BIOCOMPUTING: INFORMATICS AND GENOME PROJECTS, Smith, D. W., ed., Academic Press, New York, (1993); COMPUTER ANALYSIS OF SEQUENCE DATA, PART I, Griffin, A. M., and Griffin, H.

G., eds., Humana Press, New Jersey, (1994); SEQUENCE ANALYSIS IN MOLECULAR BIOLOGY, von Heinje, G., Academic Press, (1987); and SEQUENCE ANALYSIS PRIMER, Gribskov, M. and Devereux, J., eds., M Stockton Press, New York, (1991).) While there exist a number of methods to measure identity between two polynucleotide or polypeptide sequences, the term "identity" is well known to skilled artisans. (Carillo, H., and Lipton, D., SIAM J. Applied Math. 48:1073 (1988).) Methods commonly employed to determine identity or similarity between two sequences include, but are not limited to, those disclosed in "Guide to Huge Computers," Martin J. Bishop, ed., Academic Press, San Diego, (1994), and Carillo, H., and Lipton, D., SIAM J. Applied Math. 48:1073 (1988). Methods for aligning polynucleotides or polypeptides are codified in computer programs, including the GCG program package (Devereux, J., et al., Nucleic Acids Research 12 (1): 387 (1984)), BLASTP, BLASTN, FASTA (Atschul, S. F. et al., J. Mol. Biol. 215:403 (1990), Bestfit program (Wisconsin Sequence Analysis Package, Version 8 for Unix, Genetics Computer Group, University Research Park, 575 Science Drive, Madison, Wis. 53711 (using the local homology algorithm of Smith and Waterman, Advances in Applied Mathematics 2:482 489 (1981)).

By a polypeptide having an amino acid sequence at least, for example, 95% "identical" to a query amino acid sequence of the present disclosure, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the reference sequence may be inserted, deleted or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence. As a practical matter, whether any particular polypeptide is at least about 80, 81, 82, 83, 84, 85, 86, 87, 88, 89, 90, 91, 92, 93, 94, 95, 96, 97, 98, 99, 99.5, 99.9% identical to a polypeptide sequence of the presence disclosure (e.g., an anti-PACAP antibody provided herein) can be determined using known computer programs.

As a practical matter, whether any particular polypeptide is at least 80, 81, 82, 83, 84, 85, 86, 87, 88, 89, 90, 91, 92, 93, 94, 95, 96, 97, 98, 99, 99.5, 99.9% identical to, for instance, the amino acid sequences shown in any of the Tables 1-10, can be determined conventionally using known computer programs. A preferred method for determining the best overall match between a query sequence (a sequence of the present disclosure) and a reference sequence, also referred to as a global sequence alignment, can be determined using the FASTDB computer program mentioned above. In a sequence alignment the query and reference sequences are both amino acid sequences. The result of said global sequence alignment is in percent identity. In one embodiment of the present disclosure, the parameters used in a FASTDB alignment of amino acid sequences to calculate percent identity are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the reference sequence is shorter than the query sequence due to N- or C-terminal deletions, not because of internal deletions, a manual correction must be made to the results. This is because the FASTDB program does not account for N- and C-terminal truncations of the reference sequence when calculating global percent identity. For reference sequences truncated at the N- and C-termini, relative to the query sequence, the percent identity is corrected by calculating the number of residues of the query sequence that are N- and C-terminal of the reference sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present disclosure. Only residues to the N- and C-terminal of the reference sequence, which are not matched/aligned with the query sequence, are considered for the purposes of manually adjusting the percent identity score. That is, only query residue positions outside the farthest N- and C-terminal residues of the reference sequence.

For example, a 90 amino acid residue reference sequence is aligned with a 100 residue query sequence to determine percent identity. The deletion occurs at the N-terminus of the reference sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue reference sequence is compared with a 100 residue query sequence. This time the deletions are internal deletions so there are no residues at the N- or C-termini of the reference sequence which are not matched/aligned with the query. In this case the percent identity calculated by FASTDB is not manually corrected. Once again, only residue positions outside the N- and C-terminal ends of the reference sequence, as displayed in the FASTDB alignment, which are not matched/aligned with the query sequence are manually corrected.

Within the confines of the disclosed percent identity, the disclosure also relates to substitution variants of disclosed polypeptides of the disclosure. Substitution variants include those polypeptides in which one or more amino acid residues are removed and replaced with alternative residues. In one aspect, while the percent identity as disclosed above relates to the overall sequence of the specific sequence identified, the amino acid residues that are to remain constant and are not subject to variation would be those of the CDRs, and the amino acid residues that framework would be subject to variation. For example, in one specific embodiment, when the anti-PACAP antibody, of the present disclosure comprises at least one VH comprising an amino acid sequence that is at least about 80, 81, 82, 83, 84, 85, 86, 87, 88, 89, 90, 91, 92, 93, 94, 95, 96, 97, 98, 99, 99.5, 99.9% identical to the amino acid sequence of SEQ ID NO: 11, the CDR regions of the VH are to remain constant and the framework regions are permitted to be variable, provided the overall percentage identity of SEQ ID NO: 11 falls within the confines of the embodiment. In one aspect, the variations are substitutions that are conservative in nature; however, the disclosure embraces substitutions that are also nonconservative. Conservative substitutions for the purpose of the present disclosure may be defined as set out in Tables 11-13 below. Amino acids can be classified according to physical properties and contribution to secondary and tertiary protein structure. A conservative substitution is recognized in the art as a substitution of one amino acid for another amino acid that has similar properties. Exemplary conservative substitutions are set out in below.

TABLE 11

CONSERVATIVE SUBSTITUTIONS

| Side Chain Characteristic | Amino Acid |
|---|---|
| Aliphatic | |
| Non-polar | Gly, Ala, Pro, Iso, Leu, Val |
| Polar-uncharged | Cys, Ser, Thr, Met, Asn, Gln |
| Polar-charged | Asp, Glu, Lys, Arg |
| Aromatic | His, Phe, Trp, Tyr |
| Other | Asn, Gln, Asp, Glu |

Alternatively, conservative amino acids can be grouped as described in Lehninger (1975) Biochemistry, Second Edition; Worth Publishers, pp. 71-77, as set forth below.

TABLE 12

CONSERVATIVE SUBSTITUTIONS

| Side Chain Characteristic | Amino Acid |
|---|---|
| Non-polar (hydrophobic) | |
| Aliphatic: | Ala, Leu, Iso, Val, Pro |
| Aromatic: | Phe, Trp |
| Sulfur-containing: | Met |
| Borderline: | Gly |
| Uncharged-polar | |
| Hyroxyl: | Ser, Thr, Tyr |
| Amides: | Asn, Gln |
| Sulfhydryl: | Cys |
| Borderline: | Gly |
| Positively Charged (Basic): | Lys, Arg, His |
| Negatively Charged (Acidic) | Asp, Glu |

And still other alternative, exemplary conservative substitutions are set out below.

TABLE 13

CONSERVATIVE SUBSTITUTIONS

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Nucleic Acids

In discussed above, one aspect of the disclosure relates to recombinant nucleic acids including a nucleic acid sequence that encodes an antibody of the disclosure. In some embodiments, the recombinant nucleic acids of the disclosure can be configured as expression cassettes or vectors containing these nucleic acid molecules operably linked to heterologous nucleic acid sequences such as, for example, regulatory sequences which allow in vivo expression of the antibody in a host cell.

Nucleic acid molecules of the present disclosure can be of any length, including for example, between about 1 Kb and about 50 Kb, e.g., between about 1.2 Kb and about 10 Kb, between about 2 Kb and about 15 Kb, between about 5 Kb and about 20 Kb, between about 10 Kb and about 20 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

Accordingly, in some embodiments, provided herein is a nucleic acid molecule including a nucleotide sequence encoding an antibody of the disclosure. In certain embodiment, the nucleic acid molecule provided herein includes a nucleotide sequence encoding any of the polypeptide sequences disclosed herein, e.g., those described in Tables 1-10. In some embodiments, the nucleotide sequence is incorporated into an expression cassette or an expression vector. It will be understood by the skilled artisan that an expression cassette generally includes a construct of genetic material that contains coding sequences of the antibody or antigen-binding fragment thereof and enough regulatory information to direct proper transcription and/or translation of the coding sequences in a recipient cell, in vivo and/or ex vivo. Generally, the expression cassette can be inserted into a vector for targeting to a desired host cell and/or into an individual. As such, in some embodiments, an expression cassette of the disclosure include a coding sequence for an antibody of the disclosure or an antigen-binding fragment thereof, which is operably linked to expression control elements, such as a promoter, and optionally, any or a combination of other nucleic acid sequences that affect the transcription or translation of the coding sequence.

An expression cassette can be inserted into a plasmid, cosmid, virus, autonomously replicating polynucleotide molecule, phage, as a linear or circular, single-stranded or double-stranded, DNA or RNA polynucleotide molecule, derived from any source, capable of genomic integration or autonomous replication, including a nucleic acid molecule where one or more nucleic acid sequences has been linked in a functionally operative manner, e.g., operably linked.

In some embodiments, the nucleic acid molecule of the disclosure is incorporated into an expression vector. It will be understood by one skilled in the art that the term "vector" generally refers to a recombinant polynucleotide construct designed for transfer between host cells, and that can be used for the purpose of transformation, e.g., the introduction of heterologous DNA into a host cell. As such, in some embodiments, the vector can be a replicon, such as a plasmid, phage, or cosmid, into which another DNA segment can be inserted so as to bring about the replication of the inserted segment. In some embodiments, the expression vector can be an integrating vector.

In some embodiments, the expression vector can be a viral vector. As will be appreciated by one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s). The term viral vector can refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus, which is a genus of retrovirus.

The nucleic acid sequences encoding the antibodies and antigen-binding fragments as disclosed herein can be optimized for expression in the host cell of interest. For example, the G-C content of the sequence can be adjusted to average levels for a given cellular host, as calculated by reference to known genes expressed in the host cell. Methods for codon usage optimization are known in the art. Codon usages within the coding sequence of the antibodies and antigen-binding fragment disclosed herein can be optimized to enhance expression in the host cell, such that about 1%, about 5%, about 10%, about 25%, about 50%, about 75%, or up to 100% of the codons within the coding sequence have been optimized for expression in a particular host cell.

Also provided herein are vectors, plasmids, or viruses containing one or more of the nucleic acid molecules encoding any antibody or an antigen-binding fragment thereof as disclosed herein. The nucleic acid molecules can be contained within a vector that is capable of directing their expression in, for example, a cell that has been transformed/transduced with the vector. Suitable vectors for use in eukaryotic and prokaryotic cells are known in the art and are commercially available, or readily prepared by a skilled artisan. See for example, Sambrook, J., & Russell, D. W. (2012). *Molecular Cloning: A Laboratory Manual* (4th ed.). Cold Spring Harbor, NY: Cold Spring Harbor Laboratory and Sambrook, J., & Russel, D. W. (2001). *Molecular Cloning: A Laboratory Manual* (3rd ed.). Cold Spring Harbor, NY: Cold Spring Harbor Laboratory (jointly referred to herein as "Sambrook"); Ausubel, F. M. (1987). *Current Protocols in Molecular Biology*. New York, NY: Wiley (including supplements through 2014); Bollag, D. M. et al. (1996). *Protein Methods*. New York, NY: Wiley-Liss; Huang, L. et al. (2005). *Nonviral Vectors for Gene Therapy*. San Diego: Academic Press; Kaplitt, M. G. et al. (1995). *Viral Vectors: Gene Therapy and Neuroscience Applications*. San Diego, CA: Academic Press; Lefkovits, I. (1997). *The Immunology Methods Manual: The Comprehensive Sourcebook of Techniques*. San Diego, CA: Academic Press; Doyle, A. et al. (1998). *Cell and Tissue Culture: Laboratory Procedures in Biotechnology*. New York, NY: Wiley; Mullis, K. B., Ferré, F. & Gibbs, R. (1994). *PCR: The Polymerase Chain Reaction*. Boston: Birkhauser Publisher; Greenfield, E. A. (2014). *Antibodies: A Laboratory Manual* (2nd ed.). New York, NY: Cold Spring Harbor Laboratory Press; Beaucage, S. L. et al. (2000). *Current Protocols in Nucleic Acid Chemistry*. New York, NY: Wiley, (including supplements through 2014); and Makrides, S. C. (2003). *Gene Transfer and Expression in Mammalian Cells*. Amsterdam, NL: Elsevier Sciences B.V., the disclosures of which are incorporated herein by reference).

DNA vectors can be introduced into cells, e.g., eukaryotic cells via conventional transformation or transfection techniques. Suitable methods for transforming or transfecting host cells can be found in Sambrook et al. (2012, supra) and other standard molecular biology laboratory manuals, such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

Viral vectors that can be used in the disclosure include, for example, retrovirus vectors, adenovirus vectors, and adeno-associated virus vectors, lentivirus vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

For example, an antibody or an antigen-binding fragment thereof as disclosed herein can be produced in a eukaryotic host, such as a mammalian cells (e.g., COS cells, NIH 3T3 cells, or HeLa cells). These cells are available from many sources, including the American Type Culture Collection (Manassas, VA). In selecting an expression system, it matters only that the components are compatible with one another. Artisans or ordinary skill are able to make such a determination. Furthermore, if guidance is required in selecting an expression system, skilled artisans can consult P. Jones, "Vectors: Cloning Applications", John Wiley and Sons, New York, N.Y., 2009).

The nucleic acid molecules provided can contain naturally occurring sequences, or sequences that differ from those that occur naturally, but, due to the degeneracy of the genetic code, encode the same polypeptide, e.g., antibody. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (e.g., either a sense or an antisense strand).

The nucleic acid molecules are not limited to sequences that encode polypeptides (e.g., antibodies); some or all of the non-coding sequences that lie upstream or downstream from a coding sequence (e.g., the coding sequence of an antibody) can also be included. Those of ordinary skill in the art of molecular biology are familiar with routine procedures for isolating nucleic acid molecules. In the event the nucleic acid molecule is a ribonucleic acid (RNA), molecules can be produced, for example, by in vitro transcription.

Recombinant Cell and Cell Cultures

The nucleic acid of the present disclosure can be introduced into a host cell, such as, for example, a Chinese hamster ovary (CHO) cell, to produce an engineered o recombinant cell containing the nucleic acid molecule. Introduction of the nucleic acid molecules (e.g., DNA or RNA, including mRNA) or vectors of the disclosure into cells can be achieved by methods known to those skilled in the art such as, for example, viral infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery. For example, methods for introduction of heterologous nucleic acid molecules into mammalian cells are known in the art and include dextran-mediated transfection, calcium phosphate precipitation, polybrene-mediated transfection, protoplast fusion, electroporation, encapsulation of the nucleic acid molecule(s) in liposomes, lipid nanoparticle technology, biolistic injection and direct microinjection of the DNA into nuclei. In addition, nucleic acid molecules can be introduced into mammalian cells by viral vectors such as lentivirus or adeno-associated virus. As discussed in greater detail below, in some embodiments, an antibody or antigen-binding fragment thereof of the present disclosure can be introduced to a subject in nucleic acid form (e.g, DNA or RNA, including mRNA), such that the subject's own cells produce the antibody. The present disclosure further provides modifications to nucleotide sequences encoding the anti-CoV-S antibodies described herein that result in increased antibody expression, increased antibody stability, increased nucleic acid (e.g., mRNA) stability, or improved affinity or specificity of the antibodies for the CoV spike protein.

Accordingly, in some embodiments, the nucleic acid molecules can be delivered by viral or non-viral delivery vehicles known in the art. For example, the nucleic acid molecule can be stably integrated in the host genome, or can be episomally replicating, or present in the recombinant host cell as a mini-circle expression vector for transient expression. Accordingly, in some embodiments, the nucleic acid molecule is maintained and replicated in the recombinant host cell as an episomal unit. In some embodiments, the nucleic acid molecule is stably integrated into the genome of the recombinant cell. Stable integration can be achieved using classical random genomic recombination techniques or with more precise techniques such as guide RNA-directed CRISPR/Cas genome editing, or DNA-guided endonuclease genome editing with NgAgo (Natronobacterium gregoryi Argonaute), or TALENs genome editing (transcription activator-like effector nucleases). In some embodiments, the nucleic acid molecule is present in the recombinant host cell as a mini-circle expression vector for transient expression.

The nucleic acid molecules can be encapsulated in a viral capsid or a lipid nanoparticle, or can be delivered by viral or non-viral delivery means and methods known in the art, such as electroporation. For example, introduction of nucleic acids into cells can be achieved by viral transduction. In a non-limiting example, adeno-associated virus (AAV) is engineered to deliver nucleic acids to target cells via viral transduction. Several AAV serotypes have been described, and all of the known serotypes can infect cells from multiple diverse tissue types. AAV is capable of transducing a wide range of species and tissues in vivo with no evidence of toxicity, and it generates relatively mild innate and adaptive immune responses.

Lentiviral-derived vector systems are also useful for nucleic acid delivery and gene therapy via viral transduction. Lentiviral vectors offer several attractive properties as gene-delivery vehicles, including: (i) sustained gene delivery through stable vector integration into host genome; (ii) the capability of infecting both dividing and non-dividing cells; (iii) broad tissue tropisms, including important gene- and cell-therapy-target cell types; (iv) no expression of viral proteins after vector transduction; (v) the ability to deliver complex genetic elements, such as polycistronic or intron-containing sequences; (vi) a potentially safer integration site profile; and (vii) a relatively easy system for vector manipulation and production.

In some embodiments, host cells can be genetically engineered (e.g., transduced or transformed or transfected) with, for example, a vector construct of the present application that can be, for example, a viral vector or a vector for homologous recombination that includes nucleic acid sequences homologous to a portion of the genome of the host cell, or can be an expression vector for the expression of the polypeptides of interest. The antibodies of the present invention may be prepared and purified using known methods. For example, cDNA sequences encoding a HC (for example the amino acid sequence given by SEQ ID NO.70 and a LC (for example, the amino acid sequence given by SEQ ID NO.71) may be cloned and engineered into an expression vector, using known methods. The engineered immunoglobulin expression vector may then be stably transfected into engineered cells.

In some embodiments, the engineered cell is a eukaryotic cell. In some embodiments, the engineered cell is an animal cell. In some embodiments, the animal cell is a vertebrate animal cell or an invertebrate animal cell. In some embodiments, the animal cell is a mammalian cell. In some embodiments, the animal cell is a human cell. In some embodiments, the animal cell is a non-human animal cell. In some embodiments, the engineered cell is a non-human primate cell. In some embodiments, the engineered cell is selected from the group consisting of a baby hamster kidney (BHK) cell, a Chinese hamster ovary cell (CHO cell), an African green monkey kidney cell (Vero cell), a human A549 cell, a human cervix cell, a human CHME5 cell, a human PER.C6 cell, a NSO murine myeloma cell, a human epidermoid larynx cell, a human fibroblast cell, a human HEK-293 cell, a human HeLa cell, a human HepG2 cell, a human HUH-7 cell, a human MRC-5 cell, a human muscle cell, a mouse 3T3 cell, a mouse connective tissue cell, a mouse muscle cell, and a rabbit kidney cell. In some embodiments, the engineered cell is a *Pichia pastoris* cell or a *Saccharomyces cerevisiae* cell, all of which are also suitable for production of the antibodies that are described in the present invention.

In another aspect, provided herein are cell cultures including at least one recombinant cell as disclosed herein, and a culture medium. Generally, the culture medium can be any suitable culture medium for culturing the cells described herein. Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

In some embodiments, the present disclosure provides methods for producing an antibody or antigen-binding fragment thereof as described herein. The method can include culturing the engineered or recombinant cell described herein under conditions sufficient for the cell to produce the antibody or the antigen-binding fragment thereof.

Also provided, in another aspect, are animals including a recombinant nucleic acid or a vector as disclosed herein. In some embodiments, the disclosure provides a transgenic animal that is a non-human animal. In some embodiments, the transgenic animal produces an antibody or antigen-binding fragment as disclosed herein.

The transgenic non-human host animals of the disclosure are prepared using standard methods known in the art for introducing exogenous nucleic acid into the genome of a non-human animal. In some embodiments, the non-human animals of the disclosure are mice. Other animal species suitable for the compositions and methods of the disclosure include animals that are (i) suitable for transgenesis and (ii) capable of rearranging immunoglobulin gene segments to produce an antibody response. Examples of such species include but are not limited to rats, rabbits, chickens, goats, pigs, sheep and cows. Approaches and methods for preparing transgenic non-human animals are known in the art. Exemplary methods include pronuclear microinjection, DNA microinjection, lentiviral vector mediated DNA transfer into early embryos and sperm-mediated transgenesis, adenovirus mediated introduction of DNA into animal sperm (e.g., in pig), retroviral vectors (e.g., avian species), somatic cell nuclear transfer (e.g., in goats). The state of the art in the preparation of transgenic domestic farm animals is reviewed in Niemann, H. et al. (2005) Rev. Sci. Tech. 24:285-298.

In some embodiments, the animal is a vertebrate animal or an invertebrate animal. In some embodiments, the animal is a mammalian subject. In some embodiments, the mammalian animal is a non-human animal. In some embodiments, the transgenic animals of the disclosure can be made using classical random genomic recombination techniques or with more precise techniques such as guide RNA-directed CRISPR/Cas genome editing, or DNA-guided endonuclease genome editing with NgAgo (Natronobacterium gregoryi Argonaute), or TALENs genome editing (transcription activator-like effector nucleases). In some embodiments, the transgenic animals of the disclosure can be made using transgenic microinjection technology and do not require the use of homologous recombination technology and thus are considered to be easier to prepare and select than approaches using homologous recombination.

In another aspect, provided herein are methods for producing an antibody or antigen-binding fragment thereof, wherein the methods include growing (i) a transgenic animal as disclosed herein, or (ii) a recombinant cell as disclosed herein under conditions such that the antibody or antigen-binding fragment is produced.

In some embodiments, the methods for producing an antibody or antigen-binding fragment thereof as described herein further include isolating the produced antibody or antigen-binding fragment from (i) the transgenic animal or (ii) recombinant cell and/or the medium in which the recombinant cell is cultured. In some embodiments, the mammalian animal is a non-human primate. Accordingly, the antibodies or antigen-binding fragments produced by the methods disclosed herein are also within the scope of the disclosure.

Pharmaceutical Compositions

The anti-PACAP antibodies, nucleic acids, of the disclosure can be incorporated into compositions, including pharmaceutical compositions.

In another aspect, the antibodies, nucleic acids, of the disclosure can be incorporated into compositions suitable for various downstream applications, for example, pharmaceutical compositions. Exemplary compositions of the disclosure include pharmaceutical compositions which generally include one or more of the antibodies, nucleic acids, and a pharmaceutically acceptable excipient, e.g., carrier. In some embodiments, the composition is a sterile composition. In some embodiments, the composition is formulated as a vaccine. In some embodiments, the composition further includes an adjuvant.

The pharmaceutical compositions provided herein can be in any form that allows for the composition to be administered to an individual. In some specific embodiments, the pharmaceutical compositions are suitable for human administration. The scope of the present disclosure includes desiccated, e.g., freeze-dried, compositions comprising an anti-CoV-S antigen-binding polypeptides, e.g., antibody or antigen-binding fragment thereof (e.g., of Table 1), or a pharmaceutical composition thereof that includes a pharmaceutically acceptable carrier but substantially lacks water. As used herein, the term "pharmaceutically acceptable" means approved by a regulatory agency of the Federal or a state government or listed in the U.S. Pharmacopeia or other generally recognized pharmacopeiae for use in animals, and more particularly in humans. The carrier can be a diluent, adjuvant, excipient, or vehicle with which the pharmaceutical composition is administered. Saline solutions and aqueous dextrose and glycerol solutions can also be employed as liquid carriers, including injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. In some embodiments, the pharmaceutical composition is sterilely formulated for administration into an individual or an animal (some non-limiting examples include a human, or a mammal). In some embodiments, the individual is a human.

In some embodiments, the pharmaceutical compositions of the present disclosure are formulated to be suitable for the intended route of administration to an individual. For example, the pharmaceutical composition can be formulated to be suitable for parenteral, intraperitoneal, colorectal, intraperitoneal, and intratumoral administration. In some embodiments, the pharmaceutical composition can be formulated for oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal or intra-arterial administration. One of ordinary skilled in the art will appreciate that the formulation should suit the mode of administration.

For example, pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In some embodiments, the composition should be sterile and should be fluid to the extent that easy syringability exists. It can be stabilized under the conditions of manufacture and storage, and can be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be generally to include isotonic agents, for example, sugars, polyalcohols such as mannitol, sorbitol, and/or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above.

METHODS

The present disclosure further provides, among others, methods of treating or preventing a condition, such as those described herein, in an individual. In some embodiments, the present invention can include a method of treating or preventing, any aspect of PACAP-related conditions such as headache, migraine, cluster headache and/or refractory migraine, anxiety, depression, PTSD, comorbid conditions (e.g. anxiety/depression/PTSD) with headache (e.g., migraine, cluster headache, refractory migraine), comorbid anxiety disorders with migraine, complex regional pain syndrome, and rosacea. For example, in the context of headache or migraine treatment, this includes lessening severity, alleviation of pain intensity (for example, headache, i.e., head pain), and other associated symptoms, reducing frequency of recurrence, increasing the quality of life of those suffering from the headache, and decreasing dose of other medications required to treat the headache. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, rhinorrhea or nasal congestion, and red flushed face.

Further provided herein includes a method for reducing symptoms of a condition, such as those described herein, in an individual. A "reduction" of a symptom means decreasing of the severity or frequency of the symptom(s), or elimination of the symptom(s). Thus, as used herein, the terms "reducing incidence," "prophylaxis," or "prevention" means any of reducing severity for a particular disease, condition, symptom, or disorder (the terms disease, condition, and disorder are used interchangeably throughout the application). Reduction in severity includes reducing drugs and/or therapies generally used for the condition by, for example, reducing the need for, amount of, and/or exposure to drugs or therapies. Reduction in severity also includes reducing the duration, and/or frequency of the particular condition, symptom, or disorder (including, for example, delaying or increasing time to next episodic attack in an individual).

Additionally, the present disclosure provides a method of ameliorating a condition, such as those described herein, in an individual. Ameliorating a condition, such as one or more symptoms of headache or migraine, or other PACAP-related condition as described herein, means a lessening or improvement of one or more symptoms of the condition, e.g., headache or migraine, as compared to not administering an anti-PACAP antagonist antibody. Ameliorating can also include shortening or reduction in duration of symptom.

In some embodiments, the present disclosure further provides a method of controlling a condition, such as those described herein, in an individual. As used herein, "controlling headache" or "controlling migraine" or "controlling" another PACAP-related condition refers to maintaining or reducing severity or duration of one or more symptoms of the condition, e.g., headache, migraine, or frequency of headache or migraine attacks in an individual (as compared to the level before treatment). For example, the duration or severity of head pain, or frequency of attacks is reduced by at least about any of 10%, 20%, 30%, 40%, 50%, 60%, 70%, 80%, 90%, or 100% in the individual as compared to the level before treatment. The reduction in the duration or severity of head pain, or frequency of attacks can last for any length of time, e.g., 2 weeks, 4 weeks (1 month), 8 weeks (2 months), 12 weeks (3 months), 4 months, 5 months, 6 months, 9 months, 12 months, etc.

As used therein, "delaying" the development of a condition, e.g., a PACAP-related condition such as migraine or headache, means to defer, hinder, slow, retard, stabilize, and/or postpone progression of the condition or disease. This delay can be of varying lengths of time, depending on the history of the condition or disease and/or individuals being treated. As is evident to one skilled in the art, a sufficient or significant delay can, in effect, encompass prevention, in that the individual does not develop headache (e.g., migraine). A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of a condition, e.g., a PACAP-related condition as described herein, means initial manifestations and/or ensuing progression of the disorder or symptom or side effect of such disorder such as photophobia or light aversion. Development of headache or migraine can be detectable and assessed using standard clinical techniques as well known in the art. However, development also refers to progression that may be undetectable. For purpose of this disclosure, development, or progression refers to the biological course of the symptoms. "Development" includes occurrence, recurrence, and onset. As used herein "onset" or "occurrence" of a condition such as headache or migraine includes initial onset and/or recurrence. The condition can be, for example, primary or secondary headache. Primary headache includes, for example, migraine with aura, migraine without aura, hemiplegic migraines, episodic migraine, chronic migraine, abdominal migraine, cluster headaches, tension headaches, general headaches, paroxysmal hemicrania, and hemicrania continua. Secondary headaches include, for example, headaches due to a disorder of homeostasis such as headache attributed to autonomic dysreflexia, comorbid anxiety disorders with migraine, and complex regional pain syndrome. Additionally, said subject may have a condition selected from the group consisting of migraine, headache and a pain associated disease or condition such as cluster headache and/or refractory migraine, anxiety, depression, PTSD, comorbid conditions (e.g. anxiety/depression/PTSD) with headache (e.g., migraine, cluster headache, refractory migraine), comorbid anxiety disorders with migraine, complex regional pain syndrome, and rosacea. In some embodiments, headache may be selected from the group consisting of migraine with aura, migraine without aura, hemiplegic migraine, cluster headache, migrainous neuralgia, chronic headache, episodic migraine, chronic migraine, medication overuse headache, and tension headache.

In other embodiments, the individual may have a condition not listed here, but is deemed in need of treatment by the antibody or the pharmaceutical composition described herein.

Migraine is a chronic paroxysmal neurological disorder characterised by attacks of moderate or severe headache and reversible neurological and systemic symptoms. The most characteristic symptoms associated with migraine include, without being limited to, photophobia, phonophobia, and gastrointestinal symptoms such as nausea and vomiting. In contrast, headache generally refers to pain in any region of the head. Headaches may occur on one or both sides of the head, be isolated to a certain location, radiate across the head from one point, or have a vise-like quality. A headache may be a sharp pain, throbbing sensation or dull ache. Headaches may appear gradually or suddenly, and they may last less than an hour or for several days.

International Headache Society (IHS) defines migraine as a recurrent headache disorder manifesting in attacks lasting 4-72 hours. Typical characteristics of the headache are unilateral location, pulsating quality, moderate or severe intensity, aggravation by routine physical activity and association with nausea and/or photophobia and phonophobia. (Headache Classification Subcommittee of the International Headache Society (2018). The international classification of headache disorders $3^{rd}$ edition. Cephalalgia 38:1-211). According to Headache Classification Committee of the IHS, Migraine has two major types: 1) migraine without aura, which is a clinical syndrome characterized by headache with specific features and associated symptoms; and 2) migraine with aura, which is primarily characterized by the transient focal neurological symptoms that usually precede or sometimes accompany the headache.

Migraine with aura, also called classical migraine, includes symptoms such as recurrent attacks of unilateral fully reversible visual, sensory or other central nervous system symptoms that usually develop gradually and are usually followed by headache and associated migraine symptoms. These attacks usually last minutes. Migraine can be chronic. Further, chronic migraine can also include episodic subtypes of migraine. Chronic migraine occurs on 15 or more days/month for more than three months, which has the features of migraine headache on at least eight days/month.

In addition, the methods provided herein can be used to treat an individual with cluster headache. The symptoms of a cluster headache include, without limitation, attacks of severe, strictly unilateral pain which is orbital, supraorbital, temporal or in any combination of these sites, lasting 15-180 minutes and occurring from once every other day to eight times a day. The pain is associated with ipsilateral conjunctival injection, lacrimation, nasal congestion, rhinorrhoea, forehead and facial sweating, miosis, ptosis and/or eyelid oedema, and/or with restlessness or agitation.

Cluster headache can be episodic or chronic. Episodic cluster headache can be attacks occurring in periods lasting from seven days to one year, separated by pain-free periods lasting at least three months. For example, episodic cluster headache can manifest as attacks occurring in periods lasting from seven days to one year, separated by pain-free periods lasting at least three months. Further, episodic cluster headache can also manifest as at least two cluster periods lasting from seven days to one year (when untreated) and separated by pain-free remission periods of ≥3 months, according to the international classification of headache disorders, 3rd edition. In contrast, chronic cluster headache can be attacks occurring for one year or longer without remission, or with remission periods lasting less than three months.

The term refractory migraine, or resistant migraine, has been used to describe persistent headache that is difficult to treat or fails to respond to standard and/or aggressive treatments. In some embodiments, a refractory migraine as used herein requires the failure of prior treatment of two to four applicable preventive drugs or classes of preventive drugs. In certain embodiments, a refractory migraine as used herein requires the failure of prior treatment of two to three, at least two, at least three, at least four, more than two, or more than three applicable preventive drugs or classes of preventive drugs.

As used herein, "fails to respond" or "treatment failure" refers to the lack of efficacy of the preventive drugs or classes of preventive drugs in reducing the frequency, duration, and/or severity of migraine headache in the patient following a standard therapeutic regimen of the drug or when treatment (e.g., with the preventive drugs or classes of preventive drugs) has to be interrupted because of adverse events that made it intolerable by the patient or the drug is contraindicated or not suitable for the patient . . .

Preventive drugs can be divided into several classes. For example, these classes include the following clusters: Cluster A, antiepileptics; Cluster B, beta-blockers; Cluster C, tricyclic antidepressants; Cluster D, calcium channel blockers; Cluster E, angiotensin II receptor antagonists; Cluster F, botulinum toxin; and Cluster G, calcitonin gene related peptide (CGRP) pathway monoclonal antibodies. In some embodiments, a refractory migraine as used herein requires the failure of prior treatment of two to four of any of the above described clusters. In certain embodiments, a refractory migraine as used herein requires the failure of prior treatment of two to three, at least two, at least three, at least four, more than two, or more than three of any of the above described clusters.

Exemplary antiepileptics include divalproex, sodium valproate, valproate, valproic acid, topiramate, and gabapentin. Exemplary beta-blockers include propranolol, timolol, atenolol, metoprolol, nadolol, and bisopropol. Exemplary tricyclic antidepressants include amitriptyline, nortriptyline, doxepin, and fluoxetine. An exemplary calcium channel blocker includes flunarizine. An exemplary angiotensin II receptor antagonist includes candesartan. Anti-CGRP pathway monoclonal antibodies are described infra. For instance, the calcitonin gene related peptide (CGRP) pathway monoclonal antibody can comprise an anti-CGRP antibody, an anti-CGRP-receptor (CGRP-R) antibody, or both. In an exemplary embodiment, the anti-CGRP antibody is fremanezumab. In another embodiment, the anti-CGRP antibody is galcanezumab. In one embodiment, the anti-CGRP antibody is eptinezumab. An exemplary, anti-CGRP-R antibody includes erenumab.

In certain embodiments, the applicable preventive drugs for migraine do not include acute treatments. In other embodiments, a refractory migraine as encompassed by the present disclosure require failure of two to four, three to four, at least two, or at least three classes of preventive drugs, as defined by Refractory Headache Special Interest Section (RHSIS) of the American Headache Society (AHS). In some instances under this definition, individuals need to fail 3 classes of preventive treatments.

Additionally, a definition for pharmacologically intractable headache has been proposed by Silberstein SD, et al. (2010). (Defining the pharmacologically intractable headache for clinical trials and clinical practice. Headache 50 (9): 1499-1506.) This definition builds upon the AHS criteria, proposing a graded classification scheme for intractability to acute and preventive treatments as well as rating of headache-related disability. Specifically, this definition proposes Class I (mild) intractable headache as failure of adequate response to 2 different classes of non-specific acute treatments (e.g., non-steroidal anti-inflammatory drug (NSAIDs), combination analgesics); Class II (moderate) intractable headache as Class I plus failure to respond to triptans or ergot derivatives (such as dihydroergotamine (DHE)); and Class III (severe) intractable headache as Classes I and II plus failure to respond to oral or parenteral opioids or corticosteroids or parenteral dopamine antagonists in adequate doses and appropriate formulation.

Further, the European Headache Federation (EHF) provides a consensus statement on the definition of chronic migraine (CM) in 2014. These criteria are restricted to CM and require the failure of three classes of preventive treatments. They also require adequate treatment of psychiatric or other comorbidities by a multidisciplinary team, if available. In some aspects, acute treatments and degree of disability are not included in these criteria. Thus, when referring to a refractory or resistant migraine, this disclosure intends to include all of the above definitions.

In other embodiments, the present disclosure further provides methods of treating or preventing a headache in an individual. In some embodiments, the headache is migraine. In some embodiments, the present disclosure further provides methods of treating or preventing migraine in an individual. In some embodiments, the present disclosure further provides methods of treating or preventing episodic migraine. In some embodiments, the present disclosure further provides methods of treating or preventing chronic migraine. In some embodiments, the headache is cluster headache. In some embodiments, the headache is episodic cluster headache. In some embodiments, the headache is chronic cluster headache. In further embodiments, the present disclosure further provides methods of treating or preventing a refractory or resistant migraine in an individual. In additional embodiments, the present disclosure provides a method of treating an individual diagnosed with migraine who is not responsive to at least two, at least three, two to three, two to four, more than two, more than three, or up to four prior preventative therapies for migraine (i.e., refractory migraine).

In some embodiments, the methods of treat or prevent provided herein include administering to an individual a therapeutically effective amount of the anti-PACAP antibody, or the pharmaceutical composition described herein.

In certain embodiments, the condition to be treated or prevented is migraine or refractory migraine. In other embodiments, the condition to be treated or prevented is episodic migraine. In other embodiments, the condition to be treated or prevented is chronic migraine. In other embodiments, the method can also include administering to the individual a second agent simultaneously or sequentially with the anti-PACAP antibody. The second agent can be for example, an acute treatment for migraine. In yet other embodiments, the second agent can be a preventive treatment for migraine and/or refractory migraine.

Acute treatments for migraine are known in the art and include, non-steroidal anti-inflammatory drugs (NSAID) and/or ergot alkaloids and/or triptans and/or a 5 hydroxytryptamine IF receptor agonist (i.e., ditans), and gepants (i.e., calcitonin gene-related peptide receptor antagonist).

Non-limiting examples of NSAIDs that can be used in combination with anti-PACAP antibody include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib, rofecoxib, meloxicam, JTE-522, L-745, 337, NS398, or a pharmaceutically acceptable salt thereof.

Non-limiting examples of triptans than can be used in combination with an anti-PACAP antibody as described herein include sumatriptan, zolmitriptan, naratriptan, rizatriptan, eletriptan, almotriptan, and afrovatriptan.

A non-limiting example of a ditan than can be used in combination with the anti-PACAP antibody of the present disclosure includes lasmiditan.

Non-limiting examples of gepants that can be used in combination with an anti-PACAP antibody of the present disclosure includes ubrogepant, rimegepant, atogepant, and vazegepant.

Preventive treatments for migraine and/or refractory migraine are known in the field. In one embodiment, the preventive treatment comprises topiramate. In another embodiment, the preventive treatment comprises Onabotulinumtoxin A. In one embodiment, the preventive treatment comprises a calcitonin gene related peptide (CGRP) pathway monoclonal antibody. For instance, the calcitonin gene related peptide (CGRP) pathway monoclonal antibody can comprise an anti-CGRP antibody, an anti-CGRP-receptor (CGRP-R) antibody, or both. In an exemplary embodiment, the anti-CGRP antibody is fremanezumab. In another embodiment, the anti-CGRP antibody is galcanezumab. In one embodiment, the anti-CGRP antibody is eptinezumab. An exemplary, anti-CGRP-R antibody includes erenumab.

In certain embodiments, the anti-PACAP antibody described herein is administered in combination with Onabotulinumtoxin A.

In certain embodiments, the anti-PACAP antibody described herein is administered in combination with any of the above described CGRP pathway monoclonal antibody. In certain embodiments, the anti-PACAP antibody described herein is administered in combination with fremanezumab.

In certain embodiments, the anti-PACAP antibody described herein is administered in combination with galcanezumab.

In certain embodiments, the anti-PACAP antibody described herein is administered in combination with eptinezumab.

In certain embodiments, the anti-PACAP antibody described herein is administered in combination with erenumab.

In some embodiments, the anti-PACAP antibodies described herein can be used in combination with other anti-PACAP antibodies known in the art, such as those described in WO2017181031, WO2017181039, WO2017106578, and WO2019067293.

In some embodiments, the anti-PACAP antibodies described herein can be used in combination with anti-PAC1 antibodies as described in WO2019140216 and WO2014144632.

In some embodiments, the anti-PACAP antibody described herein may be used in patients with migraine in a subpopulation identified by physiological measures of autonomic function. For example, the subpopulation can be identified by (i) baseline ictal or inter-ictal PACAP levels, plasma, lacrimal fluid, saliva, or other biological sample; (ii) baseline physiologic measurements of autonomic function such as pupillary light reflex and galvanic skin response; and (iii) baseline ictal or inter-ictal autonomic response to PACAP infusion.

In some embodiments, the administration of a therapeutically effective amount of the anti-PACAP antibody or the pharmaceutical composition described herein can result in delaying the onset of a condition discussed herein, reducing the duration of the condition, or reducing the severity of the condition.

Administration of any one or more of the compositions described herein, e.g., the anti-PACAP antibody can be incorporated into therapeutic compositions or combination therapy regimens for use in the methods of treating or preventing as described herein. For example, the combination therapy of the anti-PACAP antibody with any of the above described CGRP pathway monoclonal antibodies (e.g. fremanezumab) can be incorporated into one therapeutic composition or as a two separated therapeutic compositions for use in the methods of treating or preventing of PACAP-related conditions such as headache, migraine, or any of the above described conditions. The anti-PACAP antibody or the pharmaceutical composition of the disclosure are typically administered in solution or suspension formulation by injection or infusion. In an exemplary embodiment, an anti-PACAP antibody can be administered by injection directly into the individual. In another exemplary embodiment, an anti-PACAP antibody can be administered by systemic infusion. Some anti-PACAP antibodies of the disclosure (e.g., 890C) are effective at a concentration of equivalent to about 300 picomolar (pM) in a cell based assay. The cell-based assay may be an assay which monitors cyclic adenosine monophosphate (cAMP) production in the presence of anti-PACAP antibodies (Wang, T., et al. (2004). Measurement of CAMP for G($\alpha$s)- and G($\alpha$i) Protein-Coupled Receptors (GPCRs). Assay Guidance Manual. S. Markossian, G. S. Sittampalam, A. Grossman et al. Bethesda (MD), Eli Lilly & Company and the National Center for Advancing Translational Sciences). CAMP is an important intracellular second messenger in GPCR signal transduction. Agonist activation of GPCRs that couple to the G($\alpha$s) protein leads to an increased production of intracellular cAMP levels, whereas activation of GPCRs that couple to the G($\alpha$i) protein leads to reduced production of intracellular cAMP levels. Both of these intracellular cAMP changes are mediated through the modulation of adenylate cyclase activity. cAMP regulates the activity of cAMP-dependent protein kinase A (PKA), which plays an important role in a variety of downstream cellular processes. A number of reagent kits are available on the market that can be used to measure intracellular cAMP levels. These include the HTRF CAMP kit from Cisbio, the LANCE CAMP kit from PerkinElmer, the HitHunter CAMP kit from DiscoverX and the CAMP Direct Immunoassay Kit from Abcam and Bio Vision. These assays are all based on the use of antibodies that specifically recognize both intracellular CAMP and an exogenous labeled cAMP conjugate that acts as a competitor, followed by detection of the labeled cAMP conjugate by a variety of detection technologies, including fluorescence resonance energy transfer (FRET) or enzymatic reactions. In addition, the antibody-independent GloSensor cAMP assay from Promega employs semi-split luciferase, which reassembles when bound to CAMP. Other anti-PACAP antibodies provided herein may be most effective at a higher or lower concentration, depending on the binding affinity for PACAP, and the degree of expression of PACAP in an individual. In some embodiments, antibodies or antigen-binding fragments thereof of the disclosure are effective at a concentration of equivalent to about 30 to about 90 pM in a cell based assay. In some embodiments, antibodies or antigen-binding fragments thereof of the disclosure are effective at a concentration of equivalent to about 40 to about 80 pM in a cell based assay. In some embodiments, antibodies or antigen-binding fragments thereof of the disclosure are effective at a concentration of equivalent to about 50 to about 70 pM in a cell based assay. In some embodiments, antibodies or antigen-binding fragments thereof of the disclosure are effective at a concentration of equivalent to about 60, 65, 67, 69, or 70 pM in a cell based assay.

Systems and Kits

Also provided herein are systems and kits including the anti-PACAP antibodies, recombinant nucleic acids, recombinant cells, or pharmaceutical compositions provided and described herein as well as written instructions for making and using the same. For example, provided herein, in some embodiments, are systems and/or kits that include one or more of: an anti-PACAP antibody as described herein, a recombinant nucleic acid as described herein, a recombinant cell as described herein, or a pharmaceutical composition as described herein. In some embodiments, the systems and/or kits of the disclosure further include one or more syringes (including pre-filled syringes) and/or catheters used to administer one any of the provided anti-PACAP antibodies, recombinant nucleic acids, recombinant cells, or pharmaceutical compositions to an individual. In some embodiments, a kit can have one or more additional therapeutic agents that can be administered simultaneously or sequentially with the other kit components for a desired purpose, e.g., for modulating an activity of a cell, inhibiting a target cancer cell, or treating a disease in an individual in need thereof.

Any of the above-described systems and kits can further include one or more additional reagents, where such additional reagents can be selected from: dilution buffers; reconstitution solutions, wash buffers, control reagents, control expression vectors, negative control polypeptides, positive control polypeptides, reagents for in vitro production of the bispecific binding agents or engineered transmembrane protein.

In some embodiments, a system or kit can further include instructions for using the components of the kit to practice the methods. The instructions for practicing the methods are generally recorded on a suitable recording medium. For example, the instructions can be printed on a substrate, such as paper or plastic, and the like. The instructions can be present in the kits as a package insert, in the labeling of the container of the kit or components thereof (i.e., associated with the packaging or sub-packaging), and the like. The instructions can be present as an electronic storage data file present on a suitable computer readable storage medium, e.g. CD-ROM, diskette, flash drive, and the like. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature cited above. Additional embodiments are disclosed in further detail in the following examples, which are provided by way of illustration and are not in any way intended to limit the scope of this disclosure or the claims.

Example 1: Generation of Anti-PACAP Antibodies

This Example briefly describes the procedure of the generation of the antibodies provided in the present disclosure.

Anti-PACAP monoclonal antibodies were isolated from immunized mice. Plasma cells were isolated from mice based on their selectivity to PACAP. Single B-cells were screened against PACAP-38 and VIP, for example by using techniques known in the literature such as those described in Winters et al. Rapid single B cell antibody discovery using nanopens and structured light. mAbs Volume 11, 2019-Issue 6; Asensio et al. Antibody repertoire analysis of mouse immunization protocols using microfluidics and molecular genomics. mAbs Volume 11, 2019-Issue 5; Seah et al. Microfluidic single-cell technology in immunology and antibody screening. Mol Aspects Med. 2018; 59:47-61; Proserpio et al. Single-cell technologies are revolutionizing the approach to rare cells. Immunol Cell Biol. 2016; 94 (3): 225-229; El Debs et al. Functional single-cell hybridoma screening using droplet-based microfluidics. Proc Natl Acad Sci USA. 2012; 109 (29): 11570-11575; and Theberge et al. Microdroplets in microfluidics: an evolving platform for discoveries in chemistry and biology. Angew Chem Int Ed Engl. 2010; 49 (34): 5846-5868. More than 61,000 B-cells were screened. Positive B-cells secreting antigen specific antibodies were isolated and sequenced.

Sequencing and cloning of 201 antibodies encoding immunoglobulin heavy and light chains were performed. 39 antibodies with PACAP-selective binding were identified. Two clones were chosen for further optimization. These antibodies exhibited high PACAP binding affinity and low to no VIP binding affinity. Further, both exhibited high potency against PACAP and low to no potency against VIP.

Both antibodies showed high affinity and potency against PACAP38 and PACAP27 as measured by SPR at 37° C. and functional cell-based assay to measure PACAP27/PACAP38-mediated cAMP accumulation using human PAC1-expressing cell line. The optimization process produced more than 660 humanized variants to generate a candidate high affinity and highly potent antibody, and at the same time an antibody that possesses a reduced risk for potential immunogenicity as measured by ProImmune REVEAL® (peptide-MHC class II stability) assays and by the high humanness score.

The humanized variant with retained potency was further optimized through in vitro affinity maturation, which involved generating a combinatorial library of more than 100 million (108) variants. About 950 further variants were screened to address potential manufacturability and immunogenicity while retaining potency profiles.

Table 14, below, shows exemplary humanized variants that were screened for binding affinity, potency, and predicted immunogenicity.

TABLE 14

| Variant No. | HC (substitution using Kabat numbering) | | | | LC (substitution using Kabat numbering) | | | ka (1/Ms) | kd (1/s) | KD (M) | Assay temp | PACAP-38 IC50 (nM) | Predicted Immuno-genicity |
|---|---|---|---|---|---|---|---|---|---|---|---|---|---|
| | H-CDR1 | H-CDR2 | FW3 | H-CDR3 | L-CDR1 | L-CDR2 | L-CDR3 | | | | | | |
| 919A | E16S F27G T30 S S32 | F531 S54F T57 | A93 194 | Y96 G98 | S(27E) G29 | L50 V51 K53T L54R D55E | H93 P95 | 6.75E+07 | 5.84E−03 | 8.66E−11 | 37° C. | 1.30 | +++ |
| 917B | E16S F27G T30S S32 | F531 S54F T57 | A93 194 | Y96Q G98 | S(27E) G29 | L50 V51 K53T L54R D55E | H93W P95 | 1.26E+07 | 1.22E−04 | 9.69E−12 | 37° C. | 0.19 | ++ |
| 890C | E16S F27G T30S S32V | F531 S54F T57 | A93 194 | Y96Q G98 | S(27E)A G29 | L50W V51A K53T L54R D55E | H93W P95D | 2.36E+07 | 6.71E−04 | 2.84E−11 | 37° C. | 0.32 | − |
| 608C | E16S F27G T30S S32L | F531 S54F T57 | A93 194 | Y96Q G98 | S(27E) G29 | L50W V51A K53T L54R D55E | H93W P95D | 7.19E+07 | 2.04E−03 | 2.84E−11 | 37° C. | 0.70 | − |
| 627C | E16S F27G T30S S32V | F531 S5 4F T57 | A93 194 | Y96Q G98 | S(27E) G29 | L50W V51A K53T L54R D55E | H93W P95D | 2.10E+07 | 7.89E−04 | 3.76E−11 | 37° C. | 0.40 | − |
| 609C | E16S F27G T30S S32L | F531 S54F T57 | A93 194 | Y96Q G98 | S(27E)A G29 | L50W V51A K53T L54R | H93W P95D | 5.17E+07 | 1.18E−03 | 2.28E−11 | 37° C. | 0.83 | − |
| 604C | E16S | F531 | A93 | Y96Q | S(27E) | L50W | H93W | 1.62E+07 | 3.19E−04 | 1.97E−11 | 37° C. | 0.16 | ++ |

TABLE 14-continued

| Variant No. | HC (substitution using Kabat numbering) | | | | LC (substitution using Kabat numbering) | | | ka (1/Ms) | kd (1/s) | KD (M) | Assay temp | PACAP-38 IC50 (nM) | Predicted Immuno-genicity |
|---|---|---|---|---|---|---|---|---|---|---|---|---|---|
| | H-CDR1 | H-CDR2 | FW3 | H-CDR3 | L-CDR1 | L-CDR2 | L-CDR3 | | | | | | |
| | F27G T30S S32 | S54F T57 | 194 | G98 | G29 | V51A K53T L54R D55E | P95D | | | | | | |
| 605C | E16S F27G T30S S32 | F531 S54F T57 | A93 194 | Y96Q G98 | S(27E)A G29 | L50W V51A K53T L54R D55E | H93W P95D | 3.33E+07 | 5.66E−04 | 1.70E−11 | 37°C | 0.15 | ++ |
| 519C | E16S F27G T30S S32L | F531 S54F T57 | A93 194 | Y96Q G98 | S(27E) G29 | L50 V51 K53T L54R D55E | H93W P95D | 2.22E+07 | 4.83E−04 | 2.18E−11 | 37° C. | 0.27 | +++ |
| 524C | E16S F27G T30S S32 | F531 S54F T57Q | A93 194 | Y96Q G98A | S(27E) G29 | L50 V51 K53T L54R D55E | H93W P95D | 1.56E+07 | 5.46E−04 | 3.50E−11 | 37° C. | 0.36 | +++ |

Four humanized antibodies (890C, 608C, 627C and 609C), showed high affinity, high potency, and lower predicted immunogenicity.

Antibody developability criteria, such as that described in example 7, were used to identify variants with best developability profile.

As can be seen from Table 14, highest binding affinity does not readily necessarily correlate with predicted immunogenicity. By way of example, variant 524C exhibited a higher binding affinity than variant 890C, 608C, 627C and 609C, but also exhibited high predicted immunogenicity profile, whereas 890C, 608C, 627C and 609C, had none. Further, potency for PACAP also does not predict favourable qualities for immunogenicity and developability. By way of example, variant 519C exhibited higher potency than variant 890C, 608C, 627C and 609C, but also exhibited high predicted immunogenicity profile, whereas 890C, 608C, 627C and 609C had none. By a way of example, the predicted immunogenicity profile was mesaued by the assay as described in Example 3.

Example 2: Humanness of the Anti-PACAP Antibodies

This Example describes the humanness of antibodies provided in the present disclosure.

Increasing the humanness of the variable region sequence of monoclonal antibodies that are potential therapeutic candidate is an important approach to minimize potential immunogenicity. The anti-PACAP antibodies of the present disclosure were engineered to obtain a high humanness score without compromising the high affinity and high potency as described herein. A humanness score, i.e., similarity to human germline sequence, was obtained using various antibody analysis platforms, including IMGT and AbGenesis. Starting with a single input variable region antibody sequence, the closest human germline of the sequence was identified and the percentage of humanness of the variable heavy and light chains was computed using AbGenesis software (Release 4.1). The overall humanness of the antibody was calculated based on average percent sequence identity values of the heavy and light chains.

The humanness scores of some exemplary anti-PACAP antibodies of the present disclosure and some known anti-PACAP antibodies are shown in Table 15.

TABLE 15

HUMANNESS SCORES

| Antibody | VH % | VK % | % Humanness |
|---|---|---|---|
| 608C | 88.2 | 90.7 | 89.5 |
| 627C | 88.2 | 90.7 | 89.5 |
| 609C | 88.2 | 89.8 | 89.0 |
| 604C | 88.2 | 90.7 | 89.5 |
| 605C | 88.2 | 89.8 | 89.0 |
| 890C | 88.2 | 89.8 | 89.0 |
| 919A | 88.2 | 85.8 | 87.0 |
| 917B | 88.2 | 88.8 | 88.5 |
| Ab C and D | 92.3 | 88.7 | 90.5 |
| Ab1H | 86.4 | 87.8 | 87.1 |
| Ab10.H3 | 77.7 | 85.1 | 81.4 |

As shown above, the anti-PACAP antibodies (e.g., 608C, 627C, 609C, 604C, 605C and 890C) all have at least 89% humanness, which is higher than the known anti-PACAP antibody Ab1h described in WO2017181031 and antibody Ab10.H3 described in WO2017181039. Anti-PACAP antibodies Ab C and D are described in WO2019067293. Sequences that are not identical to germline are of particular interest in further immunogenicity prediction analyses, as described in the following example.

Example 3: Predicted Immunogenicity of the Anti-PACAP Antibodies

This Example describes the predicted immunogenicity of antibodies provided in the present disclosure.

During the process of generating the antibodies described herein, antibodies with predicted low immunogenicity were progressed to further optimization excluding those with epitopes predicted by peptide-MHC class II stability analyses.

Synthesized peptides, from the heavy and light chain variable regions of the anti-PACAP antibodies provided herein, such as the antibodies described in example 2 (Table 15), covering all non-germline residues, were incubated with recombinant MHC Class II proteins. ProImmune REVEAL® assays was used to assess stability of peptide binding to MHC class II molecules. For example, 15 residue long synthetic peptides from the heavy and the light chain sequence covering all non-germline residues were assessed for the tested antibodies.

The MHC Class II alleles analysed included all with a frequency of at least 3% in global population. The binding of the peptides to the MHC Class II was detected by ELISA. These analyses identified low predicted immunogenicity antibodies such as 608C, 609C, 627C and 890C, for which all tested peptides showed either no or low stability interaction with MHC II class protein (FIG. 7). In contrast, analyses of prior described anti-PACAP antibodies, such as Ab1H, Ab10.H3, Ab B, Ab C or Ab D all showed predicted immunogenic epitopes Example 4: Kinetics of the Anti-PACAP Antibodies This Example describes the kinetics of antibodies provided in the present disclosure.

In brief, antibody and peptide interaction was determined on a Biacore S200 (GE Healthcare) by method previously described (Andreu and Gomes 2002). An anti-Human IgG Fc capture antibody was immobilized on a CM5 biosensor chip via standard amine coupling. Anti-PACAP antibodies were injected and captured to 200 to 400 response units (RU,). PACAP38, PACAP27 and VIP were diluted in HBS-EP+ buffer containing 0.1% w/v BSA (Bovostar, catalog number BSAS1.0) and 0.15 M NaCl (Sigma-Aldrich catalog number S7653), pH 7.4. Binding kinetics of antibodies were determined by injection of two-fold serial dilutions of PACAPs (12 nm to 0 nM) and VIP (1200 nM to 0 nM) in running buffer at 37° C. with a flow rate of 40 uL/min for 2 min followed by a dissociation for 10 minutes. For subsequent cycles, the chip was regenerated using 0.85% phosphoric acid. Data was analysed with the Biacore S200 Evaluation Software (ver 1.0). Association rate (ka) and dissociation rate (ka) constants were determined using a simple one-to-one Langmuir binding model and used to calculate the equilibrium dissociation constant ($K_D$).

The same assay format was used to capture antibody from supernatant and a single analyte injection of 33.3 nM PACAP was used for off-rate ranking of antibody variants. An exemplary Biacore-based off-rate ranking assay involves single concentration of PACAP38 is shown in Table 16.

TABLE 16

BINDING MEASUREMENT OF ANTI-PACAP VARIANTS

| Ab ID | ka (1/Ms) | kd (1/s) | KD (M) |
|---|---|---|---|
| 516C | 2.34E+07 | 5.51E−03 | 2.35E−10 |
| 604C | 1.62E+07 | 3.19E−04 | 1.97E−11 |
| 605C | 3.33E+07 | 5.66E−04 | 1.70E−11 |
| 606C | 4.74E+07 | 1.46E−03 | 3.08E−11 |
| 607C | 9.72E+06 | 8.81E−04 | 9.06E−11 |
| 608C | 7.19E+07 | 2.04E−03 | 2.84E−11 |
| 609C | 5.17E+07 | 1.18E−03 | 2.28E−11 |
| 610C | 7.55E+07 | 5.61E−03 | 7.43E−11 |
| 611C | 2.72E+07 | 2.03E−03 | 7.46E−11 |
| 614C | 3.96E+06 | 5.17E−03 | 1.31E−09 |
| 616C | 3.58E+06 | 2.80E−03 | 7.82E−10 |
| 621C | 1.76E+07 | 7.85E−04 | 4.46E−11 |
| 627C | 2.10E+07 | 7.89E−04 | 3.76E−11 |
| 632C | 3.92E+06 | 5.74E−03 | 1.46E−09 |
| 633C | 8.94E+06 | 1.52E−03 | 1.70E−10 |
| 638C | 1.58E+07 | 1.55E−03 | 9.81E−11 |
| 650C | 6.91E+06 | 3.18E−03 | 4.60E−10 |

TABLE 16-continued

BINDING MEASUREMENT OF ANTI-PACAP VARIANTS

| Ab ID | ka (1/Ms) | kd (1/s) | KD (M) |
|---|---|---|---|
| 667C | 7.62E+06 | 3.59E−03 | 4.71E−10 |
| 684C | 1.16E+07 | 5.27E−03 | 4.54E−10 |
| 701C | 5.67E+06 | 3.02E−03 | 5.33E−10 |
| 746C | 5.14E+07 | 5.62E−03 | 1.09E−10 |
| 752C | 3.23E+07 | 8.31E−03 | 2.57E−10 |
| 757C | 3.46E+07 | 7.92E−03 | 2.29E−10 |
| 763C | 2.89E+07 | 2.65E−03 | 9.17E−11 |
| 769C | 1.50E+07 | 3.91E−03 | 2.61E−10 |
| 774C | 1.72E+07 | 4.10E−03 | 2.38E−10 |
| 882C | 1.38E+07 | 8.12E−04 | 5.88E−11 |
| 883C | 2.67E+07 | 2.30E−03 | 8.61E−11 |
| 884C | 1.39E+07 | 1.56E−03 | 1.12E−10 |
| 885C | 2.98E+07 | 7.50E−03 | 2.52E−10 |
| 886C | 1.45E+07 | 3.65E−03 | 2.52E−10 |
| 889C | 1.70E+07 | 1.41E−03 | 8.29E−11 |
| 890C | 2.36E+07 | 6.71E−04 | 2.84E−11 |
| 895C | 1.52E+07 | 2.13E−03 | 1.40E−10 |
| 896C | 1.81E+07 | 2.66E−03 | 1.47E−10 |
| 897C | 1.42E+07 | 2.30E−03 | 1.62E−10 |
| 898C | 2.00E+07 | 1.22E−03 | 6.10E−11 |
| 899C | 2.31E+07 | 1.58E−03 | 6.84E−11 |

Figure 3B:
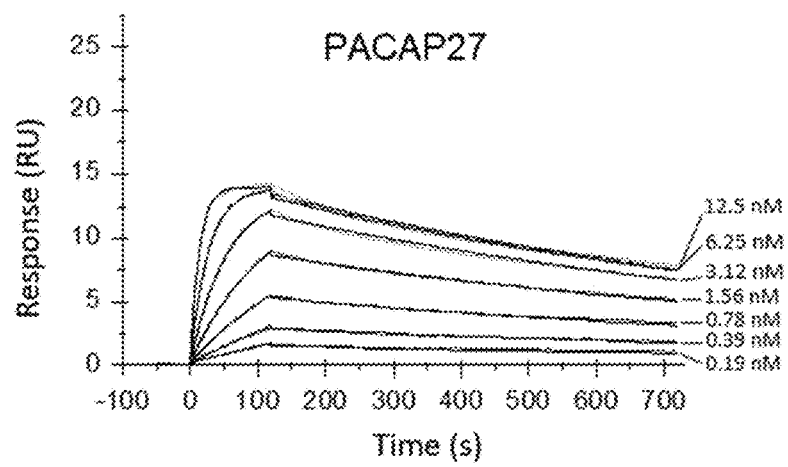
Figure 3C:
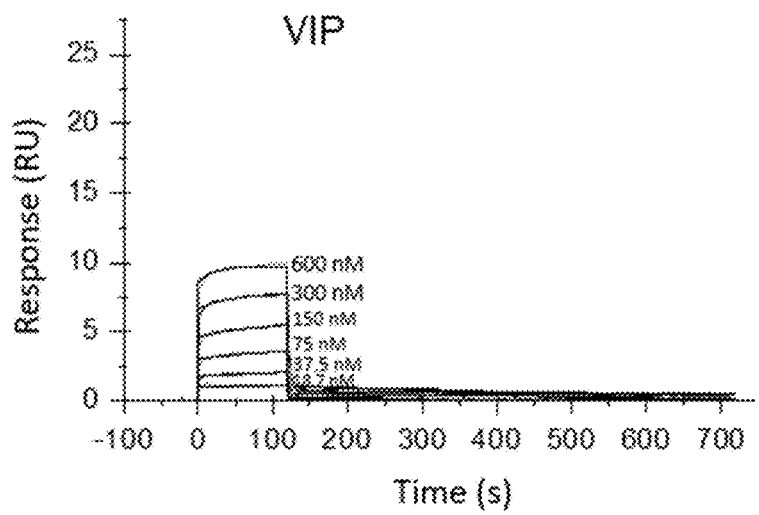

FIGS.-3A, 3B, 3C show example of Binding affinity analysis of anti-PACAP antibody 605C to PACAP38 and PACAP27 and VIP by SPR. Further, Table 17 shows that anti-PACAP antibody 605C binds PACAP38 and PACAP27 with high affinity and selectivity. Due to very fast on-rate and off-rate with VIP, binding affinity at steady state was used.

TABLE 17

BINDING OF 605C TO PACAP38 AND PACAP27

| | ka (1/Ms) | kd (1/s) | KD (M) |
|---|---|---|---|
| PACAP38 | 1.72E+07 | 5.65E−04 | 3.28E−11 |
| PACAP27 | 6.58E+06 | 1.01E−03 | 1.54E−10 |
| VIP | Steady state binding | | 2.25E−07 |

Example 5: Potency of the Anti-PACAP Antibodies

This Example describes the potency of antibodies provided in the present disclosure.

A cell-based assay to measure PACAP-induced cAMP accumulation following methods previously described (Wang, Li et al. 2004) was performed. Specifically, inhibition of PACAP38- or PACAP27-induced signalling via PAC1, VPAC1 and VPAC2 receptors utilized CHO-K1 cell lines stably expressing either human PAC1, VPAC1 or VPAC2 receptors (Eurofins/Discover X) and endpoint was determined using Promega CAMP-Glo™ ™ Table 18 below summarizes the IC50 of some exemplary anti-PACAP antibodies provided herein.

TABLE 18

| $IC_{50}$ COMPARISON | |
|---|---|
| Ab ID | $IC_{50}$ (nM) |
| 890C | 0.32 |
| 608C | 0.70 |
| 627C | 0.40 |
| 609C | 0.83 |
| 917B | 0.19 |

Example 6: Selectivity of the Anti-PACAP Antibodies

This Example describes the selectivity of antibodies provided in the present disclosure.

The anti-PACAP antibodies, e.g., 890C, were tested against related peptides in the Secretin Glucagon family (Table 19) to determine the presence and extent of any off-target binding. Nine bioactive peptides in the glucagon superfamily are: PACAP, VIP, glucagon, Glucagon-Like Peptides (GLP-1, GLP-2), Growth Hormone Releasing Factor (GRF or GHRF), Peptide Histidine Methionine (PHM), secretin, and Gastric inhibitory polypeptide (GIP). Following capture of antibodies as described in example 4, the antibody and the peptide interaction was measured by injection of 37.5 nM of each peptide diluted in buffer at 37° C. with a flow rate of 50 mL/min for 2 min followed by a dissociation phase of 4-5 min. Samples were injected in a multi-cycle manner over freshly captured anti-PACAP antibody, by regenerating the capture surfaces with two injections of 0.85% phosphoric acid at a flow rate of 30 µL/min.

TABLE 19

PEPTIDES IN THE SECRETIN GLUCAGON FAMILY

| Peptide | Sequence |
|---|---|
| PACAP38 | HSDGIFTDSYSRYRKQMAVKKYLAAVLGKRYKQRVKNK (SEQ ID NO: 13) |
| PACAP27 | HSDGIFTDSYSRYRKQMAVKKYLAAVL (SEQ ID NO: 14) |
| VIP | HSDAVFTDNYTRLRKQMAVKKYLNSILN (SEQ ID NO: 15) |
| PHM | HADGVFTSDFSKLLGQLSAKKYLESLM (SEQ ID NO: 77) |
| Secretin | HSDGTFTSELSRLREGARLQRLLQGLV (SEQ ID NO: 78) |
| Glucagon | HSQGTFTSDYSKYLDSRRAQDFVQWLMNT (SEQ ID NO: 79) |
| GIP | YAEGTFISDYSIAMDKIHQQDFVNWLLAQKGKKNDWKHNITQ (SEQ ID NO: 80) |
| GLP-1 | HAEGTFTSDVSSYLEGQAAKEFIAWLVKGR (SEQ ID NO: 81) |
| GLP-2 | HADGSFSDEMNTILDNLAARDFINWLIQTKITD (SEQ ID NO: 82) |
| GRF | YADAIFTNSYRKVLGQLSARKLLQDIMSRQQGESNQERGARARL (SEQ ID NO: 83) |

Figure 4:
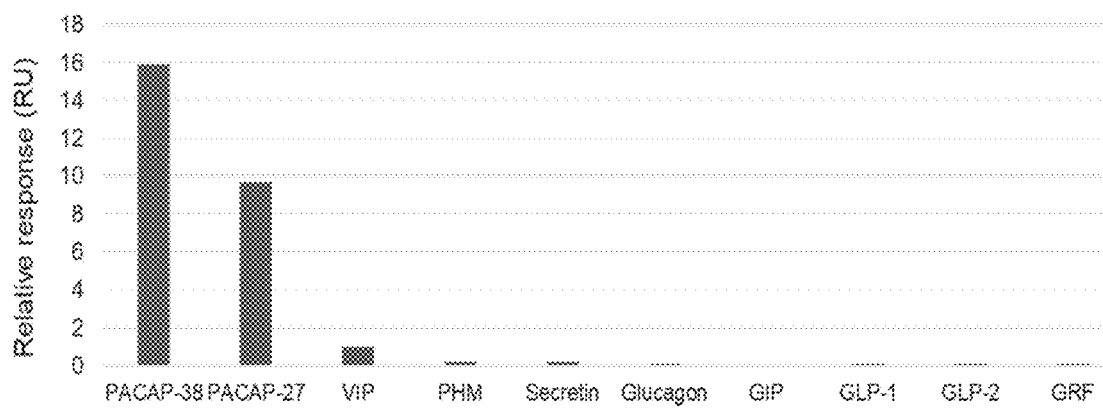
FIG. 4 shows exemplary experimental SPR data on anti-PACAP antibody 890C binding to PACAP38, PACAP27, VIP and other Glucagon-Secretin family peptides.
Figure 5:
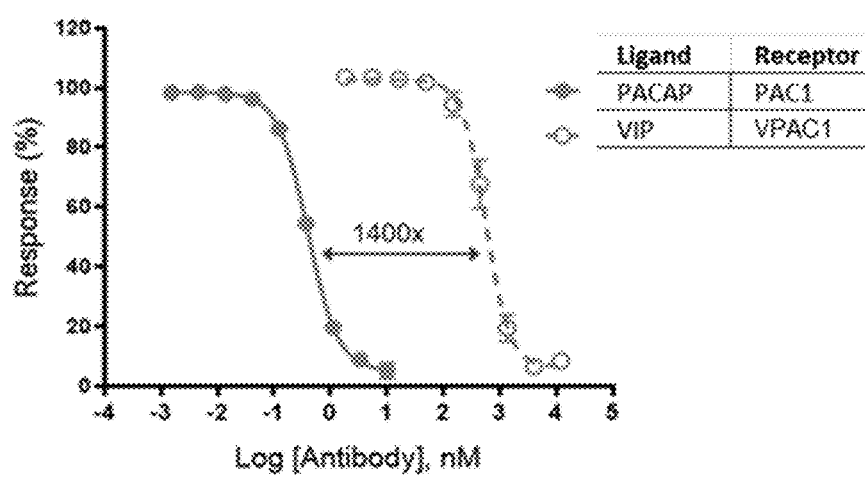
FIG. 5 shows exemplary experiment data for the selectivity of activity of the anti-PACAP antibody 890C to PACAP38 vs VIP in cell-based cyclic AMP induction assays.

As shown in FIG. 4, at the stability level determined by Biacore (relative binding after 15 sec dissociation), the antibody 890C is highly selective for PACAP with no or minimal binding to other Glucagon-Secretin family peptides. Affinity, measured by SPR and expressed in pM, of 890C to PACAP38, PACAP27 and VIP is 54, 218 and 390,000, respectively. The selectivity of antibody 890C was assessed by comparing the inhibition of PACAP38-signalling to inhibition of VIP-signalling in a cyclic AMP (CAMP) measuring cell-based functional assay. As shown in FIG. 5, antibody 890C displayed >1000-fold selectivity when inhibiting PACAP38-induced cAMP production in CHO-K1 cells stably expressing the PAC1 receptor versus inhibition of VIP-induced cAMP production in CHO-K1 cells stably expressing the VPAC1 receptor.

Example 7: Developability Assessment Using HPLC-SEC Analysis

Developability of antibody molecules can be assessed using biophysical techniques that measure non-specific interaction of antibody molecules. It has been shown that in high performance liquid chromatography (HPLC) analysis of antibodies using either silica based columns or a dextran based size-exclusion columns, the retention times of antibody samples are related to their colloidal stability; with antibodies prone to precipitation or aggregation retained longer on the column, presumably due to non-specific interaction of antibodies with the column matrix (Kohli et al., (2015) mAbs, 7:4, 752-758, DOI: 10.1080/19420862.2015.1048410. Apparent molecular weights of antibodies can be calculated using molecular weight standards. Longer retention times appear as lower apparent molecular weight than that calculated based on the sequence.

Figure 6:
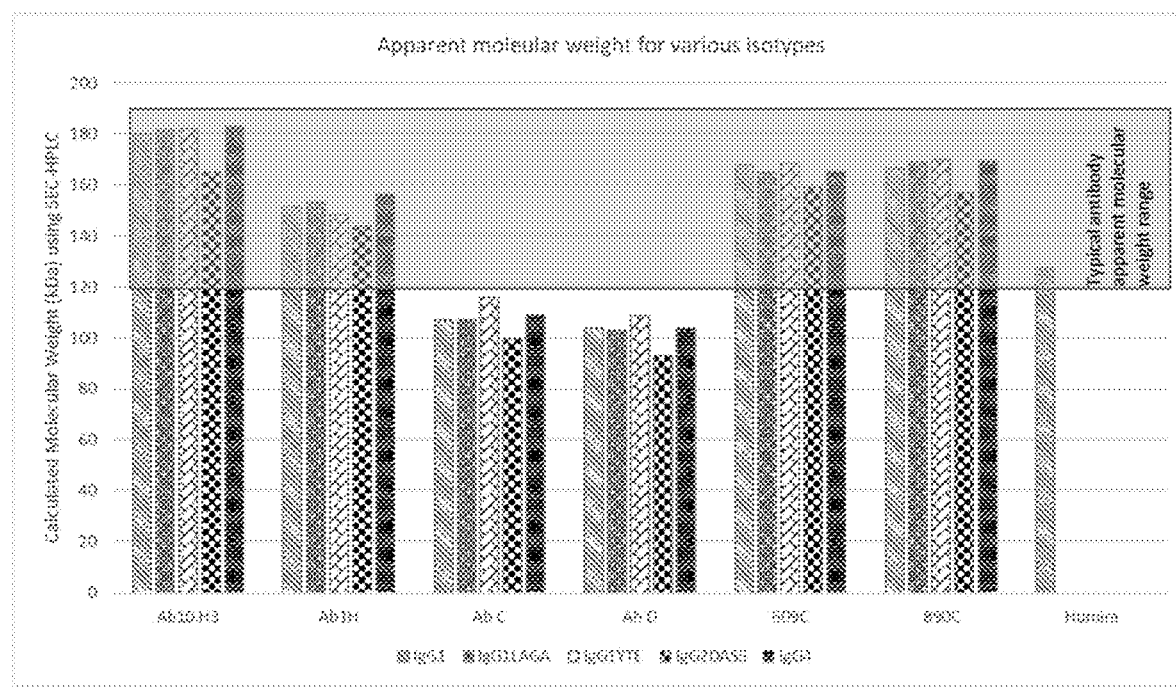
FIG. 6 shows the apparent molecular weight for some exemplary anti-PACAP antibodies provided herein and other anti-PACAP antibodies in various isotype formats.

As shown in FIG. 6, antibodies with an acceptable IgG have a typical molecular weight around 155 kDa. Antibodies 609C and 890C eluted normally, with an apparent molecular weight window of 155 kDa-165 kDa, while Ab C and Ab D displayed significantly increased retention time with an apparent molecular weight of around 95-105 kDa depending on the IgG isoform. These data demonstrate that the antibodies 609C and 890C are expected to have better developability as they have appropriate colloidal stability as reflected by retention time on the column.

Example 8: Single Dose Study in Cynomolgus Monkeys of Anti-PACAP Monoclonal Antibody 4 biologics-naïve male cynomolgus monkeys received a single dose of anti-PACAP antibody having the following CDRs: VH-CDR1, VH-CDR2, and VH-CDR3 sequences and VL-CDR1, VL-CDR2, and VL-CDR3 sequences set forth in SEQ ID NO: 1, 2, and 3 and SEQ ID NO: 4, 5, and 6, respectively, at 10 mg/kg via subcutaneous administration. Sampling for pharmacokinetic and pharmacodynamic analysis, hematology and clinical chemistry assessment were carried out. Pharmacodynamic analysis was carried out by ex vivo assay, for example, by comparing the serum sample of the injected animal in a pre-dose sample of the same animal. No durable antibody-related hematology, clinical chemistry or body weight changes were observed. The antibody serum concentration time profiles are comparable to typical monoclonal antibody profile in cynomolgus monkeys.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

| SEQ ID NO | Name | Sequence |
|---|---|---|
| 1 | VH-CDR1 890C and 627C | GGTFSDVYMH |
| 2 | VH-CDR2 For all | YPIFAD |
| 3 | VH-CDR3 for all | DQDGSFAY |
| 4 | VL-CDR1 890C and 609C | DADGK |
| 5 | VL-CDR2 for all | WASTRES |
| 6 | VL-CDR3 for all | WQGTWFDLT |
| 7 | VH-CDR1 608C and 609C | GGTFSDLYMH |
| 8 | VL-CDR1 608C and 627C | DSDGK |
| 9 | VH-CDR1 consensus | GGTFSD*Xa*YMH |
| 10 | VL CDR1 consensus | D*Xb*DGK |
| 11 | VH 890C and 627C | EVQLVQSGAEVKKPGSSVKVSCKASGGTFSDVYMHWVRQAPGQGLEWMGLIYPIFADTRYAQKFQGRVTITADESTSTAYMELSSLRSEDTAVYYCAIDQDGSFAYWGQGTLVTVSS |
| 12 | VH 608C and 609C | EVQLVQSGAEVKKPGSSVKVSCKASGGTFSDLYMHWVRQAPGQGLEWMGLIYPIFADTRYAQKFQGRVTITADESTSTAYMELSSLRSEDTAVYYCAIDQDGSFAYWGQGTLVTVSS |
| 13 | PACAP38 | HSDGIFTDSYSRYRKQMAVKKYLAAVLGKRYKQRVKNK |
| 14 | PACAP27 | HSDGIFTDSYSRYRKQMAVKKYLAAVL |
| 15 | VIP | HSDAVFTDNYTRLRKQMAVKKYLNSILN |
| 16 | VL CDR2 consensus | WASTRES |
| 17 | IGHV1-69*01 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCAR |
| 18 | VH 919A | EVQLVQSGAEVKKPGSSVKVSCKASGGTFSDSYMHWVRQAPGQGLEWMGLIYPIFADTRYAQKFQGRVTITADESTSTAYMELSSLRSEDTAVYYCAIDYDGSFAYWGQGTLVTVSS |
| 19 | VH 917B | EVQLVQSGAEVKKPGSSVKVSCKASGGTFSDSYMHWVRQAPGQGLEWMGLIYPIFADTRYAQKFQGRVTITADESTSTAYMELSSLRSEDTAVYYCAIDQDGSFAYWGQGTLVTVSS |
| 20 | VK 890C and 609C | DIVMTQSPDSLAVSLGERATINCKSSQSLLDADGKTYLNWLQQKPGQPPKRLIYWASTRESGVPDRFSGSGSGTDFTLTISSLQAEDVAVYYCWQGTWFDLTFGGGTKVEIK |
| 21 | VK 608C and 627C | DIVMTQSPDSLAVSLGERATINCKSSQSLLDSDGKTYLNWLQQKPGQPPKRLIYWASTRESGVPDRFSGSGSGTDFTLTISSLQAEDVAVYYCWQGTWFDLTFGGGTKVEIK |
| 22 | VK 917B | DIVMTQSPDSLAVSLGERATINCKSSQSLLDSDGKTYLNWLQQKPGQPPKRLIYLVSTRESGVPDRFSGSGSGTDFTLTISSLQAEDVAVYYCWQGTWFDLTFGGGTKVEIK |
| 23 | Human kappa (CL) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 24 | Human lambda (CL) | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| 25 | 605C, 919A VH-CDR1 | GGTFSDSY |

| SEQ ID NO | Name | Sequence |
|---|---|---|
| 26 | IGKV4-1*01 | DIVMTQSPDSLAVSLGERATINCKSSQSVLYSNNKNYLAWY QQKPGQPPKLLIYWASTRESGVPDRFSGSGSGTDFTLTISSLQ AEDVAVYYCQQYYSTP |
| 27 | VK 919A | DIVMTQSPDSLAVSLGERATINCKSSQSLLDSDGKTYLNWLQ QKPGQPPKRLIYLVSTRESGVPDRFSGSGSGTDFTLTISSLQAE DVAVYYCWQGTHFPLTFGGGTKVEIK |
| 28 | 890C VH-CDR1 | GGTFSDVY |
| 29 | VRFR-1 | EVQLVQSGAEVKKPGSSVKVSCKAS |
| 30 | VRFR-2 | WVRQAPGQGLEWMGLI |
| 31 | VRFR-3 | TRYAQKFQGRVTITADESTSTAYMELSSLRSEDTAVYYCAI |
| 32 | VRFR-4 | WGQGTLVTVSS |
| 33 | VLFR-1 | DIVMTQSPDSLAVSLGERATINCKSSQSLL |
| 34 | VLFR-2 | TYLNWLQQKPGQPPKRLIY |
| 35 | VLFR-3 | GVPDRFSGSGSGTDFTLTISSLQAEDVAVYYC |
| 36 | VLFR-4 | FGGGTKVEIK |
| 37 | Human IgG1 | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG |
| 38 | Human IgG1 FAB TAG | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSC |
| 39 | Human IgG1 KiH Hole | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSRDELTKNQVSLSCA VKGFYPSDIAVEWESNGQPENNYKTTPPVLDSDGSFFLVSKL TVDKSRWQQGNVFSCSVMHEALHNHYTQKSLSLSPG |
| 40 | Human IgG1 KiH Knob | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPELLGGPSVFLFP PKPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSRDELTKNQVSLWCL VKGFYPSDIAVEWESNGQPENNYKTTPPVLDSDGSFFLYSKL TVDKSRWQQGNVFSCSVMHEALHNHYTQKSLSLSPG |
| 41 | Human IgG1 (L235A, G237A) | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPELAGAPSVFLFP PKPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG |
| 42 | Human IgG1 YTE | ASTKGPSVFPLAPSSKSTSGGTAALGCLVKDYFPEPVTVSWN SGALTSGVHTFPAVLQSSGLYSLSSVVTVPSSSLGTQTYICNV NHKPSNTKVDKKVEPKSCDKTHTCPPCPAPELLGGPSVFLFP PKPKDTLYITREPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPSRDELTKNQVSLTCL VKGFYPSDIAVEWESNGQPENNYKTTPPVLDSDGSFFLYSKL TVDKSRWQQGNVFSCSVMHEALHNHYTQKSLSLSPG |

-continued

| SEQ ID NO | Name | Sequence |
|---|---|---|
| 43 | Human IgG2DASS | ASTKGPSVFPLAPCSRSTSESTAALGCLVKDYFPEPVTVSWNS GALTSGVHTFPAVLQSSGLYSLSSVVTVPSSNFGTQTYTCNV DHKPSNTKVDKTVERKCCVECPPCPAPPVAGPSVFLFPPKPK DTLMISRTPEVTCVVVDVSHEDPEVQFNWYVDGVEVHNAK TKPREEQFNSTFRVVSVLTVVHQDWLNGKEYKCKVSNKGLP SSIEKTISKTKGQPREPQVYTLPPSREEMTKNQVSLTCLVKGF YPSDIAVEWESNGQPENNYKTTPPMLDSDGSFFLYSKLTVDK SRWQQGNVFSCSVMHEALHNHYTQKSLSLSPG |
| 44 | Human IgG4 | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFLGGPSVFLFPPKPK DTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLTCLVKGF YPSDIAVEWESNGQPENNYKTTPPVLDSDGSFFLYSRLTVDK SRWQEGNVFSCSVMHEALHNHYTQKSLSLSLG |
| 45 | Human IgG4 KiH Hole | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFLGGPSVFLFPPKPK DTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLSCAVKGF YPSDIAVEWESNGQPENNYKTTPPVLDSDGSFFLYSRLTVDK SRWQEGNVFSCSVMHEALHNHYTQKSLSLSLG |
| 46 | Human IgG4 KiH Knob | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFLGGPSVFLFPPKPK DTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLWCLVKG FYPSDIAVEWESNGQPENNYKTTPPVLDSDGSFFLYSRLTVD KSRWQEGNVFSCSVMHEALHNHYTQKSLSLSLG |
| 47 | Human IgG4 (L235A, G237A) | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFAGAPSVFLFPPKPK DTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLTCLVKGF YPSDIAVEWESNGQPENNYKTTPPVLDSDGSFFLYSRLTVDK SRWQEGNVFSCSVMHEALHNHYTQKSLSLSLG |
| 48 | Human IgG4 (L235E) | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFEGGPSVFLFPPKPK DTLMISRTPEVTCVVVDVSQEDPEVQFNWYVDGVEVHNAK TKPREEQFNSTYRVVSVLTVLHQDWLNGKEYKCKVSNKGLP SSIEKTISKAKGQPREPQVYTLPPSQEEMTKNQVSLTCLVKGF YPSDIAVEWESNGQPENNYKTTPPVLDSDGSFFLYSRLTVDK SRWQEGNVFSCSVMHEALHNHYTQKSLSLSLG |
| 49 | Human IgG4 YTE | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFLGGPSVFLFPPKPK DTLYITREPEVTCVVVDVSQEDPEVQFNWYVDGVEVHNAKT KPREEQFNSTYRVVSVLTVLHQDWLNGKEYKCKVSNKGLPS SIEKTISKAKGQPREPQVYTLPPSQEEMTKNQVSLTCLVKGFY PSDIAVEWESNGQPENNYKTTPPVLDSDGSFFLYSRLTVDKS RWQEGNVFSCSVMHEALHNHYTQKSLSLSLG |
| 50 | Human IgG4 YTE KiH Hole | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFLGGPSVFLFPPKPK DTLYITREPEVTCVVVDVSQEDPEVQFNWYVDGVEVHNAKT KPREEQFNSTYRVVSVLTVLHQDWLNGKEYKCKVSNKGLPS SIEKTISKAKGQPREPQVYTLPPSQEEMTKNQVSLSCAVKGF YPSDIAVEWESNGQPENNYKTTPPVLDSDGSFFLVSRLTVDK SRWQEGNVFSCSVMHEALHNHYTQKSLSLSLG |
| 51 | Human IgG4 YTE KiH Knob | ASTKGPSVFPLAPCSRSTSESTAALGCLVKDYFPEPVTVSWNS GALTSGVHTFPAVLQSSGLYSLSSVVTVPSSSLGTKTYTCNV DHKPSNTKVDKRVESKYGPPCPPCPAPEFLGGPSVFLFPPKPK DTLYITREPEVTCVVVDVSQEDPEVQFNWYVDGVEVHNAKT |

-continued

| SEQ ID NO | Name | Sequence |
|---|---|---|
| | | KPREEQFNSTYRVVSVLTVLHQDWLNGKEYKCKVSNKGLPS SIEKTISKAKGQPREPQVYTLPPSQEEMTKNQVSLWCLVKGF YPSDIAVEWESNGQPENNYKTTPPVLDSDGSFFLYSRLTVDK SRWQEGNVFSCSVMHEALHNHYTQKSLSLSLG |
| 52 | 605C, 919A, and 890C VH-CDR2 IMGT | IYPIFADT |
| 53 | 605/890-VL CDR2 IMGT | WAS |
| 54 | 919A-VL CDR2 IMGT | LVS |
| 55 | 605C, 890C VH CDR2 IMGT | AIDQDGSFAY |
| 56 | 919A VH CDR3 IMGT | AIDYDGSFAY |
| 57 | 605/890-VL CDR3 IMGT | WQGTWFDLT |
| 58 | 919A-VL CDR3 IMGT | WQGTHFPLT |
| 59 | 605C, 890C, 919AVH FW1 | EVQLVQSGAEVKKPGSSVKVSCKAS |
| 60 | 890C, 919A and 605C light chain FW1 | DIVMTQSPDSLAVSLGERATINCKSS |
| 61 | 605C, 919A VH CDR1 IMGT | GGTFSDSY |
| 62 | 605, 890C VL CDR1 IMGT | QSLLDADGKTY |
| 63 | 919A VL CDR1 IMGT | QSLLDSDGKTY |
| 64 | 605C, 890C, 919A VH FW2 | MHWVRQAPGQGLEWMGL |
| 65 | 605/890 VK, 919A VK FW2 | LNWLQQKPGQPPKRLIY |
| 66 | 605C, 890C VH, 919A FW4 | WGQGTLVTVSS |
| 67 | 606/890 VK, 919A VK FW4 | FGGGTKVEIK |
| 68 | 605C, 890C vh, 919A FW3 | RYAQKFQGRVTITADESTSTAYMELSSLRSEDTAVYYC |
| 69 | 605 vk, 890c vk, 919A vkFWS | TRESGVPDRFSGSGSGTDFTLTISSLQAEDVAVYYC |
| 70 | 890C, 627C HC | EVQLVQSGAEVKKPGSSVKVSCKASGGTFSDVYMHWVRQA PGQGLEWMGLIYPIFADTRYAQKFQGRVTITADESTSTAYME LSSLRSEDTAVYYCAIDQDGSFAYWGQGTLVTVSSASTKGPS VFPLAPCSRSTSESTAALGCLVKDYFPEPVTVSWNSGALTSG VHTFPAVLQSSGLYSLSSVVTVPSSNFGTQTYTCNVDHKPSN TKVDKTVERKCCVECPPCPAPPVAGPSVFLFPPKPKDTLMISR TPEVTCVVVDVSHEDPEVQFNWYVDGVEVHNAKTKPREEQ FNSTFRVVSVLTVVHQDWLNGKEYKCKVSNKGLPSSIEKTIS KTKGQPREPQVYTLPPSREEMTKNQVSLTCLVKGFYPSDIAV EWESNGQPENNYKTTPPMLDSDGSFFLYSKLTVDKSRWQQG NVFSCSVMHEALHNHYTQKSLSLSPG |
| 71 | 890C, 609C LC | DIVMTQSPDSLAVSLGERATINCKSSQSLLDADGKTYLNWLQ QKPGQPPKRLIYWASTRESGVPDRFSGSGSGTDFTLTISSLQA |

| SEQ ID NO | Name | Sequence |
|---|---|---|
| | | EDVAVYYCWQGTWFDLTFGGGTKVEIKRTVAAPSVFIFPPSD<br>EQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC |
| 72 | 608C, 609C HC | EVQLVQSGAEVKKPGSSVKVSCKASGGTFSDLYMHWVRQA<br>PGQGLEWMGLIYPIFADTRYAQKFQGRVTITADESTSTAYME<br>LSSLRSEDTAVYYCAIDQDGSFAYWGQGTLVTVSSASTKGPS<br>VFPLAPCSRSTSESTAALGCLVKDYFPEPVTVSWNSGALTSG<br>VHTFPAVLQSSGLYSLSSVVTVPSSNFGTQTYTCNVDHKPSN<br>TKVDKTVERKCCVECPPCPAPPVAGPSVFLFPPKPKDTLMISR<br>TPEVTCVVVDVSHEDPEVQFNWYVDGVEVHNAKTKPREEQ<br>FNSTFRVVSVLTVVHQDWLNGKEYKCKVSNKGLPSSIEKTIS<br>KTKGQPREPQVYTLPPSREEMTKNQVSLTCLVKGFYPSDIAV<br>EWESNGQPENNYKTTPPMLDSDGSFFLYSKLTVDKSRWQQG<br>NVFSCSVMHEALHNHYTQKSLSLSPG |
| 73 | 608C LC, 627C | DIVMTQSPDSLAVSLGERATINCKSSQSLLDSDGKTYLNWLQ<br>QKPGQPPKRLIYWASTRESGVPDRFSGSGSGTDFTLTISSLQA<br>EDVAVYYCWQGTWFDLTFGGGTKVEIKRTVAAPSVFIFPPSD<br>EQLKSGTASVVCLLNNFYPREAKVQWKVDNALQSGNSQES<br>VTEQDSKDSTYSLSSTLTLSKADYEKHKVYACEVTHQGLSSP<br>VTKSFNRGEC |
| 890C heavy chain with IgG1 (L235A, G237A) and YTE | | EVQLVQSGAEVKKPGSSVKVSCKASGGTFSDVYMHWVRQ<br>APGQGLEWMGLIYPIFADTRYAQKFQGRVTITADESTSTAY<br>MELSSLRSEDTAVYYCAIDQDGSFAYWGQGTLVTVSSASTK<br>GPSVFPLAPSSKSTSGGTAALGCLVKDYFPEPVTVSWNSGA<br>LTSGVHTFPAVLQSSGLYSLSSVVTVPSSSLGTQTYICNVNH<br>KPSNTKVDKKVEPKSCDKTHTCPPCPAPELAGAPSVFLFPPK<br>PKDTLYITREPEVTCVVVDVSHEDPEVKFNWYVDGVEVHN<br>AKTKPREEQYNSTYRVVSVLTVLHQDWLNGKEYKCKVSN<br>KALPAPIEKTISKAKGQPREPQVYTLPPSRDELTKNQVSLTC<br>LVKGFYPSDIAVEWESNGQPENNYKTTPPVLDSDGSFFLYS<br>KLTVDKSRWQQGNVFSCSVMHEALHNHYTQKSLSLSPG | 74 |
| 890C heavy chain with IgG1 (L235A, G237A) | | EVQLVQSGAEVKKPGSSVKVSCKASGGTFSDVYMHWVRQ<br>APGQGLEWMGLIYPIFADTRYAQKFQGRVTITADESTSTAY<br>MELSSLRSEDTAVYYCAIDQDGSFAYWGQGTLVTVSSASTK<br>GPSVFPLAPSSKSTSGGTAALGCLVKDYFPEPVTVSWNSGA<br>LTSGVHTFPAVLQSSGLYSLSSVVTVPSSSLGTQTYICNVNH<br>KPSNTKVDKKVEPKSCDKTHTCPPCPAPELAGAPSVFLFPPK<br>PKDTLMISRTPEVTCVVVDVSHEDPEVKFNWYVDGVEVHN<br>AKTKPREEQYNSTYRVVSVLTVLHQDWLNGKEYKCKVSN<br>KALPAPIEKTISKAKGQPREPQVYTLPPSRDELTKNQVSLTC<br>LVKGFYPSDIAVEWESNGQPENNYKTTPPVLDSDGSFFLYS<br>KLTVDKSRWQQGNVFSCSVMHEALHNHYTQKSLSLSPG | 75 |
| Human IgG1 (L235A, G237A), YTE | | ASTKGPSVFPLAPSSKSTSGGTAALGCLVKDYFPEPVTVSW<br>NSGALTSGVHTFPAVLQSSGLYSLSSVVTVPSSSLGTQTYIC<br>NVNHKPSNTKVDKKVEPKSCDKTHTCPPCPAPELAGAPSVF<br>LFPPKPKDTLYITREPEVTCVVVDVSHEDPEVKFNWYVDGV<br>EVHNAKTKPREEQYNSTYRVVSVLTVLHQDWLNGKEYKC<br>KVSNKALPAPIEKTISKAKGQPREPQVYTLPPSRDELTKNQV<br>SLTCLVKGFYPSDIAVEWESNGQPENNYKTTPPVLDSDGSFF<br>LYSKLTVDKSRWQQGNVFSCSVMHEALHNHYTQKSLSLSP<br>G | 76 |
| | PHM | HADGVFTSDFSKLLGQLSAKKYLESLM (SEQ ID NO: 77) |
| | Secretin | HSDGTFTSELSRLREGARLQRLLQGLV (SEQ ID NO: 78) |
| | Glucagon | HSQGTFTSDYSKYLDSRRAQDFVQWLMNT (SEQ ID NO: 79) |
| | GIP | YAEGTFISDYSIAMDKIHQQDFVNWLLAQKGKKNDWKHNITQ (SEQ ID NO: 80) |
| | GLP-1 | HAEGTFTSDVSSYLEGQAAKEFIAWLVKGR (SEQ ID NO: 81) |
| | GLP-2 | HADGSFSDEMNTILDNLAARDFINWLIQTKITD (SEQ ID NO: 82) |
| | GRF | YADAIFTNSYRKVLGQLSARKLLQDIMSRQQGESNQERGARARL (SEQ ID NO: 83) |

The invention claimed is:

1. An anti-pituitary adenylate-cyclase-activating polypeptide (PACAP) antibody, wherein said antibody comprises heavy chain variable region (VH)-CDR1, VH-CDR2, and VH-CDR3 sequences set forth in SEQ ID NOs: 9, 2, and 3, respectively; and light chain variable region (VL)-CDR1, VL-CDR2, and VL-CDR3 sequence set forth in SEQ ID NOs: 10, 5, and 6, respectively.

2. The antibody of claim 1, comprising the heavy chain and light chain framework region (FR) sequences derived from human gene IGHV1-69*01 and IGKV4-1*01, respectively, and functional variants thereof.

3. The antibody of claim 1, comprising heavy chain framework region (VHFR)-1, VHFR-2, VHFR-3, and VHFR-4 sequences set forth in SEQ ID NOs: 29-32, respectively; and light chain framework region (VLFR)-1, VLFR-2, VLFR-3, and VLFR-4 sequences set forth in SEQ ID NOs: 33-36, respectively.

4. The antibody of claim 1, comprising a VH sequence that is about 90%, about 95%, or about 99% identical to a sequence selected from SEQ ID NOs: 11 and 12, and a VL sequence that is about 90%, about 95%, or about 99% identical to a sequence selected from SEQ ID NOs: 20 and 21.

5. The antibody of claim 1, comprising a VH sequence selected from SEQ ID NOs: 11 and 12 and a VL sequence selected from SEQ ID NOs: 20 and 21.

6. The antibody of claim 1, comprising a VH sequence of SEQ ID NO: 11 or SEQ ID NO: 12, wherein the VH sequence has Glutamine (Q) instead of Glutamic Acid (E) at residue 1 of SEQ ID NO: 11 or 12.

7. The antibody of claim 1, comprising a heavy chain constant region sequence selected from the group consisting of SEQ ID NOs: 37-51 or 76 and a light chain constant region sequence selected from SEQ ID NOs: 23 and 24.

8. The antibody of claim 1, wherein the antibody is human, of humanized.

9. The antibody of claim 1, wherein the antibody has low or no immunogenicity profile.

10. The antibody of claim 1, wherein the antibody has a humanness score greater than or equal to about 89%.

11. The antibody of claim 1, wherein the antibody has a KD lower than or equal to about $5 \times 10^{-11}$ molar (M) as measured by SPR at 37° C.

12. The antibody of claim 1, wherein the antibody or antigen-binding fragment thereof has a KD lower than or equal to about $3 \times 10^{-11}$ molar (M) as measured by SPR at 37° C.

13. The antibody of claim 1, comprising a full length heavy chain sequence and a full length light chain sequence that is about 90%, about 95%, or about 99% identical to the sequences selected from the group consisting of:
a) SEQ ID NOs: 70 and 71, respectively;
b) SEQ ID NOs: 74 and 71, respectively;
c) SEQ ID NOs: 75 and 71, respectively;
d) SEQ ID NOs: 72 and 73, respectively;
e) SEQ ID NOs: 70 and 73, respectively; and
f) SEQ ID NOs: 72 and 71, respectively.

14. The antibody of claim 1, comprising a full length heavy chain sequence and a full length light chain sequence selected from the group consisting of:
a) SEQ ID NOs: 70 and 71, respectively;
b) SEQ ID NOs: 74 and 71, respectively;
c) SEQ ID NOs: 75 and 71, respectively;
d) SEQ ID NOs: 72 and 73, respectively;
e) SEQ ID NOs: 70 and 73, respectively; and
f) SEQ ID NOs: 72 and 71, respectively.

15. The antibody of claim 1, wherein the heavy chain sequence has Glutamine (Q) instead of Glutamic Acid (E) at residue 1 of SEQ ID NOs: 70 72, 74, and 75.

16. The antibody of claim 1, wherein the antibody is an antagonist of PACAP.

17. The antibody of claim 1, wherein the antibody specifically binds to PACAP.

18. A pharmaceutical composition comprising the antibody of claim 1 and a pharmaceutically acceptable carrier.

19. A method of treating a condition in an individual, comprising administering to the individual a therapeutically effective amount of the pharmaceutical composition of claim 18, wherein the condition is headache.

20. An anti-PACAP antibody, wherein said antibody comprises VH-CDR1, VH-CDR2, and VH-CDR3 sequences and VL-CDR1, VL-CDR2, and VL-CDR3 sequences selected from the group consisting of:
a) SEQ ID NOs: 1, 2, and 3 and SEQ ID NO: 4, 5, and 6, respectively;
b) SEQ ID NOs: 7, 2, and 3 and SEQ ID NO: 8, 5, and 6, respectively;
c) SEQ ID NOs: 1, 2, and 3 and SEQ ID NO: 8, 5, and 6, respectively; and
d) SEQ ID NOs: 7, 2, and 3 and SEQ ID NO: 4, 5, and 6, respectively.

* * * * *

SEQUENCE LISTING

```
Sequence total quantity: 89
SEQ ID NO: 1            moltype = AA  length = 10
FEATURE                 Location/Qualifiers
source                  1..10
                        mol_type = protein
                        organism = synthetic construct
SEQUENCE: 1
GGTFSDVYMH                                                              10

SEQ ID NO: 2            moltype = AA  length = 6
FEATURE                 Location/Qualifiers
source                  1..6
                        mol_type = protein
                        organism = synthetic construct
SEQUENCE: 2
YPIFAD                                                                  6

SEQ ID NO: 3            moltype = AA  length = 8
FEATURE                 Location/Qualifiers
source                  1..8
                        mol_type = protein
                        organism = synthetic construct
SEQUENCE: 3
DQDGSFAY                                                                8

SEQ ID NO: 4            moltype = AA  length = 5
FEATURE                 Location/Qualifiers
source                  1..5
                        mol_type = protein
                        organism = synthetic construct
SEQUENCE: 4
DADGK                                                                   5

SEQ ID NO: 5            moltype = AA  length = 7
FEATURE                 Location/Qualifiers
source                  1..7
                        mol_type = protein
                        organism = synthetic construct
SEQUENCE: 5
WASTRES                                                                 7

SEQ ID NO: 6            moltype = AA  length = 9
FEATURE                 Location/Qualifiers
source                  1..9
                        mol_type = protein
                        organism = synthetic construct
SEQUENCE: 6
WQGTWFDLT                                                               9

SEQ ID NO: 7            moltype = AA  length = 10
FEATURE                 Location/Qualifiers
source                  1..10
                        mol_type = protein
                        organism = synthetic construct
SEQUENCE: 7
GGTFSDLYMH                                                              10

SEQ ID NO: 8            moltype = AA  length = 5
FEATURE                 Location/Qualifiers
source                  1..5
                        mol_type = protein
                        organism = synthetic construct
SEQUENCE: 8
DSDGK                                                                   5

SEQ ID NO: 9            moltype = AA  length = 10
FEATURE                 Location/Qualifiers
VARIANT                 7
                        note = X can be any naturally occurring amino acid
source                  1..10
                        mol_type = protein
                        organism = synthetic construct
SEQUENCE: 9
GGTFSDXYMH                                                              10

SEQ ID NO: 10           moltype = AA  length = 5
FEATURE                 Location/Qualifiers
VARIANT                 2
```

```
                        note = X can be any naturally occurring amino acid
source                  1..5
                        mol_type = protein
                        organism = synthetic construct
SEQUENCE: 10
DXDGK                                                                      5

SEQ ID NO: 11           moltype = AA   length = 117
FEATURE                 Location/Qualifiers
source                  1..117
                        mol_type = protein
                        organism = synthetic construct
SEQUENCE: 11
EVQLVQSGAE VKKPGSSVKV SCKASGGTFS DVYMHWVRQA PGQGLEWMGL IYPIFADTRY          60
AQKFQGRVTI TADESTSTAY MELSSLRSED TAVYYCAIDQ DGSFAYWGQG TLVTVSS            117

SEQ ID NO: 12           moltype = AA   length = 117
FEATURE                 Location/Qualifiers
source                  1..117
                        mol_type = protein
                        organism = synthetic construct
SEQUENCE: 12
EVQLVQSGAE VKKPGSSVKV SCKASGGTFS DLYMHWVRQA PGQGLEWMGL IYPIFADTRY          60
AQKFQGRVTI TADESTSTAY MELSSLRSED TAVYYCAIDQ DGSFAYWGQG TLVTVSS            117

SEQ ID NO: 13           moltype = AA   length = 38
FEATURE                 Location/Qualifiers
source                  1..38
                        mol_type = protein
                        organism = synthetic construct
SEQUENCE: 13
HSDGIFTDSY SRYRKQMAVK KYLAAVLGKR YKQRVKNK                                  38

SEQ ID NO: 14           moltype = AA   length = 27
FEATURE                 Location/Qualifiers
source                  1..27
                        mol_type = protein
                        organism = synthetic construct
SEQUENCE: 14
HSDGIFTDSY SRYRKQMAVK KYLAAVL                                              27

SEQ ID NO: 15           moltype = AA   length = 28
FEATURE                 Location/Qualifiers
source                  1..28
                        mol_type = protein
                        organism = synthetic construct
SEQUENCE: 15
HSDAVFTDNY TRLRKQMAVK KYLNSILN                                             28

SEQ ID NO: 16           moltype = AA   length = 7
FEATURE                 Location/Qualifiers
source                  1..7
                        mol_type = protein
                        organism = synthetic construct
SEQUENCE: 16
WASTRES                                                                    7

SEQ ID NO: 17           moltype = AA   length = 98
FEATURE                 Location/Qualifiers
source                  1..98
                        mol_type = protein
                        organism = synthetic construct
SEQUENCE: 17
QVQLVQSGAE VKKPGSSVKV SCKASGGTFS SYAISWVRQA PGQGLEWMGG IIPIFGTANY          60
AQKFQGRVTI TADESTSTAY MELSSLRSED TAVYYCAR                                  98

SEQ ID NO: 18           moltype = AA   length = 117
FEATURE                 Location/Qualifiers
source                  1..117
                        mol_type = protein
                        organism = synthetic construct
SEQUENCE: 18
EVQLVQSGAE VKKPGSSVKV SCKASGGTFS DSYMHWVRQA PGQGLEWMGL IYPIFADTRY          60
AQKFQGRVTI TADESTSTAY MELSSLRSED TAVYYCAIDY DGSFAYWGQG TLVTVSS            117

SEQ ID NO: 19           moltype = AA   length = 117
FEATURE                 Location/Qualifiers
source                  1..117
                        mol_type = protein
```

```
                              organism = synthetic construct
SEQUENCE: 19
EVQLVQSGAE VKKPGSSVKV SCKASGGTFS DSYMHWVRQA PGQGLEWMGL IYPIFADTRY     60
AQKFQGRVTI TADESTSTAY MELSSLRSED TAVYYCAIDQ DGSFAYWGQG TLVTVSS        117

SEQ ID NO: 21               moltype = AA   length = 112
FEATURE                     Location/Qualifiers
source                      1..112
                              mol_type = protein
                              organism = synthetic construct
SEQUENCE: 20
DIVMTQSPDS LAVSLGERAT INCKSSQSLL DADGKTYLNW LQQKPGQPPK RLIYWASTRE     60
SGVPDRFSGS GSGTDFTLTI SSLQAEDVAV YYCWQGTWFD LTFGGGTKVE IK             112

SEQ ID NO: 21               moltype = AA   length = 112
FEATURE                     Location/Qualifiers
source                      1..112
                              mol_type = protein
                              organism = synthetic construct
SEQUENCE: 21
DIVMTQSPDS LAVSLGERAT INCKSSQSLL DSDGKTYLNW LQQKPGQPPK RLIYWASTRE     60
SGVPDRFSGS GSGTDFTLTI SSLQAEDVAV YYCWQGTWFD LTFGGGTKVE IK             112

SEQ ID NO: 22               moltype = AA   length = 112
FEATURE                     Location/Qualifiers
source                      1..112
                              mol_type = protein
                              organism = synthetic construct
SEQUENCE: 22
DIVMTQSPDS LAVSLGERAT INCKSSQSLL DSDGKTYLNW LQQKPGQPPK RLIYLVSTRE     60
SGVPDRFSGS GSGTDFTLTI SSLQAEDVAV YYCWQGTWFD LTFGGGTKVE IK             112

SEQ ID NO: 23               moltype = AA   length = 107
FEATURE                     Location/Qualifiers
source                      1..107
                              mol_type = protein
                              organism = synthetic construct
SEQUENCE: 23
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                   107

SEQ ID NO: 24               moltype = AA   length = 106
FEATURE                     Location/Qualifiers
source                      1..106
                              mol_type = protein
                              organism = synthetic construct
SEQUENCE: 24
GQPKAAPSVT LFPPSSEELQ ANKATLVCLI SDFYPGAVTV AWKADSSPVK AGVETTTPSK     60
QSNNKYAASS YLSLTPEQWK SHRSYSCQVT HEGSTVEKTV APTECS                    106

SEQ ID NO: 25               moltype = AA   length = 8
FEATURE                     Location/Qualifiers
source                      1..8
                              mol_type = protein
                              organism = synthetic construct
SEQUENCE: 25
GGTFSDSY                                                              8

SEQ ID NO: 26               moltype = AA   length = 100
FEATURE                     Location/Qualifiers
source                      1..100
                              mol_type = protein
                              organism = synthetic construct
SEQUENCE: 26
DIVMTQSPDS LAVSLGERAT INCKSSQSVL YSNNKNYLAW YQQKPGQPPK LLIYWASTRE     60
SGVPDRFSGS GSGTDFTLTI SSLQAEDVAV YYCQQYYSTP                           100

SEQ ID NO: 27               moltype = AA   length = 112
FEATURE                     Location/Qualifiers
source                      1..112
                              mol_type = protein
                              organism = synthetic construct
SEQUENCE: 27
DIVMTQSPDS LAVSLGERAT INCKSSQSLL DSDGKTYLNW LQQKPGQPPK RLIYLVSTRE     60
SGVPDRFSGS GSGTDFTLTI SSLQAEDVAV YYCWQGTHFP LTFGGGTKVE IK             112

SEQ ID NO: 28               moltype = AA   length = 8
FEATURE                     Location/Qualifiers
source                      1..8
```

```
                        mol_type = protein
                        organism = synthetic construct
SEQUENCE: 28
GGTFSDVY                                                               8

SEQ ID NO: 29           moltype = AA   length = 25
FEATURE                 Location/Qualifiers
source                  1..25
                        mol_type = protein
                        organism = synthetic construct
SEQUENCE: 29
EVQLVQSGAE VKKPGSSVKV SCKAS                                           25

SEQ ID NO: 30           moltype = AA   length = 16
FEATURE                 Location/Qualifiers
source                  1..16
                        mol_type = protein
                        organism = synthetic construct
SEQUENCE: 30
WVRQAPGQGL EWMGLI                                                     16

SEQ ID NO: 31           moltype = AA   length = 41
FEATURE                 Location/Qualifiers
source                  1..41
                        mol_type = protein
                        organism = synthetic construct
SEQUENCE: 31
TRYAQKFQGR VTITADESTS TAYMELSSLR SEDTAVYYCA I                         41

SEQ ID NO: 32           moltype = AA   length = 11
FEATURE                 Location/Qualifiers
source                  1..11
                        mol_type = protein
                        organism = synthetic construct
SEQUENCE: 32
WGQGTLVTVS S                                                          11

SEQ ID NO: 33           moltype = AA   length = 30
FEATURE                 Location/Qualifiers
source                  1..30
                        mol_type = protein
                        organism = synthetic construct
SEQUENCE: 33
DIVMTQSPDS LAVSLGERAT INCKSSQSLL                                      30

SEQ ID NO: 34           moltype = AA   length = 19
FEATURE                 Location/Qualifiers
source                  1..19
                        mol_type = protein
                        organism = synthetic construct
SEQUENCE: 34
TYLNWLQQKP GQPPKRLIY                                                  19

SEQ ID NO: 35           moltype = AA   length = 32
FEATURE                 Location/Qualifiers
source                  1..32
                        mol_type = protein
                        organism = synthetic construct
SEQUENCE: 35
GVPDRFSGSG SGTDFTLTIS SLQAEDVAVY YC                                   32

SEQ ID NO: 36           moltype = AA   length = 10
FEATURE                 Location/Qualifiers
source                  1..10
                        mol_type = protein
                        organism = synthetic construct
SEQUENCE: 36
FGGGTKVEIK                                                            10

SEQ ID NO: 37           moltype = AA   length = 329
FEATURE                 Location/Qualifiers
source                  1..329
                        mol_type = protein
                        organism = synthetic construct
SEQUENCE: 37
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
```

```
SEQ ID NO: 38              moltype = AA  length = 103
FEATURE                    Location/Qualifiers
source                     1..103
                           mol_type = protein
                           organism = synthetic construct
SEQUENCE: 38
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSC                  103

SEQ ID NO: 39              moltype = AA  length = 329
FEATURE                    Location/Qualifiers
source                     1..329
                           mol_type = protein
                           organism = synthetic construct
SEQUENCE: 39
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLSC AVKGFYPSDI AVEWESNGQP ENNYKTTPPV LDSDGSFFLV SKLTVDKSRW 300
QQGNVFSCSV MHEALHNHYT QKSLSLSPG                                  329

SEQ ID NO: 40              moltype = AA  length = 329
FEATURE                    Location/Qualifiers
source                     1..329
                           mol_type = protein
                           organism = synthetic construct
SEQUENCE: 40
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLWC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 41              moltype = AA  length = 329
FEATURE                    Location/Qualifiers
source                     1..329
                           mol_type = protein
                           organism = synthetic construct
SEQUENCE: 41
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 42              moltype = AA  length = 329
FEATURE                    Location/Qualifiers
source                     1..329
                           mol_type = protein
                           organism = synthetic construct
SEQUENCE: 42
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG 120
PSVFLFPPKP KDTLYITREP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 43              moltype = AA  length = 325
FEATURE                    Location/Qualifiers
source                     1..325
                           mol_type = protein
                           organism = synthetic construct
SEQUENCE: 43
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF 120
LFPPKPKDTL MISRTPEVTC VVVDVSHEDP EVQFNWYVDG VEVHNAKTKP REEQFNSTFR 180
VVSVLTVVHQ DWLNGKEYKC KVSNKGLPSS IEKTISKTKG QPREPQVYTL PPSREEMTKN 240
QVSLTCLVKG FYPSDIAVEW ESNGQPENNY KTTPPMLDSD GSFFLYSKLT VDKSRWQQGN 300
VFSCSVMHEA LHNHYTQKSL SLSPG                                      325

SEQ ID NO: 44              moltype = AA  length = 326
FEATURE                    Location/Qualifiers
```

```
source                    1..326
                          mol_type = protein
                          organism = synthetic construct
SEQUENCE: 44
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 45             moltype = AA  length = 326
FEATURE                   Location/Qualifiers
source                    1..326
                          mol_type = protein
                          organism = synthetic construct
SEQUENCE: 45
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLSCAVK GFYPSDIAVE WESNGQPENN YKTTPPVLDS DGSFFLVSRL TVDKSRWQEG  300
NVFSCSVMHE ALHNHYTQKS LSLSLG                                      326

SEQ ID NO: 46             moltype = AA  length = 326
FEATURE                   Location/Qualifiers
source                    1..326
                          mol_type = protein
                          organism = synthetic construct
SEQUENCE: 46
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLWCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 47             moltype = AA  length = 326
FEATURE                   Location/Qualifiers
source                    1..326
                          mol_type = protein
                          organism = synthetic construct
SEQUENCE: 47
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFAGAPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 48             moltype = AA  length = 326
FEATURE                   Location/Qualifiers
source                    1..326
                          mol_type = protein
                          organism = synthetic construct
SEQUENCE: 48
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFEGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 49             moltype = AA  length = 326
FEATURE                   Location/Qualifiers
source                    1..326
                          mol_type = protein
                          organism = synthetic construct
SEQUENCE: 49
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 50             moltype = AA  length = 326
FEATURE                   Location/Qualifiers
source                    1..326
```

```
                    mol_type = protein
                    organism = synthetic construct
SEQUENCE: 50
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LYITREPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLSCAVK GFYPSDIAVE WESNGQPENN YKTTPPVLDS DGSFFLVSRL TVDKSRWQEG   300
NVFSCSVMHE ALHNHYTQKS LSLSLG                                       326

SEQ ID NO: 51          moltype = AA   length = 326
FEATURE                Location/Qualifiers
source                 1..326
                       mol_type = protein
                       organism = synthetic construct
SEQUENCE: 51
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LYITREPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLWCLVK GFYPSDIAVE WESNGQPENN YKTTPPVLDS DGSFFLYSRL TVDKSRWQEG   300
NVFSCSVMHE ALHNHYTQKS LSLSLG                                       326

SEQ ID NO: 52          moltype =      length =
SEQUENCE: 52
000

SEQ ID NO: 53          moltype =      length =
SEQUENCE: 53
000

SEQ ID NO: 54          moltype =      length =
SEQUENCE: 54
000

SEQ ID NO: 55          moltype = AA   length = 10
FEATURE                Location/Qualifiers
source                 1..10
                       mol_type = protein
                       organism = synthetic construct
SEQUENCE: 55
AIDQDGSFAY                                                          10

SEQ ID NO: 56          moltype = AA   length = 10
FEATURE                Location/Qualifiers
source                 1..10
                       mol_type = protein
                       organism = synthetic construct
SEQUENCE: 56
AIDYDGSFAY                                                          10

SEQ ID NO: 57          moltype = AA   length = 9
FEATURE                Location/Qualifiers
source                 1..9
                       mol_type = protein
                       organism = synthetic construct
SEQUENCE: 57
WQGTWFDLT                                                            9

SEQ ID NO: 58          moltype = AA   length = 9
FEATURE                Location/Qualifiers
source                 1..9
                       mol_type = protein
                       organism = synthetic construct
SEQUENCE: 58
WQGTHFPLT                                                            9

SEQ ID NO: 59          moltype = AA   length = 25
FEATURE                Location/Qualifiers
source                 1..25
                       mol_type = protein
                       organism = synthetic construct
SEQUENCE: 59
EVQLVQSGAE VKKPGSSVKV SCKAS                                         25

SEQ ID NO: 60          moltype = AA   length = 26
FEATURE                Location/Qualifiers
source                 1..26
                       mol_type = protein
```

```
                    organism = synthetic construct
SEQUENCE: 60
DIVMTQSPDS LAVSLGERAT INCKSS                                          26

SEQ ID NO: 61           moltype = AA  length = 8
FEATURE                 Location/Qualifiers
source                  1..8
                        mol_type = protein
                        organism = synthetic construct
SEQUENCE: 61
GGTFSDSY                                                               8

SEQ ID NO: 62           moltype = AA  length = 11
FEATURE                 Location/Qualifiers
source                  1..11
                        mol_type = protein
                        organism = synthetic construct
SEQUENCE: 62
QSLLDADGKT Y                                                          11

SEQ ID NO: 63           moltype = AA  length = 11
FEATURE                 Location/Qualifiers
source                  1..11
                        mol_type = protein
                        organism = synthetic construct
SEQUENCE: 63
QSLLDSDGKT Y                                                          11

SEQ ID NO: 64           moltype = AA  length = 17
FEATURE                 Location/Qualifiers
source                  1..17
                        mol_type = protein
                        organism = synthetic construct
SEQUENCE: 64
MHWVRQAPGQ GLEWMGL                                                    17

SEQ ID NO: 65           moltype = AA  length = 17
FEATURE                 Location/Qualifiers
source                  1..17
                        mol_type = protein
                        organism = synthetic construct
SEQUENCE: 65
LNWLQQKPGQ PPKRLIY                                                    17

SEQ ID NO: 66           moltype = AA  length = 11
FEATURE                 Location/Qualifiers
source                  1..11
                        mol_type = protein
                        organism = synthetic construct
SEQUENCE: 66
WGQGTLVTVS S                                                          11

SEQ ID NO: 67           moltype = AA  length = 10
FEATURE                 Location/Qualifiers
source                  1..10
                        mol_type = protein
                        organism = synthetic construct
SEQUENCE: 67
FGGGTKVEIK                                                            10

SEQ ID NO: 68           moltype = AA  length = 38
FEATURE                 Location/Qualifiers
source                  1..38
                        mol_type = protein
                        organism = synthetic construct
SEQUENCE: 68
RYAQKFQGRV TITADESTST AYMELSSLRS EDTAVYYC                             38

SEQ ID NO: 69           moltype = AA  length = 36
FEATURE                 Location/Qualifiers
source                  1..36
                        mol_type = protein
                        organism = synthetic construct
SEQUENCE: 69
TRESGVPDRF SGSGSGTDFT LTISSLQAED VAVYYC                               36

SEQ ID NO: 70           moltype = AA  length = 442
FEATURE                 Location/Qualifiers
source                  1..442
```

```
                            mol_type = protein
                            organism = synthetic construct
SEQUENCE: 70
EVQLVQSGAE VKKPGSSVKV SCKASGGTFS DVYMHWVRQA PGQGLEWMGL IYPIFADTRY    60
AQKFQGRVTI TADESTSTAY MELSSLRSED TAVYYCAIDQ DGSFAYWGQG TLVTVSSAST   120
KGPSVFPLAP CSRSTSESTA ALGCLVKDYF PEPVTVSWNS GALTSGVHTF PAVLQSSGLY   180
SLSSVVTVPS SNFGTQTYTC NVDHKPSNTK VDKTVERKCC VECPPCPAPP VAGPSVFLFP   240
PKPKDTLMIS RTPEVTCVVV DVSHEDPEVQ FNWYVDGVEV HNAKTKPREE QFNSTFRVVS   300
VLTVVHQDWL NGKEYKCKVS NKGLPSSIEK TISKTKGQPR EPQVYTLPPS REEMTKNQVS   360
LTCLVKGFYP SDIAVEWESN GQPENNYKTT PPMLDSDGSF FLYSKLTVDK SRWQQGNVFS   420
CSVMHEALHN HYTQKSLSLS PG                                           442

SEQ ID NO: 71          moltype = AA  length = 219
FEATURE                Location/Qualifiers
source                 1..219
                            mol_type = protein
                            organism = synthetic construct
SEQUENCE: 71
DIVMTQSPDS LAVSLGERAT INCKSSQSLL DADGKTYLNW LQQKPGQPPK RLIYWASTRE    60
SGVPDRFSGS GSGTDFTLTI SSLQAEDVAV YYCWQGTWFD LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 72          moltype = AA  length = 442
FEATURE                Location/Qualifiers
source                 1..442
                            mol_type = protein
                            organism = synthetic construct
SEQUENCE: 72
EVQLVQSGAE VKKPGSSVKV SCKASGGTFS DLYMHWVRQA PGQGLEWMGL IYPIFADTRY    60
AQKFQGRVTI TADESTSTAY MELSSLRSED TAVYYCAIDQ DGSFAYWGQG TLVTVSSAST   120
KGPSVFPLAP CSRSTSESTA ALGCLVKDYF PEPVTVSWNS GALTSGVHTF PAVLQSSGLY   180
SLSSVVTVPS SNFGTQTYTC NVDHKPSNTK VDKTVERKCC VECPPCPAPP VAGPSVFLFP   240
PKPKDTLMIS RTPEVTCVVV DVSHEDPEVQ FNWYVDGVEV HNAKTKPREE QFNSTFRVVS   300
VLTVVHQDWL NGKEYKCKVS NKGLPSSIEK TISKTKGQPR EPQVYTLPPS REEMTKNQVS   360
LTCLVKGFYP SDIAVEWESN GQPENNYKTT PPMLDSDGSF FLYSKLTVDK SRWQQGNVFS   420
CSVMHEALHN HYTQKSLSLS PG                                           442

SEQ ID NO: 73          moltype = AA  length = 219
FEATURE                Location/Qualifiers
source                 1..219
                            mol_type = protein
                            organism = synthetic construct
SEQUENCE: 73
DIVMTQSPDS LAVSLGERAT INCKSSQSLL DSDGKTYLNW LQQKPGQPPK RLIYWASTRE    60
SGVPDRFSGS GSGTDFTLTI SSLQAEDVAV YYCWQGTWFD LTFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 74          moltype = AA  length = 446
FEATURE                Location/Qualifiers
source                 1..446
                            mol_type = protein
                            organism = synthetic construct
REGION                 1..446
                            note = 890C heavy chain with IgG1 (L235A, G237A) and YTE
SEQUENCE: 74
EVQLVQSGAE VKKPGSSVKV SCKASGGTFS DVYMHWVRQA PGQGLEWMGL IYPIFADTRY    60
AQKFQGRVTI TADESTSTAY MELSSLRSED TAVYYCAIDQ DGSFAYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELAGAPSV   240
FLFPPKPKDT LYITREPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 75          moltype = AA  length = 446
FEATURE                Location/Qualifiers
source                 1..446
                            mol_type = protein
                            organism = synthetic construct
REGION                 1..446
                            note = 890C heavy chain with IgG1 (L235A, G237A)
SEQUENCE: 75
EVQLVQSGAE VKKPGSSVKV SCKASGGTFS DVYMHWVRQA PGQGLEWMGL IYPIFADTRY    60
AQKFQGRVTI TADESTSTAY MELSSLRSED TAVYYCAIDQ DGSFAYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELAGAPSV   240
FLFPPKPKDT LMISRTPEVT CVVVDVSHED PEVKFNWYVD GVEVHNAKTK PREEQYNSTY   300
```

```
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPG                                        446

SEQ ID NO: 76           moltype = AA  length = 329
FEATURE                 Location/Qualifiers
source                  1..329
                        mol_type = protein
                        organism = synthetic construct
REGION                  1..329
                        note = Human IgG1 (L235A, G237A), YTE
SEQUENCE: 76
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELAGA    120
PSVFLFPPKP KDTLYITREP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 77           moltype = AA  length = 27
FEATURE                 Location/Qualifiers
source                  1..27
                        mol_type = protein
                        organism = synthetic construct
REGION                  1..27
                        note = PHM
SEQUENCE: 77
HADGVFTSDF SKLLGQLSAK KYLESLM                                        27

SEQ ID NO: 78           moltype = AA  length = 27
FEATURE                 Location/Qualifiers
source                  1..27
                        mol_type = protein
                        organism = synthetic construct
REGION                  1..27
                        note = Secretin
SEQUENCE: 78
HSDGTFTSEL SRLREGARLQ RLLQGLV                                        27

SEQ ID NO: 79           moltype = AA  length = 29
FEATURE                 Location/Qualifiers
source                  1..29
                        mol_type = protein
                        organism = synthetic construct
REGION                  1..29
                        note = Glucagon
SEQUENCE: 79
HSQGTFTSDY SKYLDSRRAQ DFVQWLMNT                                      29

SEQ ID NO: 80           moltype = AA  length = 42
FEATURE                 Location/Qualifiers
source                  1..42
                        mol_type = protein
                        organism = synthetic construct
REGION                  1..42
                        note = GIP
SEQUENCE: 80
YAEGTFISDY SIAMDKIHQQ DFVNWLLAQK GKKNDWKHNI TQ                        42

SEQ ID NO: 81           moltype = AA  length = 30
FEATURE                 Location/Qualifiers
source                  1..30
                        mol_type = protein
                        organism = synthetic construct
REGION                  1..30
                        note = GLP-1
SEQUENCE: 81
HAEGTFTSDV SSYLEGQAAK EFIAWLVKGR                                     30

SEQ ID NO: 82           moltype = AA  length = 33
FEATURE                 Location/Qualifiers
source                  1..33
                        mol_type = protein
                        organism = synthetic construct
REGION                  1..33
                        note = GLP-2
SEQUENCE: 82
HADGSFSDEM NTILDNLAAR DFINWLIQTK ITD                                 33
```

| | | |
|---|---|---|
| SEQ ID NO: 83 | moltype = AA  length = 44 | |
| FEATURE | Location/Qualifiers | |
| source | 1..44 | |
| | mol_type = protein | |
| | organism = synthetic construct | |
| REGION | 1..44 | |
| | note = GRF | |
| SEQUENCE: 83 | | |
| YADAIFTNSY RKVLGQLSAR KLLQDIMSRQ QGESNQERGA RARL | | 44 |
| | | |
| SEQ ID NO: 84 | moltype = AA  length = 112 | |
| FEATURE | Location/Qualifiers | |
| source | 1..112 | |
| | mol_type = protein | |
| | organism = synthetic construct | |
| REGION | 1..112 | |
| | note = 054M VL | |
| SEQUENCE: 84 | | |
| DIVMTQSPDS LAVSLGERAT INCKSSQSLL DSDGKTYLNW LQQKPGQPPK RLIYLVSKLD | | 60 |
| SGVPDRFSGS GSGTDFTLTI SSLQAEDVAV YYCWQGTHFP LTFGGGTKVE IK | | 112 |
| | | |
| SEQ ID NO: 85 | moltype = AA  length = 117 | |
| FEATURE | Location/Qualifiers | |
| source | 1..117 | |
| | mol_type = protein | |
| | organism = synthetic construct | |
| REGION | 1..117 | |
| | note = 054M VH | |
| SEQUENCE: 85 | | |
| EVQLVQSGAE VKKPGSSVKV SCKASGFTFT DSYMHWVRQA PGQGLEWMGL IYPFSADTRY | | 60 |
| AQKFQGRVTI TADESTSTAY MELSSLRSED TAVYYCAIDY DGSFAYWGQG TLVTVSS | | 117 |
| | | |
| SEQ ID NO: 86 | moltype = AA  length = 112 | |
| FEATURE | Location/Qualifiers | |
| source | 1..112 | |
| | mol_type = protein | |
| | organism = synthetic construct | |
| REGION | 1..112 | |
| | note = 604C VL | |
| SEQUENCE: 86 | | |
| DIVMTQSPDS LAVSLGERAT INCKSSQSLL DSDGKTYLNW LQQKPGQPPK RLIYWASTRE | | 60 |
| SGVPDRFSGS GSGTDFTLTI SSLQAEDVAV YYCWQGTWFD LTFGGGTKVE IK | | 112 |
| | | |
| SEQ ID NO: 87 | moltype = AA  length = 117 | |
| FEATURE | Location/Qualifiers | |
| source | 1..117 | |
| | mol_type = protein | |
| | organism = synthetic construct | |
| REGION | 1..117 | |
| | note = 604C VH | |
| SEQUENCE: 87 | | |
| EVQLVQSGAE VKKPGSSVKV SCKASGGTFS DSYMHWVRQA PGQGLEWMGL IYPIFADTRY | | 60 |
| AQKFQGRVTI TADESTSTAY MELSSLRSED TAVYYCAIDQ DGSFAYWGQG TLVTVSS | | 117 |
| | | |
| SEQ ID NO: 88 | moltype = AA  length = 112 | |
| FEATURE | Location/Qualifiers | |
| source | 1..112 | |
| | mol_type = protein | |
| | organism = synthetic construct | |
| REGION | 1..112 | |
| | note = 605C VL | |
| SEQUENCE: 88 | | |
| DIVMTQSPDS LAVSLGERAT INCKSSQSLL DADGKTYLNW LQQKPGQPPK RLIYWASTRE | | 60 |
| SGVPDRFSGS GSGTDFTLTI SSLQAEDVAV YYCWQGTWFD LTFGGGTKVE IK | | 112 |
| | | |
| SEQ ID NO: 89 | moltype = AA  length = 117 | |
| FEATURE | Location/Qualifiers | |
| source | 1..117 | |
| | mol_type = protein | |
| | organism = synthetic construct | |
| REGION | 1..117 | |
| | note = 605C VH | |
| SEQUENCE: 89 | | |
| EVQLVQSGAE VKKPGSSVKV SCKASGGTFS DSYMHWVRQA PGQGLEWMGL IYPIFADTRY | | 60 |
| AQKFQGRVTI TADESTSTAY MELSSLRSED TAVYYCAIDQ DGSFAYWGQG TLVTVSS | | 117 |